(12) United States Patent
Inui et al.

(10) Patent No.: US 10,208,313 B2
(45) Date of Patent: Feb. 19, 2019

(54) CORYNEFORM BACTERIUM TRANSFORMANT AND PROCESS FOR PRODUCING ORGANIC COMPOUND USING THE SAME

(71) Applicant: RESEARCH INSTITUTE OF INNOVATIVE TECHNOLOGY FOR THE EARTH, Kyoto (JP)

(72) Inventors: Masayuki Inui, Kyoto (JP); Masako Suda, Kyoto (JP); Kazumi Hiraga, Kyoto (JP); Takahisa Kogure, Kyoto (JP)

(73) Assignee: RESEARCH INSTITUTE OF INNOVATIVE TECHNOLOGY FOR THE EARTH, Kyoto (JP)

( * ) Notice: Subject to any disclaimer, the term of this patent is extended or adjusted under 35 U.S.C. 154(b) by 158 days.

(21) Appl. No.: 15/503,813

(22) PCT Filed: Aug. 20, 2015

(86) PCT No.: PCT/JP2015/073436
§ 371 (c)(1),
(2) Date: Feb. 14, 2017

(87) PCT Pub. No.: WO2016/027870
PCT Pub. Date: Feb. 25, 2016

(65) Prior Publication Data
US 2018/0044688 A1    Feb. 15, 2018

(30) Foreign Application Priority Data
Aug. 21, 2014   (JP) ................................ 2014-168646

(51) Int. Cl.
| | |
|---|---|
| *C12N 9/12* | (2006.01) |
| *C12P 7/42* | (2006.01) |
| *C12N 15/09* | (2006.01) |
| *C12N 15/77* | (2006.01) |
| *C12N 15/87* | (2006.01) |
| *C12P 13/22* | (2006.01) |

(52) U.S. Cl.
CPC ........... *C12N 15/77* (2013.01); *C12N 9/1217* (2013.01); *C12N 15/09* (2013.01); *C12N 15/87* (2013.01); *C12P 7/42* (2013.01); *C12P 13/22* (2013.01)

(58) Field of Classification Search
CPC combination set(s) only.
See application file for complete search history.

(56) References Cited

U.S. PATENT DOCUMENTS

| 6,436,664 B1 | 8/2002 | Iomantas et al. |
| 6,472,169 B1 | 10/2002 | Frost et al. |
| 6,613,552 B1 | 9/2003 | Frost et al. |
| 2008/0241898 A1 | 10/2008 | Valle et al. |
| 2009/0191610 A1 | 7/2009 | Zelder et al. |

FOREIGN PATENT DOCUMENTS

| JP | 2002-281993 | 10/2002 |
| JP | 2007-295809 | 11/2007 |
| JP | 2009-504172 | 2/2009 |

OTHER PUBLICATIONS

International Search Report dated Nov. 10, 2015 in International Application No. PCT/JP2015/073436.
Takeshi Kubota et al., "Characterization of shikimate dehydrogenase homologues of Corynebacterium glutamicum", Proceedings (online) of the Annual Meeting of the Japan Society for Bioscience, Biotechnology, and Agrochemistry, 2013, Japan Society for Bioscience, Biotechnology, and Agrochemistry, Mar. 5, 2013, 3B12p16.
Masayuki Inui et al., "Ethanol production from lignocellulose-derived mixed sugars by the RITE bioprocess", Proceedings (online) of the Annual Meeting of the Japan Society for Bioscience, Biotechnology, and Agrochemistry, 2013, Japan Society For Bioscience, Biotechnology, and Agrochemistry, Mar. 5, 2013, 3C11p14.
Takahisa Kogure et al., "Production of shikimic acid as a precursor of aromatic compounds by metabolically engineered *Corynebacterium glutamicum*", Proceedings (online) of the Annual Meeting of the Japan Society for Bioscience, Biotechnology, and Agrochemistry, 2015, Mar. 5, 2015, 2B33a07.
Sunil S. Chandran et al., "Phosphoenolpyruvate Availability and the Biosynthesis of Shikimic Acid", Biotechnology Progress, 2003, 19, 808-814.
Alberto Rodriguez et al., "Constitutive expression of selected genes from the pentose phosphate and aromatic pathways increases the shikimic acid yield in high-glucose batch cultures of an *Escherichia coli* strain lacking PTS and pykF", Microbial Cell Factories, 2013, 12:86.
Extended European Search Report dated Feb. 5, 2018 in corresponding European patent application No. 15834577.7.
Draths et al., "Shikimic Acid and Quinic Acid: Replacing Isolation from Plant Sources with Recombinant Microbial Biocatalysis", J. Am. Chem. Soc., 1999, vol. 121, pp. 1603-1604, XP002161577.
Adachi et al., "High Shikimate Production from Quinate with Two Enzymatic Systems of Acetic Acid Bacteria", Biosci. Biotechnol. Biochem., 2006, vol. 70, No. 10, pp. 2579-2582, XP055433159.
Ghosh et al., "Production of shikimic acid", Biotechnology Advances, 2012, vol. 30, No. 6, pp. 1425-1431, XP055045228.
International Preliminary Report on Patentability dated Feb. 21, 2017 in corresponding International Application No. PCT/JP2015/073436.

*Primary Examiner* — Kagnew H Gebreyesus
(74) *Attorney, Agent, or Firm* — Wenderoth, Lind & Ponack, L.L.P.

(57) ABSTRACT

A coryneform bacterium transformant engineered by the following (A) to (D): (A) enhancement of 3-deoxy-D-arabino-heptulosonate-7-phosphate (DAHP) synthase activity; (B) prevention, inhibition, or reduction of intracellular sugar uptake mediated by phosphotransferase system (PTS); (C) enhancement of intracellular sugar uptake activity mediated by a sugar transporter different from phosphotransferase system and enhancement of glucokinase activity; and (D) enhancement of glyceraldehyde-3-phosphate dehydrogenase (GAPDH) activity is capable of efficiently producing shikimic acid or the like from a sugar.

21 Claims, 1 Drawing Sheet
Specification includes a Sequence Listing.

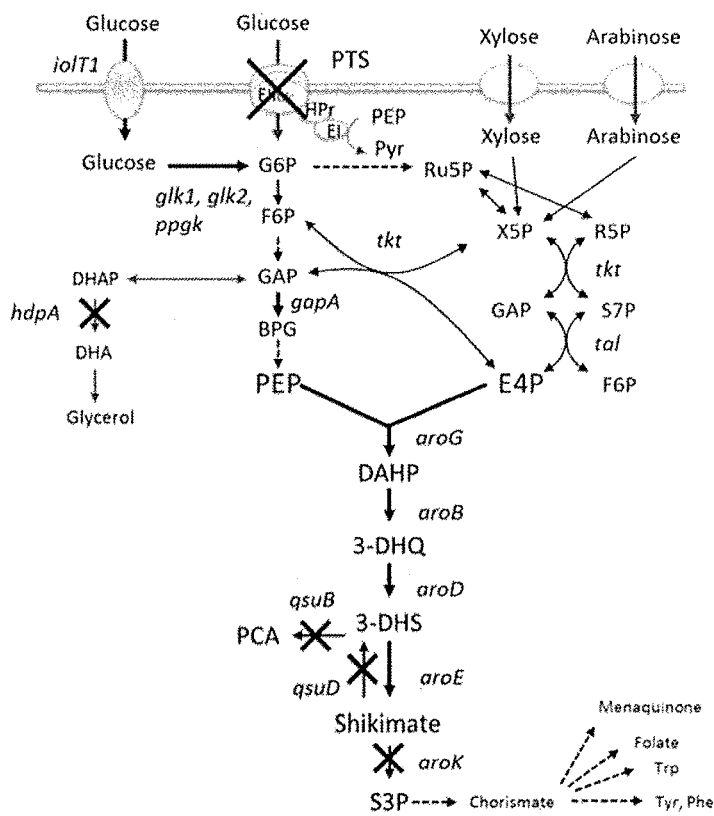

List of Abbreviations
PTS: phosphoenolpyruvate:sugar phosphotransferase system, iolT1: myo-inositol transporter, glk: glucokinase, ppgK: polyphosphate/ATP dependent glucokinase, hdpA: HAD(haloacid dehalogenase) superfamily phosphatase, gapA: glyceraldehyde-3-phosphate dehydrogenase
tkt: transketolase, tal: transaldolase, aroG: DAHP(3-deoxy-D-arabino-heptulosonate-7-phosphate) synthase, aroB: 3-dehydroquinate(3-DHQ) synthase, aroD: 3-dehydroquinate(3-DHQ) dehydratase, aroE: shikimate dehydrogenase, aroK: shikimate kinase, qsuB: 3-dehydroshikimate(3-DHS) dehydratase, qsuD: quinate/shikimate dehydrogenase,
PEP: phosphoenolpyruvate, Pyr: pyruvate, G6P: glucose 6-phosphate, GAP: glyceraldehyde 3-phosphate, BPG: glycerate 1,3-bisphosphate, DHAP: dihydroxyacetone phosphate, DHA: dihydroxyacetone, E4P: erythrose 4-phosphate, X5P: xylulose 5-phosphate, R5P: ribose 5-phosphate, S7P: sedoheptulose 7-phosphate, Ru5P: ribulose 5-phosphate, PCA: protocatechuic acid

CORYNEFORM BACTERIUM TRANSFORMANT AND PROCESS FOR PRODUCING ORGANIC COMPOUND USING THE SAME This application is a 371 national stage of PCT/JP2015/073436 filed on Aug. 20, 2015 and claims priority from Japanese application JP2014-168646 filed on Aug. 21, 2014.

TECHNICAL FIELD

The present invention relates to a coryneform bacterium transformant engineered to industrially produce shikimic acid and relates to an efficient process for producing an organic compound using the coryneform bacterium transformant.

BACKGROUND ART

Shikimic acid is an optically active substance having three chiral carbons in its molecule, and is used as a raw material for the synthesis of a large number of medicines, agrichemicals, cosmetics, and the like. In particular, shikimic acid is known to be an important starting material for the chemical synthesis of Tamiflu (registered trademark), a medicine to treat influenza. Recently; the efficacy of Tamiflu for avian influenza, of which the pandemic is a great concern, has been demonstrated, and for this reason, there is a growing demand for shikimic acid as a raw material of Tamiflu. Also, shikimic acid can be chemically converted into useful chemicals, such as p-hydroxybenzoic acid and phenol, and is promising as a raw material for the synthesis thereof.

Shikimic acid has conventionally been obtained by extraction from the fruits of plants, such as *Illicium anisatum* and *Illicium verum*. However, the extraction and purification methods are complicated and of low yield, and in addition, since the raw materials are natural products, it is difficult to stably supply a large amount thereof.

Meanwhile, shikimic acid is an important intermediate in the aromatic compound biosynthetic pathway of bacteria, yeasts, plants, etc., and can be produced by fermentation using microorganisms having this pathway. Production of shikimic acid using *Escherichia coli* as a host has been reported so far (Patent Literature 1 to 7), but in the methods, quinic acid produced as a by-product together with shikimic acid is a factor hindering the purification of shikimic acid. Further, since shikimic acid is produced in association with aerobic growth in each method, glucose, which is a raw material of shikimic acid, is largely used for bacterial growth, resulting in low yield of shikimic acid as the objective substance. For example, the shikimic acid yield described in Patent Literature 4 and 6 is as low as 27%. The maximum yield of shikimic acid from glucose described in Patent Literature 1 is 43%, but here the possibilities of reproduction of phosphoenol pyruvate from pyruvic acid and glucose uptake by non-phosphotransferase system, etc. are not taken into consideration. Therefore, the actual maximum theoretical yield of shikimic acid from glucose is considered to be 86%. When this theoretical yield is used as a baseline, the above sugar-based yield of shikimic acid 27% is calculated to be 31% of the theoretical yield, which is also low.

Patent Literature 8 reports shikimic acid production using a mutant strain of *Citrobacter freundii*, the mutant strain having resistance to 4-hydroxy-3-methoxybenzoic acid as a 4-hydroxybenzoic acid analog. However, regarding the mutant strain, the mutation site is unknown, the concentration of shikimic acid produced is low, and the sugar-based yield is also unknown.

Patent Literature 9 and 10 report shikimic acid production using an aromatic amino acid auxotroph of *Bacillus subtilis*, but regarding the auxotroph, the mutation site is unknown, the concentration of shikimic acid produced is low, and the sugar-based yield is also unknown.

CITATION LIST

Patent Literature

Patent Literature 1:
JP 4669613 Biocatalytic synthesis of shikimic acid
Patent Literature 2:
JP 2002-535008 W Biocatalytic synthesis of shikimic acid
Patent Literature 3:
U.S. Pat. No. 6,613,552 Biocatalytic synthesis of shikimic acid
Patent Literature 4:
U.S. Pat. No. 6,472,169 Biocatalytic synthesis of shikimic acid
Patent Literature 5:
EP 1151126 Biocatalytic synthesis of shikimic acid
Patent Literature 6:
WO 02/29078 Biocatalytic synthesis of shikimic acid
Patent Literature 7:
WO 2000/044923 Biocatalytic synthesis of shikimic acid
Patent Literature 8:
JP 2002-281993 A Method for producing shikimic acid
Patent literature 9:
U.S. Pat. No. 6,436,664 Method for producing shikimic acid
Patent Literature 10:
JP 2000-287695 A Method for producing shikimic acid

Non Patent Literature

Non Patent literature 1:
Biotechnology Progress (2003) 19, 808-814
Non Patent literature 2:
Microbial Cell Factories (2013) 12:86

SUMMARY OF INVENTION

Technical Problem

An object of the present invention is to provide a microorganism capable of efficiently producing shikimic acid from sugars, and a process for efficiently producing an organic compound, such as shikimic acid, from sugars using the microorganism.

Solution to Problem

The present inventors wholeheartedly carried out investigations in order to achieve the object described above and found that a coryneform bacterium engineered by the following (A) to (D) can produce shikimic acid from glucose or the like at a high concentration and in good yield. The inventors also found that, when the thus-engineered coryneform bacterium is used, quinic acid produced as a by-product, which has been a long-lasting problem in shikimic acid production, is in a very small amount.

A) Enhancement of 3-deoxy-D-arabino-heptulosonate-7-phosphate (DAHP) synthase activity
(B) Prevention, inhibition, or reduction of intracellular sugar uptake mediated by phosphoenolpyruvate:sugar phosphotransferase system (PTS)
(C) Enhancement of intracellular sugar uptake activity mediated by a sugar transporter different from phosphoenolpyruvate:sugar phosphotransferase system and enhancement of glucokinase activity
(D) Enhancement of glyceraldehyde-3-phosphate dehydrogenase (GAPDH) activity The inventors also found that the coryneform bacterium has a particularly higher shikimic acid productivity when the reaction is performed under aerobic conditions where the bacterium substantially does not grow.

The present invention, which has been completed based on the above-mentioned findings, provides the following coryneform bacterium transformants and processes for producing an organic compound.

[1] A coryneform bacterium transformant engineered by the following (A) to (D):
(A) enhancement of 3-deoxy-D-arabino-heptulosonate-7-phosphate (DAHP) synthase activity;
(B) prevention, inhibition, or reduction of intracellular sugar uptake mediated by phosphoenolpyruvate:sugar phosphotransferase system (PTS);
(C) enhancement of intracellular sugar uptake activity mediated by a sugar transporter different from phosphoenolpyruvate:sugar phosphotransferase system and enhancement of glucokinase activity; and
(D) enhancement of glyceraldehyde-3-phosphate dehydrogenase (GAPDH) activity.
[2] The coryneform bacterium transformant of the above [1], wherein dihydroxyacetone phosphate phosphatase activity is prevented, inhibited, or reduced.
[3] The coryneform bacterium transformant of the above [1] or [2], wherein one or more of 3-dehydroquinate synthase activity, 3-dehydroquinate dehydratase activity, and shikimate dehydrogenase activity are enhanced.
[4] The coryneform bacterium transformant of any one of the above [1] to [3], wherein one or more of transketolase activity and transaldolase activity are enhanced.
[5] The coryneform bacterium transformant of any one of the above [1] to [4], wherein one or more of shikimate kinase activity, quinate/shikimate dehydrogenase activity, and 3-dehydroshikimate dehydratase activity are prevented, inhibited, or reduced.
[6] The coryneform bacterium transformant of any one of the above [1] to [5], which is capable of utilizing glucose and at least one kind of sugar selected from the group consisting of xylose, arabinose, and cellobiose.
[7] The coryneform bacterium transformant of any one of the above [1] to [6], wherein 3-deoxy-D-arabino-heptulosonate-7-phosphate synthase activity is enhanced by a DNA introduced thereinto, the DNA being
(a) a DNA consisting of the base sequence of SEQ ID NO: 1; or
(b) a DNA consisting of a base sequence which has 90% or more of identity with the base sequence of SEQ ID NO: 1 and encodes 3-deoxy-D-arabino-heptulosonate-7-phosphate synthase.
[8] The coryneform bacterium transformant of any one of the above [1] to [7], wherein intracellular sugar uptake mediated by phosphoenolpyruvate:sugar phosphotransferase system (PTS) is prevented, inhibited, or reduced by disruption, deletion, or mutation of one or more of ptsH encoding histidine-phosphorylatable protein (HPr), ptsI encoding Enzyme I, and ptsG encoding glucose-specific Enzyme II as genes encoding components of PTS.
[9] The coryneform bacterium transformant of any one of the above [1] to [8], wherein the sugar transporter different from PTS is an inositol transporter.
[10] The coryneform bacterium transformant of the above [9], wherein the intracellular sugar uptake activity mediated by the inositol transporter is enhanced by a DNA introduced thereinto, the DNA being
(c) a DNA consisting of the base sequence of SEQ ID NO: 2; or
(d) a DNA consisting of a base sequence which has 90% or more of identity with the base sequence of SEQ ID NO: 2 and encodes the inositol transporter.
[11] The coryneform bacterium transformant of any one of the above [1] to [10], wherein the glucokinase activity is enhanced by a DNA introduced thereinto, the DNA being
(e) a DNA consisting of the base sequence of SEQ ID NO: 3, 4, or 5; or
(f) a DNA consisting of a base sequence which has 90% or more of identity with the base sequence of SEQ ID NO: 3, 4, or 5 and encodes glucokinase.
[12] The coryneform bacterium transformant of any one of the above [1] to [11], wherein the glyceraldehyde-3-phosphate dehydrogenase activity is enhanced by a DNA introduced thereinto, the DNA being
(g) a DNA consisting of the base sequence of SEQ ID NO: 6; or
(h) a DNA consisting of a base sequence which has 90% or more of identity with the base sequence of SEQ ID NO: 6 and encodes glyceraldehyde-3-phosphate dehydrogenase.
[13] The coryneform bacterium transformant of any one of the above [3] to [12], wherein the enhancement of the 3-dehydroquinate synthase activity is achieved by introducing
(i) a DNA consisting of the base sequence of SEQ ID NO: 7 or
(j) a DNA consisting of a base sequence which has 90% or more of identity with the base sequence of SEQ ID NO: 7 and encodes 3-dehydroquinate synthase;
the enhancement of the 3-dehydroquinate dehydratase activity is achieved by introducing
(k) a DNA consisting of the base sequence of SEQ ID NO: 8 or
(l) a DNA consisting of a base sequence which has 90% or more of identity with the base sequence of SEQ ID NO: 8 and encodes 3-dehydroquinate dehydratase; and
the enhancement of the shikimate dehydrogenase activity is achieved by introducing
(m) a DNA consisting of the base sequence of SEQ ID NO: 9 or
(n) a DNA consisting of a base sequence which has 90% or more of identity with the base sequence of SEQ ID NO: 9 and encodes shikimate dehydrogenase.
[14] The coryneform bacterium transformant of any one of the above [4] to [13], wherein the enhancement of the transketolase activity is achieved by introducing
(o) a DNA consisting of the base sequence of SEQ ID NO: 10 or
(p) a DNA consisting of a base sequence which has 90% or more of identity with the base sequence of SEQ ID NO: 10 and encodes transketolase; and
the enhancement of the transaldolase activity is achieved by introducing
(q) a DNA consisting of the base sequence of SEQ ID NO: 11 or (r) a DNA consisting of a base sequence which has 90% or more of identity with the base sequence of SEQ ID NO: 11 and encodes transaldolase.

[15] The coryneform bacterium transformant of any one of the above [1] to [14], wherein the coryneform bacterium is *Corynebacterium glutamicum*.

[16] The coryneform bacterium transformant of the above [15], which is *Corynebacterium glutamicum* R (FERM BP-18976), ATCC13032, or ATCC13869 strain engineered as described above.

[17] *Corynebacterium glutamicum* SKM7 (Accession Number: NITE BP-01903).

[18] A process for producing an organic compound, which comprises a step of culturing the transformant of any one of the above [1] to [17] in a reaction mixture containing a sugar, and a step of recovering at least one kind of organic compound selected from the group consisting of shikimic acid, 3-dehydroshikimic acid, 3-dehydroquinic acid, protocatechuic acid, chorismic acid, gallic acid, phenylalanine, tyrosine, tryptophan, anthranilic acid, p-hydroxybenzoic acid, p-aminobenzoic acid, phenol, and catechol from the reaction mixture.

[19] The process of the above [18], wherein the coryneform bacterium transformant is cultured under aerobic conditions where the coryneform bacterium transformant does not grow.

Advantageous Effects of Invention

Using a transformant obtained by engineering a coryneform bacterium as described above, shikimic acid can be efficiently produced from a sugar, such as glucose, at a high concentration and in good yield. Also, purification of shikimic acid is easy because, in the production, quinic acid produced as a by-product, of which separation has conventionally been a problem at the time of purification of shikimic acid, is in a limited amount.

In addition, this coryneform bacterium transformant efficiently produces organic compounds as metabolites of shikimic acid and also compounds present on the metabolic pathway from the sugar to shikimic acid.

Furthermore, the coryneform bacterium transformant exhibits an even higher productivity of organic compounds including shikimic acid when aerobic reaction is performed under conditions where the transformant does not grow.

Therefore, the present invention enables inexpensive mass production of shikimic acid or the like, which is useful as a raw material of an anti-influenza medicine.

In the present invention, it is important that a coryneform bacterium is used as a host and that a specific combination of genes achieved by artificial manipulation is used. Examples of other advantages of coryneform bacteria include the following: unlike *Escherichia coli*, coryneform bacteria do not generate endotoxin; since the reaction proceeds even under growth-limiting conditions, there is no need of adding aromatic amino acids, 4-aminobenzoic acid, 4-hydroxybenzoic acid, etc., which are generally needed for the growth of *Escherichia coli*, to the culture medium; and since the reaction of shikimic acid production proceeds under growth-limiting conditions, the sugar is used not for bacterial growth but for the production of the objective substance, resulting in high yield.

BRIEF DESCRIPTION OF DRAWING

FIG. 1 shows a metabolic pathway from sugar uptake to production of shikimic acid or the like in a coryneform bacterium.

DESCRIPTION OF EMBODIMENTS

Hereinafter, the present invention will be described in detail.

(1) Coryneform Bacterium Transformant Having Improved Shikimic Acid Production Ability The coryneform bacterium transformant of the present invention having improved shikimic acid production ability is a coryneform bacterium transformant engineered by the following (A) to (D):

(A) enhancement of 3-deoxy-D-arabino-heptulosonate-7-phosphate (DAHP) synthase activity;

(B) prevention, inhibition, or reduction of intracellular sugar uptake mediated by phosphoenolpyruvate:sugar phosphotransferase system (PTS);

(C) enhancement of intracellular sugar uptake activity mediated by a sugar transporter different from PTS and glucokinase activity; and (D) enhancement of glyceraldehyde-3-phosphate dehydrogenase (GAPDH) activity.

Enhancement of DAHP Synthase Activity

3-Deoxy-D-arabino-heptulosonate-7-phosphate (DAHP) synthase is an enzyme which produces DAHP as the first metabolite in the common pathway for biosynthesis of aromatic compounds from erythrose-4-phosphate (E4P) and phosphoenolpyruvic acid (PEP).

The DAHP synthetase activity can be enhanced by introduction of a DAHP synthase gene, or mutation introduction into or sequence substitution in the control sequence or the gene coding region of a chromosomal DAHP synthase gene of a coryneform bacterium, leading to increase in the expression amount of the gene or increase in the activity of the product of the gene.

Among these, enhancement of the DAHP synthase activity by introduction of a DAHP synthase gene is convenient and efficient.

The origin of the DAHP synthase gene to be introduced is not particularly limited, but in terms of shikimic acid productivity, a DAHP synthase gene of *Escherichia coli* is preferred.

As the DAHP synthase gene of *Escherichia coli*, the DNA consisting of the base sequence of SEQ ID NO: 1 ($aroG^{S180F}$) is preferred. This gene is a mutant gene obtained by introducing, into aroG gene, which is one of DAHP synthase genes of *Escherichia coli*, a mutation changing the serine at position 180 to phenylalanine (S180F). The present inventors have found, by comparative examinations, that the gene product thereof exhibits feedback inhibition resistance to aromatic compounds including aromatic amino acids and a high DAHP synthase activity (unpublished).

In the present invention, a DNA consisting of a base sequence which has 90% or more, in particular 95% or more, in particular 98% or more of identity with the base sequence of SEQ ID NO: 1 and which encodes a polypeptide having DAHP synthase activity can also be used.

In the present invention, the base sequence homology was calculated using GENETYX Ver. 8 (made by Genetyx).

In the present invention, a DNA which hybridizes to a DNA consisting of a complementary base sequence of SEQ ID NO: 1 under stringent conditions and which encodes a polypeptide having DAHP synthase activity can also be used.

In the present invention, "stringent conditions" means conditions in which hybridization is performed in a hybridization solution at a salt concentration of 6×SSC at 50 to 60° C. for 16 hours and then washing with a solution at a salt concentration of 0.1×SSC is performed.

In the present invention, to identify a protein encoded by a DNA as DAHP synthase, the protein encoded by the DNA is measured for DAHP synthase activity. The DAHP synthase activity is determined by adding an enzyme to be tested to a solution for testing consisting of 20 mM bis-tris propane buffer (pH 6.8), 500 μM sodium phosphoenolpyruvate (PEP), 500 μM erythrose-4-phosphate, and 1 mM manganese chloride to prepare a reaction mixture, and then measuring, as an index, the reduction in the absorbance of PEP at 232 nm (=2800/M·cm). Activity that produces 1 μmol of DAHP per minute at 28° C. is determined as 1 unit of DAHP synthase activity.

Also, in the present invention, the enhancement of the DAHP synthase activity of a coryneform bacterium transformant is confirmed by measuring the DAHP synthase activity in a cell extract of the coryneform bacterium transformant.

Prevention, Inhibition, or Reduction of Intracellular Sugar Uptake Mediated by PTS The phosphoenolpyruvate:sugar phosphotransferase system (PTS) is a sugar transport mechanism present only in prokaryotes and involved in sugar (e.g., glucose) uptake coupled to sugar phosphorylation. In *Escherichia coli* and a coryneform bacterium, PTS plays a major role in intracellular sugar uptake. PTS consists of Enzyme I (PEP protein kinase) and HPr (histidine-phosphorylatable protein), which are common components, and of Enzymes II, which is a membrane protein involved in sugar-specific transport. Using phosphoenolpyruvate (PEP) from the glycolytic system as a phosphate donor, PTS converts sugars, through phosphorelay between these components, into their phosphorylated forms and transports them into cells. However, in association with the intracellular transport of glucose, PTS consumes PEP, which is one of the common precursors of aromatic compounds including shikimic acid. Therefore, for higher production of aromatic compounds including shikimic acid, it is preferred to use a glucose transport system which is different from PTS and which does not consume PEP.

The PTS-mediated intracellular sugar uptake can be prevented, inhibited, or reduced by disruption, deletion, or mutation of genes encoding PTS on the chromosome of a coryneform bacterium.

When one or more of the gene encoding Enzyme I, the gene encoding Hpr, and the gene encoding Enzyme II are disrupted, deleted, or mutated, the purpose is achieved, and it is preferred that the gene encoding the Hpr protein, which is a common component in PTS, is disrupted, deleted, or mutated.

Examples of the genes encoding PTS involved in glucose transport include ptsI encoding Enzyme I, ptsH encoding Hpr, ptsG encoding Enzyme II, etc. When one or more of these genes are disrupted, deleted, or mutated, the purpose is achieved, and it is preferred that the ptsH gene encoding the Hpr protein, which is a common component in PTS, is disrupted, deleted, or mutated.

Replacement of a gene on the chromosome with the corresponding gene having a disruption or deletion can be achieved by creating a gene with deletion mutation for not producing a normally functioning protein, and transforming a bacterium with a DNA comprising the mutated gene for homologous recombination between the gene on the chromosome and the mutated gene. A protein encoded by a gene having a disruption or deletion, even when produced, has a conformation different from that of the wild type, and has no or reduced function. The gene deletion or gene disruption by way of gene substitution through the use of homologous recombination has already been established, and examples thereof include a method using a plasmid containing a temperature sensitive replication origin or a plasmid capable of conjugal transfer, and a method using a suicide vector not having a replication origin in a host (U.S. Pat. No. 6,303,383, JP 05-007491 A).

In the present invention, the prevention, inhibition, or reduction of the PTS-mediated sugar transport activity of a coryneform bacterium transformant is confirmed based on the fact that the growth of the transformant using, as carbon source, the sugar (glucose, sucrose, fructose, etc.) transported by PTS is prevented, inhibited, or reduced and on the fact that introducing a normal pts gene restores the phenotype to normal.

Enhancement of Sugar Uptake Activity Mediated by Sugar Transport System Different from PTS It is known that, in *Corynebacterium glutamicum*, there exists a glucose transport system which is different from PTS (non-PTS glucose permease) and which does not consume PEP for sugar uptake. A *Corynebacterium glutamicum* strain of which the pts gene is disrupted and PTS-mediated sugar uptake is inhibited exhibits no or little growth on glucose as a single carbon source, but higher expression of non-PTS glucose permease in the strain restores the ability of the strain growing on glucose as a single carbon source. (Ikeda, M., et al., Identification and application of a different glucose uptake system that functions as an alternative to the phosphotransferase system in *Corynebacterium glutamicum*. Appl. Microbiol. Biotechnol. 90: 1443-1451, Lindner, S. N., et al., Phosphotransferase system-independent glucose utilization, in *Corynebacterium glutamicum* by inositol permeases and glucokinases. Appl. Environ. Microbiol. 77: 3571-3581.)

In the present invention, it is preferred that intracellular glucose uptake and bacterial growth on glucose as a single carbon source are improved by the enhancement of the non-PTS glucose permease activity, which does not consume PEP in association with sugar uptake in a *Corynebacterium glutamicum* strain in which PTS-mediated sugar transport is blocked. As a result of the blocking and the enhancement, the consumption of PEP in association with glucose transport can be avoided, and more PEP can be provided for the biosynthesis of aromatic compounds, such as shikimic acid.

The intracellular glucose uptake depending on non-PTS glucose permease can be enhanced by introduction of a gene encoding a non-PTS glucose permease, or mutation introduction into or base sequence substitution in (the control sequence or the gene coding region of) a chromosomal non-PTS glucose permease gene of a coryneform bacterium, leading to increase in the expression amount of the gene or increase in the activity of the product of the gene.

Among these, enhancement of the glucose uptake activity by introduction of a non-PTS glucose permease gene is convenient and efficient.

The origin of the non-PTS glucose permease gene to be introduced is not particularly limited, but in terms of shikimic acid productivity, the genus *Corynebacterium*, in particular, *Corynebacterium glutamicum* is preferred.

The non-PTS glucose permease may be of any type as long as it can function in a coryneform bacterium, and examples thereof include inositol transporters of *Corynebacterium glutamicum* (iolT1, iolT2), galactose permease of *Escherichia coli* (galP), and glucose facilitator of *Zymomonas mobilis* (glf). Particularly, for better efficiency in the production of shikimic acid, preferred is that the sugar uptake activity mediated by an inositol transporter of *Corynebacterium glutamicum* is enhanced.

Examples of the inositol transporter gene of *Corynebacterium glutamicum* include the DNA consisting of the base sequence of SEQ ID NO: 2 (iolT1).

In the present invention, a DNA consisting of a base sequence which has 90% or more, in particular 95% or more, in particular 98% or more of identity with the base sequence of SEQ ID NO: 2 and which encodes a polypeptide having inositol transporter activity can also be used.

In the present invention, a DNA which hybridizes to a DNA consisting of a complementary base sequence of SEQ ID NO: 2 under stringent conditions and which encodes a polypeptide having inositol transporter activity can also be used.

In the present invention, a protein encoded by a DNA is identified as a non-PTS glucose permease based on the facts, as indicators, that a transformant produced by introducing the DNA into a host cell for expression of the DNA in the cell, the host cell having lost its PTS-dependent glucose transport ability as a result of ptsH gene disruption or the like and showing reduced growth using glucose as a carbon source, can grow or consume glucose in an enhanced manner as compared to the cell before the transformation and that the effect is not affected by inhibition of PTS-dependent sugar transport by, for example, disruption of a pts gene.

Also, in the present invention, the enhancement of the non-PTS glucose permease activity of a coryneform bacterium transformant is confirmed by the fact, as an indicator, that the transformant can grow using glucose as a carbon source or consume glucose in an enhanced manner as compared to the strain before the gene introduction, i.e., the host cell having lost its PTS-dependent glucose transport ability as a result of ptsH gene disruption or the like.

Enhancement of Glucokinase Activity

Glucose transported into cells by non-PTS glucose permease is not phosphorylated and differs on this point from glucose transported by PTS. Therefore, in order for the glucose transported into cells by non-PTS glucose permease to be metabolized in the glycolytic system, it needs to be first converted to glucose-6-phosphate by glucokinase activity. Glucokinase is an enzyme that catalyzes the conversion from glucose to glucose-6-phosphate.

In the present invention, along with the enhancement of glucose transport depending on non-PTS glucose permease, glucokinase activity is also enhanced. As a result, the present invention is characterized in that intracellular uptake of glucose and subsequent sugar metabolism in the glycolytic system and in the pentose phosphate pathway are promoted.

The glucokinase activity can be enhanced by introduction of a glucokinase gene for enhancement of the expression thereof, or mutation introduction into or sequence substitution (in the control sequence or in the gene coding region) of a chromosomal glucokinase gene of a coryneform bacterium, leading to increase in the expression amount of the gene or increase in the activity of the product of the gene.

On the chromosome of *Corynebacterium glutamicum* R, there exist at least three kinds of glucokinase genes, namely cgR_2067 (glk1), cgR_2552 (glk2), and cgR_1739 (ppgK). Among these, cgR_2067 (glk1) and cgR_2552 (glk2) have high homology with a glucokinase which uses ATP as a good substrate, and cgR_1739 (ppgK) has high homology with a glucokinase which uses polyphosphoric acid as a good substrate. In the present invention, preferred is that one or more kinds of these glucokinase genes are enhanced, and more preferred is that all of the three kinds are enhanced.

The enhancement of the glucokinase activity by introduction of the glucokinase gene is convenient and efficient.

The origin of the glucokinase gene to be introduced is not particularly limited, but in terms of shikimic acid productivity, the genus *Corynebacterium*, in particular, *Corynebacterium glutamicum* is preferred.

Examples of the glucokinase gene of *Corynebacterium glutamicum* include the DNA consisting of the base sequence of SEQ ID NO: 3, 4, or 5 (corresponding to glk1, glk2, or ppgK).

In the present invention, a DNA consisting of a base sequence which has 90% or more, in particular 95% or more, in particular 98% or more of identity with the base sequence of SEQ ID NO: 3, 4, or 5 and which encodes a polypeptide having glucokinase activity can also be used.

In the present invention, a DNA which hybridizes to a DNA consisting of a complementary base sequence of SEQ ID NO: 3, 4, or 5 under stringent conditions and which encodes a polypeptide having glucokinase activity can also be used.

In the present invention, to identify a protein encoded by a DNA as glucokinase, the protein encoded by the DNA is measured for glucokinase activity. For the measurement of glucokinase activity, an enzyme solution to be tested is added to a mixture for reaction consisting of a 100 mM tris-HCl buffer (pH 7.5), 4 mM magnesium chloride, 1 mM ATP, 0.2 mM NADP$^+$, 20 mM glucose, and 1 U glucose-6-phosphate dehydrogenase at 33° C. to allow the reaction to start, and the absorbance at 340 nm showing the production of NADPH (=6220/M·cm) is monitored with a Beckman DU800 spectrophotometer (made by Beckman Coulter). Activity that produces 1 μmol of NADPH per minute at 33° C. is determined as 1 unit of glucokinase activity.

Also, in the present invention, the enhancement of the glucokinase activity of a coryneform bacterium transformant is confirmed by measuring the glucokinase activity in a cell extract of the coryneform bacterium transformant.

Enhancement of GAPDH Activity

Glyceraldehyde 3-phosphate dehydrogenase (GAPDH) is an enzyme that converts glyceraldehyde-3-phosphate into 1,3-bisphosphoglycerate. In the coryneform bacterium transformant of the present invention, the GAPDH activity is enhanced.

In the present invention, a coryneform bacterium transformant in which a pts gene was disrupted and the non-PTS glucose permease-mediated glucose intake and the glucokinase activity were enhanced exhibited significant accumulation of dihydroxyacetone (DHA), a metabolite produced by dephosphorization of dihydroxyacetone phosphate as a metabolic intermediate in the glycolytic system. Also, in the coryneform bacterium transformant, the intracellular concentrations of glyceraldehyde-3-phosphate and other upstream metabolic intermediates in the glycolytic pathway were remarkably increased. It was assumed that the reaction step catalyzed by GAPDH was the rate-limiting step of the glycolytic metabolism-dependent sugar consumption activity in the coryneform bacterium transformant, and resulting overflow metabolism caused the DHA accumulation.

Therefore, the present invention is characterized in that enhanced GAPDH activity in the coryneform bacterium transformant releases the rate limitation in the glycolysis to promote sugar consumption and to improve shikimic acid-production ability.

The group of present inventors found that, in matter production under oxygen deprivation conditions by a coryneform bacterium, the GAPDH activity is inhibited by NADH, which accumulates specifically in oxygen deprivation conditions, and sugar consumption mediated by the glycolytic system is inhibited (Inui, M. et. al., Metabolic analysis of *Corynebacterium glutamicum* during lactate and succinate productions under oxygen deprivation conditions. J. Mol. Microbiol. Biotechnol. 7: 182-196 (2004)). However, it has not been known that enhancement of the GAPDH activity in aerobic conditions, where NADH concentration is kept relatively low, activates sugar consumption, leading to higher production of the objective product.

The present invention is characterized in that, even under aerobic conditions, where NADH concentration is kept relatively low, enhancement of the GAPDH activity in a coryneform bacterium transformant depending on enhanced non-PTS glucose permease dependent sugar transport remarkably increases sugar metabolism activity, leading to higher production of the objective compound.

The GAPDH activity can be enhanced by introduction of a GAPDH gene for enhancement of the expression thereof, or mutation introduction into or sequence substitution (in the control sequence or in the gene coding region) of a chromosomal GAPDH gene of a coryneform bacterium, leading to increase in the expression amount of the gene or increase in the activity of the product of the gene.

Among these, enhancement of the GAPDH activity by introduction of the GAPDH gene is convenient and efficient.

The origin of the GAPDH gene to be introduced is not particularly limited, but in terms of shikimic acid productivity, the genus *Corynebacterium*, in particular, *Corynebacterium glutamicum* is preferred.

Examples of the GAPDH gene of *Corynebacterium glutamicum* include the DNA consisting of the base sequence of SEQ ID NO: 6 (gapA).

In the present invention, a DNA consisting of a base sequence which has 90% or more, in particular 95% or more, in particular 98% or more of identity with the base sequence of SEQ ID NO: 6 and which encodes a polypeptide having GAPDH activity can also be used.

In the present invention, a DNA which hybridizes to a DNA consisting of a complementary base sequence of SEQ ID NO: 6 under stringent conditions and which encodes a polypeptide having GAPDH activity can also be used.

In the present invention, to identify a protein encoded by a DNA as GAPDH, the polypeptide encoded by the DNA is measured for GAPDH activity. For the measurement of the GAPDH activity, an enzyme solution to be tested is added to a mixture for reaction consisting of a 25 mM phosphate buffer (pH 7.5), 25 mM triethanolamine (pH 7.5), 0.2 mM EDTA, 5 mM NAD$^+$, and 5 mM glyceraldehyde-3-phosphate at 33° C. to allow the reaction to start, and the absorbance at 340 nm showing the production of NADH (=6220/M·cm) is monitored with a Beckman DU800 spectrophotometer (made by Beckman Coulter). Activity that produces 1 μmol of NADH per minute at 33° C. is determined as 1 unit of GAPDH activity.

Also, in the present invention, the enhancement of the GAPDH activity of a coryneform bacterium transformant is confirmed by measuring the GAPDH activity in a cell extract of the coryneform bacterium transformant.

Prevention, Inhibition, or Reduction of Dihydroxyacetone Phosphate (DHAP) Phosphatase Activity DHAP phosphatase is an enzyme that catalyzes the dephosphorization of DHAP, i.e., the conversion of DHAP to dihydroxyacetone (DHA).

In the coryneform bacterium of the present invention, the DHAP phosphatase activity is preferably prevented, inhibited, or reduced. As described above, the shikimic acid producing strain of a coryneform bacterium which depends for intracellular sugar uptake on highly expressed non-PTS glucose permease and glucokinase highly produces DHA as a by-product. Therefore, it is thought that, by blocking the pathway, more carbon can be supplied for the production of aromatic compounds, such as shikimic acid.

*Corynebacterium glutamicum* has HAD (haloacid dehalogenase) super family phosphatase (HdpA) as an enzyme that catalyzes the dephosphorization of DHAP. The DHAP phosphatase activity of *Corynebacterium glutamicum* can be prevented, inhibited, or reduced by disruption, deletion, or mutation of the DHAP phosphatase gene (hdpA) on the chromosome.

In the present invention, the prevention, inhibition, or reduction of the DHAP phosphatase activity of a coryneform bacterium transformant is confirmed by measuring the DHAP phosphatase activity in a cell extract of the coryneform bacterium transformant. For the measurement of the DHAP phosphatase activity, an enzyme solution to be tested is added to a mixture for reaction consisting of a 100 mM tris-malate buffer (pH 7.5), 5 mM magnesium sulfate, and 5 mM DAHP at 33° C. to allow the reaction to start, and inorganic phosphate ions released from DHAP were quantified by a known colorimetry method (Gawronski, J. D., et al., Microtiter assay for glutamine synthetase biosynthetic activity using inorganic phosphate detection. Anal. Biochem. 327: 114-118 (2004)). Anal. Biochem. 327: 114-118 (2004)). In the cases where the quantitative value decreases or turns to zero, the dihydroxyacetone phosphate phosphatase activity is judged to have been prevented, inhibited or reduced.

Enhancement of 3-Dehydroquinic Acid (3-DHQ) Synthase Activity, 3-DHQ Dehydratase Activity, and Shikimate Dehydrogenase Activity 3-Deoxy-D-arabino-heptulosonate-7-phosphate (DAHP) as the first metabolite in the common pathway for biosynthesis of aromatic compounds is produced by condensation of PEP and E4P. DAHP is further converted into shikimic acid through continuous reactions by 3-DHQ synthase, 3-DHQ dehydratase, and shikimate dehydrogenase. 3-DHQ synthase is an enzyme which catalyzes the conversion from DAHP to 3-dehydroquinic acid, 3-DHQ dehydratase is an enzyme which catalyzes the conversion from 3-DHQ to 3-DHS, and shikimate dehydrogenase is an enzyme which catalyzes the conversion from 3-DHS to shikimic acid. In the present invention, by enhancing these enzyme activities, the carbon flow from DAHP to shikimic acid can be enhanced, and thereby the productivity of objective aromatic compounds, such as shikimic acid, can be improved.

In the coryneform bacterium of the present invention, preferred is that one or more of these enzyme activities are enhanced, and more preferred is that all of the activities are enhanced.

The 3-DHQ synthase activity, the 3-DHQ dehydratase activity, and the shikimate dehydrogenase activity can be enhanced by introduction of the gene encoding each enzyme, or mutation introduction into or sequence substitution in the control sequence or in the gene coding region of the chromosomal gene of a coryneform bacterium encoding each enzyme, leading to increase in the expression amount of the gene or increase in the activity of the product of the gene. Among these, enhancement of the enzyme activity by introduction of the enzyme gene is convenient and efficient.

The origin of each enzyme gene to be introduced is not particularly limited, but in terms of shikimic acid productivity, the genus *Corynebacterium*, in particular, *Corynebacterium glutamicum* is preferred.

Examples of the 3-DHQ synthase gene of *Corynebacterium glutamicum* include the DNA consisting of the base sequence of SEQ ID NO: 7 (aroB), examples of the 3-DHQ dehydratase gene include the DNA consisting of the base sequence of SEQ ID NO: 8 (aroD), and examples of the shikimate dehydrogenase gene include the DNA consisting of the base sequence of SEQ ID NO: 9 (aroE).

In the present invention, a DNA consisting of a base sequence which has 90% or more, in particular 95% or more, in particular 98% or more of identity with the base sequence of SEQ ID NO: 7, 8, or 9 and which encodes a polypeptide having 3-DHQ synthase activity, 3-DHQ dehydratase activity, or shikimate dehydrogenase activity can also be used.

In the present invention, a DNA which hybridizes to a DNA consisting of a complementary base sequence of SEQ ID NO: 7, 8, or 9 under stringent conditions and which encodes a polypeptide having 3-DHQ synthase activity, 3-DHQ dehydratase activity, or shikimate dehydrogenase activity can also be used.

In the present invention, to identify a protein encoded by a DNA as 3-DHQ synthase, the protein encoded by the DNA is measured for 3-DHQ synthase activity. The 3-DHQ synthase activity is measured by a known method (Meudi, S. et al., Dehydroquinate synthase from *Escherichia coli*, and its substrate 3-deoxy-D-arabino-heptulosonic acid 7-phosphate. Methods. Enzymol. 142: 306-314 (1987)). At 33° C., an enzyme solution to be tested is added to a mixture for reaction consisting of a 50 mM potassium phosphate buffer (pH 7.0), 0.2 mM DAHP, 0.2 mM NAD$^+$, 1 mM Cobalt(II) chloride.6H$_2$O, and a crude enzyme solution of 3-DHQ dehydratase to allow the reaction to start, and the absorbance at 234 nm showing the production of 3-DHS (=12000/M·cm) by the coupling reaction with 3-DHQ dehydratase is monitored with a Beckman DU800 spectrophotometer (made by Beckman Coulter). Activity that produces 1 μmol of 3-DHQ per minute at 33° C. is determined as 1 unit of 3-DHQ synthase activity.

Also, in the present invention, the enhancement of the 3-DHQ synthase activity of a coryneform bacterium transformant is confirmed by measuring the 3-DHQ synthase activity in a cell extract of the coryneform bacterium transformant.

In the present invention, to identify a protein encoded by a DNA as 3-DHQ dehydratase, the protein encoded by the DNA is measured for 3-DHQ dehydratase activity. The 3-DHQ dehydratase activity is measured by a known method (Chaudhuri, S. et al., 3-Dehydroquinate dehydratase from *Escherichia coli*. Methods. Enzymol. 142: 320-324 (1987)). At 33° C., an enzyme solution to be tested is added to a mixture for reaction consisting of a 50 mM potassium phosphate buffer (pH 7.0) and 0.5 mM 3-DHQ to allow the reaction to start, and the absorbance at 234 nm showing the production of 3-DHS (=12000/M·cm) is monitored with a Beckman DU800 spectrophotometer (made by Beckman Coulter). Activity that produces 1 μmol of 3-DHS per minute at 33° C. is determined as 1 unit of 3-DHQ dehydratase activity.

Also, in the present invention, the enhancement of the 3-DHQ dehydratase activity of a coryneform bacterium transformant is confirmed by measuring the 3-DHQ dehydratase activity in a cell extract of the coryneform bacterium transformant.

In the present invention, to identify a protein encoded by a DNA as shikimate dehydrogenase, the protein encoded by the DNA is measured for shikimate dehydrogenase activity. The shikimate dehydrogenase activity is measured by a known method (Chaudhuri, S. et al., Shikimate dehydratase from *Escherichia coli*. Methods. Enzymol. 142: 315-320 (1987)). At 33° C., an enzyme solution to be tested is added to a mixture for reaction consisting of a 100 mM tris-HCl buffer (pH 7.5), 0.2 mM NADPH, and 0.5 mM 3-dehydroshikimic acid to allow the reaction to start, and the decrease in the absorbance at 340 nm in association with the consumption of NADPH (=6220/M·cm) is monitored with a Beckman DU800 spectrophotometer (made by Beckman Coulter). Activity that produces 1 μmol of shikimic acid per minute at 33° C. is determined as 1 unit of shikimate dehydrogenase activity.

Also, in the present invention, the enhancement of the shikimate dehydrogenase activity of a coryneform bacterium transformant is confirmed by measuring the shikimate dehydrogenase activity in a cell extract of the coryneform bacterium transformant.

Enhancement of Transketolase Activity and Transaldolase Activity

In sugar metabolism, transketolase catalyzes two types of reactions. In the non-oxidative pentose phosphate pathway, transketolase catalyzes, as the first type of reactions, the conversion from D-xylulose-5-phosphate (X5P) to glyceraldehyde-3-phosphate (GAP) and the conversion from D-ribose-5-phosphate (R5P) to sedoheptulose-7-phosphate (S7P). These reactions are reversible and conjugated. Also, transketolase catalyzes, as the second type of reactions, the conversion from D-fructose-6-phosphate (F6P) to erythrose-4-phosphate (E4P) and the conversion from GAP to X5P. These reactions are reversible and conjugated.

Also, in sugar metabolism, transaldolase catalyzes the conversion from GAP to E4P, and the conversion from S7P to F6P. These reactions are conjugated.

Thus, transketolase and transaldolase are involved in the production of E4P, which is one of the precursors of aromatic compound biosynthesis. It is expected that enhancement of these enzyme activities increases intracellularly supplied E4P and thereby improves the productivity of aromatic compounds, such as shikimic acid.

In the coryneform bacterium of the present invention, preferred is that either of the enzyme activities is enhanced, and more preferred is that both the activities are enhanced.

The transketolase activity and the transaldolase activity can be enhanced by introduction of each enzyme gene for enhancement of the expression thereof, or mutation introduction into or sequence substitution in (the control sequence or the gene coding region of) each enzyme gene on the chromosome of a coryneform bacterium, leading to increase in the expression amount of the gene or increase in the activity of the product of the gene. Among these, enhancement of the enzyme activity by introduction of each enzyme gene is convenient and efficient.

The origin of each enzyme gene to be introduced is not particularly limited, but in terms of shikimic acid productivity, the genus *Corynebacterium*, in particular, *Corynebacterium glutamicum* is preferred.

Examples of the transketolase gene of *Corynebacterium glutamicum* include the DNA consisting of the base sequence of SEQ ID NO: 10 (tkt), and examples of the transaldolase gene of *Corynebacterium glutamicum* include the DNA consisting of the base sequence of SEQ ID NO: 11 (tal).

In the present invention, a DNA consisting of a base sequence which has 90% or more, in particular 95% or more, in particular 98% or more of identity with the base sequence of SEQ ID NO: 10 or 11 and which encodes a polypeptide having transketolase activity or transaldolase activity can also be used.

In the present invention, a DNA which hybridizes to a DNA consisting of a complementary base sequence of SEQ ID NO: 10 or 11 under stringent conditions and which encodes a polypeptide having transketolase activity or transaldolase activity can also be used.

In the present invention, to identify a protein encoded by a DNA as transketolase, the protein encoded by the DNA is measured for transketolase activity. The transketolase activity is measured by a known method (Ikeda, M. et al., Cloning of the transketolase gene and the effect of its dosage on aromatic amino acid production in *Corynebacterium glutamicum*. Appl. Microbiol. Biotechnol. 51: 201-206 (1999)), and in the cases where the transketolase activity is detected, the protein is judged to be transketolase.

Also, in the present invention, the enhancement of the transketolase activity of a coryneform bacterium transformant is confirmed by measuring the transketolase activity in a cell extract of the coryneform bacterium transformant.

In the present invention, to identify a protein encoded by a DNA as transaldolase, the protein encoded by the DNA is measured for transaldolase activity. The transaldolase activity is measured by a known method (Lu, J L. et al., Metabolic engineering and control analysis for production of aromatics: Role of transaldolase, Biotechnol. Bioeng. 53: 132-138 (1997)).

Also, in the present invention, the enhancement of the transaldolase activity of a coryneform bacterium transformant is confirmed by measuring the transaldolase activity in a cell extract of the coryneform bacterium transformant.

Prevention, Inhibition, or Reduction of Shikimate Kinase Activity, 3-Dehydroshikimate (3-DHS) Dehydratase Activity, and Quinate/Shikimate Dehydrogenase Activity Shikimate kinase is an enzyme which catalyzes, in the common pathway for biosynthesis of aromatic compounds, the conversion from shikimic acid to shikimate-3-phosphate, 3-dehydroshikimic acid dehydratase is an enzyme which catalyzes the conversion from 3-dehydroshikimic acid to protocatechuic acid, and quinate/shikimate dehydrogenase is an enzyme which mainly catalyzes the conversion from shikimic acid to 3-dehydroshikimic acid.

In the coryneform bacterium of the present invention, preferred is that one or more of the enzyme activities are prevented, inhibited, or reduced, and more preferred is that all of these activities are prevented, inhibited, or reduced. The activity of each of these enzymes can be prevented, inhibited, or reduced by disruption, deletion, or mutation of each enzyme gene on the chromosome of a coryneform bacterium.

In the present invention, the prevention, inhibition, or reduction of the shikimate kinase activity of a coryneform bacterium transformant is confirmed by measuring the shikimate kinase activity in a cell extract of the coryneform bacterium transformant. The shikimate kinase activity is measured by a known method (Feyter, R D. et al., Shikimate kinases from *Escherichia coli* K12. Methods. Enzymol. 142: 355-361 (1987)), and in the cases where the measured value decreases or turns to zero, the shikimate kinase activity is judged to have been reduced, inhibited, or prevented.

Also, the prevention, inhibition, or reduction of the 3-DHS dehydratase activity of a coryneform bacterium transformant is confirmed by measuring the 3-DHS dehydratase activity in a cell extract of the coryneform bacterium transformant. The 3-DHS dehydratase activity is measured by a known method (Stroman, P. et al., Purification and characterization of 3-dehydroshikimate dehydratase, an enzyme in the inducible quinic acid catabolic pathway of *Neurospora crassa*. J. Biol. Chem. 253: 4593-4598 (1978)), and in the cases where the measured value decreases or turns to zero, the 3-DHS dehydratase activity is judged to have been reduced, inhibited, or prevented.

Also, the prevention, inhibition, or reduction of the quinate/shikimate dehydrogenase activity of a coryneform bacterium transformant is confirmed by measuring the quinate/shikimate dehydrogenase activity in a cell extract of the coryneform bacterium transformant. The quinate/shikimate dehydrogenase activity is measured by a known method (Kubota, T. et al., Characterization of shikimate dehydrogenase homologs of *Corynebacterium glutamicum*. Appl. Microbial. Biotechnol. 97: 8139-8149 (2013)), and in the cases where the measured value decreases or turns to zero, the quinate/shikimate dehydrogenase activity is judged to have been reduced, inhibited, or prevented.

Coryneform Bacteria

The coryneform bacteria are a group of microorganisms defined in Bergey's Manual of Determinative Bacteriology, Vol. 8, 599 (1974), and are not particularly limited as long as they grow under normal aerobic conditions.

The specific examples include the genus *Corynebacterium*, the genus *Brevibacterium*, the genus *Arthrobacter*, the genus *Mycobacterium* and the genus *Micrococcus*. Among the coryneform bacteria, the genus *Corynebacterium* is preferred as the host microorganism of the present invention.

Examples of the genus *Corynebacterium* include *Corynebacterium glutamicum*, *Corynebacterium efficiens*, *Corynebacterium ammoniagenes*, *Corynebacterium halotolerance*, and *Corynebacterium alkanolyticum*.

Among them, *Corynebacterium glutamicum* is preferred as the host microorganism of the present invention for safety and high shikimic acid production. Examples of preferred strains include *Corynebacterium glutamicum* R (FERM BP-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), and MJ-233AB-41 (FERM BP-1498). These strains are deposited internationally under the Budapest Treaty and available to the public. Among them, strains R (FERMBP-18976), ATCC13032, and ATCC13869 are preferred.

According to molecular biological classification, names of some species of coryneform bacteria, such as *Brevibacterium flavum*, *Brevibacterium lactofermentum*, *Brevibacterium divaricatum*, and *Corynebacterium lilium* are standardized to *Corynebacterium glutamicum* (Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int. J. Syst. Bacteriol. 41:255-260. (1991); and Kazuo Komagata et al., "Classification of the coryneform group of bacteria", Fermentation and industry, 45:944-963 (1987)).

Examples of the genus *Brevibacterium* include *Brevibacterium ammoniagenes* (for example, ATCC6872). The strain is deposited internationally under the Budapest Treaty and available to the public.

Examples of the genus *Arthrobacter* include *Arthrobacter globiformis* (for example, ATCC8010, ATCC4336, ATCC21056, ATCC31250, ATCC31738 and ATCC35698). These strains are deposited internationally under the Budapest Treaty and available to the public.

Examples of the genus *Mycobacterium* include *Mycobacterium bovis* (for example, ATCC19210 and ATCC27289). These strains are deposited internationally under the Budapest Treaty and available to the public.

Examples of the genus *Micrococcus* include *Micrococcus freudenreichii* (for example, NO. 239 (FERM P-13221)), *Micrococcus leuteus* (for example, NO. 240 (FERM P-13222)), *Micrococcus ureae* (for example, IAM1010), and *Micrococcus roseus* (for example, IFO3764).

The coryneform bacterium described above may be further engineered, and may be, for example, a disruptant in which a gene of lactate dehydrogenase (ldh), phosphoenolpyruvate carboxylase (ppc), or malate dehydrogenase (mdh) is disrupted. Among them, preferred is a disruptant in which a lactate dehydrogenase gene is disrupted. In the disruptant, the lactate dehydrogenase gene is disrupted and the metabolic pathway from pyruvic acid to lactic acid is blocked. Particularly preferred is a disruptant of *Corynebacterium glutamicum*, especially the R (FERM BP-18976) strain in which the lactate dehydrogenase gene is disrupted.

Such a disruptant can be prepared based on a conventional gene engineering process. Such a lactate dehydrogenase gene disruptant and the preparation process thereof are described in WO 2005/010182 A1, for example.

Pentose Utilizing Ability

A wild-type strain of a coryneform bacterium is usually incapable of utilizing pentoses, such as D-xylose and L-arabinose, but the coryneform bacterium of the present invention is preferably capable of utilizing D-glucose and pentoses (one or more of D-xylose and L-arabinose, for example) in parallel, and more preferably capable of simultaneous parallel utilization thereof to produce an organic compound, such as shikimic acid, from a pentose also. Generally, in the presence of glucose, a microorganism preferentially consumes glucose even if other sugars coexist. However, when a microorganism has an ability of utilizing D-glucose and a pentose in parallel, the microorganism is capable of simultaneously consuming glucose and a pentose under conditions where both sugars coexist, and as a result, the time needed for the production of the objective substance can be reduced.

D-Xylose Utilizing Ability

Examples of the method of providing a coryneform bacterium with D-xylose utilizing ability include a method in which a D-xylose metabolism-related gene of another species is transferred into a coryneform bacterium.

The metabolism from D-xylose to D-xylulose-5-phosphate in procaryotes and some kinds of fungi is performed in two steps catalyzed by two enzymes, xylose isomerase (xylA) that catalyzes a reaction from D-xylose to D-xylulose and xylulokinase (xylB) that catalyzes a reaction from D-xylulose to D-xylulose-5-phosphate. By introducing genes encoding these enzymes into a coryneform bacterium, the coryneform bacterium is provided with D-xylose utilizing ability.

For example, the inventors have already disclosed a technology for providing a coryneform bacterium with a D-xylose-utilizing ability by transferring a xylA gene and a xylB gene of *Escherichia coli* as D-xylose metabolism-related genes, and allowing them to be expressed (Appl. Environ. Microbiol., Vol. 72, 3418-3428 (2006)). In the present invention also, a coryneform bacterium can be provided with D-xylose utilizing ability by the introduction of the xylA gene and the xylB gene of various organism species including *Escherichia coli* thereinto.

The xylA gene and the xylB gene are usually carried by microorganisms capable of metabolizing D-xylose. Preferably, each of the xylA gene and the xylB gene is from a microorganism independently selected from the group consisting of *Escherichia coli*, *Corynebacterium glutamicum* (having a xylB gene only), *Bacillus subtilis*, *Salmonella typhimurium*, *Bacillus halodurans*, *Sinorhizobium meliloti*, and *Agrobacterium tumefaciens*. More preferred are the xylA gene and the xylB gene of *Escherichia coli*.

Arabinose Utilizing Ability

By introducing a gene encoding L-arabinose isomerase (araA), a gene encoding L-ribulokinase (araB), and a gene encoding L-ribulose-5-phosphate-4-epimerase (araD) into a coryneform bacterium, the coryneform bacterium can be provided with arabinose utilizing ability.

These genes are carried by microorganisms capable of metabolizing L-arabinose. For example, araA, aeaB, and araD of *Escherichia coli*, *Corynebacterium glutamicum* ATCC31831, *Bacillus subtilis*, *Salmonella typhimurium*, *Bacillus halodurans*, *Geobacillus stearothermophilus*, or *Mycobacterium smegmatis* may be used.

Also, by introducing a gene encoding a proton symporter of an L-arabinose transport system (L-arabinose transport system proton symporter) (araE), the arabinose uptake ability can be improved, and as a result, the arabinose utilizing ability can be further improved. The araE gene sequence and enzymatic characteristics in the following bacterial strains etc. are reported: *Bacillus subtilis* (J. Bacteriol., Vol. 179, 7705-7711 (1997)), *Klebsiella oxytoca*8017 (J. Bacteriol., Vol. 177, 5379-5380 (1995)), and *Escherichia coli* (J. Biol. Chem., Vol. 263, 8003-8010 (1988)). In the present invention, an araE gene of *Corynebacterium glutamicum* ATCC31831, *Escherichia coli*, *Bacillus subtilis*, *Klebsiella oxytoca*, or *Salmonella typhimurium* is preferably used.

The introduction of the L-arabinose proton symporter gene improves not only the L-arabinose uptake ability but also the D-xylose uptake ability, and as a result, also further improves the D-xylose utilizing ability.

Cellobiose Utilizing Ability

The coryneform bacterium of the present invention preferably has an improved cellobiose utilizing ability, so that the coryneform bacterium is capable of producing an organic compound, such as shikimic acid, from cellobiose also.

The cellobiose utilizing ability can be obtained by, for example, the method described in JP 2004-089029 A, i.e., introducing a mutation into a coryneform bacterium and selecting a strain growing on a medium containing cellobiose as an only carbon source. Examples of a strain obtained in this way include FERM P-18977 and FERM P-18978 (JP 2004-089029 A). Also, examples of an artificially obtained recombinant strain capable of utilizing cellobiose include FERM P-18979 (JP 2004-089029 A).

Construction of Vector for Gene Introduction

When gene introduction is performed to enhance the activity of a protein or an enzyme encoded by the gene, the DNA corresponding to the gene may be integrated into the chromosome of a host or be cloned into a suitable vector replicable in a host and then introduced into the host.

The plasmid vector may be any plasmid vector as long as it comprises a gene responsible for autonomously replicating function in a coryneform bacterium. Specific examples of the plasmid vector include pAM330 of *Brevibacterium lactofermentum* 2256 (JP 58-67696 A; Miwa, K. et al., Cryptic plasmids in glutamic acid-producing bacteria. Agric. Biol. Chem. 48: 2901-2903 (1984); and Yamaguchi, R. et al., Determination of the complete nucleotide sequence of the *Brevibacterium lactofermentum* plasmid pAM 330 and the analysis of its genetic information. Nucleic Acids Symp. Ser.

16: 265-267 (1985)), pHM1519 of *Corynebacterium glutamicum* ATCC3058 (Miwa, K. et al., Cryptic plasmids in glutamic acid-producing bacteria. Agric. Biol. Chem. 48:2901-2903 (1984)), pCRY30 of the same *Corynebacterium glutamicum* ATCC3058 (Kurusu, Y. et al., Identification of plasmid partition function in coryneform bacteria. Appl. Environ. Microbiol. 57: 759-764 (1991)), pCG4 of *Corynebacterium glutamicum* T250 (JP 57-183799 A; and Katsumata, R. et al., Protoplast transformation of glutamate-producing bacteria with plasmid DNA. J. Bacteriol., 159: 306-311 (1984)), pAG1, pAG3, pAG14, and pAG50 of the same *Corynebacterium glutamicum* T250 (JP 62-166890 A), pEKO, pEC5, and pEKEx1 of the same *Corynebacterium glutamicum* T250 (Eikmanns, B. J. et al., A family of *Corynebacterium glutamicum/Escherichia coli* shuttle vectors for cloning, controlled, gene expression, and promoter probing. Gene, 102: 93-98 (1991)), etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are of *Corynebacterium glutamicum* R, and inter alia, PgapA is preferred.

Examples of a preferred terminator include terminator rrnB T1T2 of *Escherichia coli* rRNA operon, terminator trpA of *Escherichia coli*, and terminator trp of *Brevibacterium lactofermentum*, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and electroporation. Among them, preferred for a coryneform bacterium is electroporation, which can be performed by a known method (Kurusu, Y. et al., Electroporation-transformation system for Coryneform bacteria by auxotrophic complementation, Agric. Biol. Chem. 54: 443-447 (1990)).

The transformant is cultured using a culture medium usually used for culture of microorganisms. The culture medium may be a natural medium or a synthetic medium containing a carbon source, a nitrogen source, inorganic salts, other nutritional substances, etc.

Examples of the carbon source include carbohydrates and sugar alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. These carbon sources may be used singly or as a mixture of two or more kinds. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used singly or as a mixture of two or more kinds. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used singly or as a mixture of two or more kinds. The concentration of the inorganic salts in the culture medium varies depending on the kind of the inorganic salts, but is usually about 0.1 to 1 w/v %.

Examples of the nutritional substances include, for example, meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium is usually about 0.1 to 10 w/v %. Further, vitamins may be added as needed. Examples of the vitamins include biotin, thiamine, pyridoxine, pantothenic acid, inositol, nicotinic acid, etc.

The pH of the culture medium is preferably about 6 to 8.

Preferable examples of the microbial culture medium include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BTmedium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc.

The culture temperature is about 15 to 45° C., and the culture period is about 1 to 7 days.

(2) Process for Producing Organic Compound

An organic compound can be produced by a process comprising a step of reacting the above-described coryneform bacterium of the present invention in a reaction mixture containing sugars, and a step of collecting the organic compound from the reaction mixture.

Examples of the organic compound include, in addition to shikimic acid, 3-deoxy-D-arabino-heptulosonate-7-phosphate (DAHP), 3-dehydroquinic acid (3-DHQ), 3-dehydroshikimic acid (3-DHS), shikimate 3-phosphate, 5-enolpyruvylshikimate 3-phosphate, protocatechuic acid, gallic acid, chorismic acid, prephenic acid, phenylpyruvic acid, isochorismic acid, aromatic amino acids including phenylalanine, L-dihydroxyphenylalanine (L-DOPA), tyrosine, pretyrosine, and tryptophan, folate (vitamin M, vitamin B9), menaquinone (vitamin K), p-hydroxybenzoic acid or ubiquinone derived therefrom (coenzyme Q10), p-aminobenzoic acid (vitamin H), p-aminophenol, 4-amino-4-deoxychorismate, anthranilic acid, arogenate, enterobactin, tocopherol (vitamin E), phenol, catechol, aniline, cis,cis-muconate, 3-carboxy-cis,cis-muconate, muconolactone, γ-carboxy muconolactone, β-ketoadipate, cinnamic acid, coumaric acid, coumarin, flavonoid, isoflavonoid, tannin, styrylpyrones, 2,3-dihydroxybenzoic acid, salicylic acid, etc. Among these, preferred are, in addition to shikimic acid, 3-dehydroshikimic acid, 3-dehydroquinic acid, protocatechuic acid, chorismic acid, gallic acid, phenylalanine, tyrosine, tryptophan, anthranilic acid, p-hydroxybenzoic acid, p-aminobenzoic acid, phenol, and catechol.

Glucose is preferred as the sugar, but monosaccharides including fructose, mannose, arabinose, xylose, and galactose, and other sugars that are metabolized to glucose can also be used. Such other sugars include oligosaccharides and polysaccharides having a glucose unit, and examples thereof include disaccharides, such as cellobiose, sucrose, lactose, maltose, trehalose, cellobiose, and xylobiose; polysaccharides, such as dextrin and soluble starch; etc.

Also, molasses, which contains these starting compounds, can also be used, for example. In addition, a saccharified solution which is obtainable by saccharifying, using a diastatic enzyme, non-edible agricultural waste including straw (rice straw, barley straw, wheat straw, rye straw, oat straw, etc.), bagasse, and corn stover; energy crops including switchgrass, napier grass, and *Miscanthus*; wood waste; waste paper; etc. and which contains two or more kinds of sugars, including glucose, can also be used.

Growth of Microorganism

Before the reaction, the transformant is preferably cultured and grown under aerobic conditions at about 25 to 40° C. for about 12 to 48 hours.

Culture Medium

The culture medium used for aerobic culture of the transformant before the reaction may be a natural medium or a synthetic medium containing a carbon source, a nitrogen source, inorganic salts, other nutritional substances, etc.

Examples of the carbon source that can be used include sugars (monosaccharides such as glucose, fructose, mannose, xylose, arabinose, and galactose; disaccharides such as sucrose, maltose, lactose, cellobiose, xylobiose, and trehalose; polysaccharides such as starch; and molasses); sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

These carbon sources may be used singly or as a mixture of two or more kinds.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used singly or as a mixture of two or more kinds. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used singly or as a mixture of two or more kinds. The concentration of the inorganic salts in the culture medium varies depending on the kind of the inorganic salts, but is usually about 0.01 to 1 w/v %.

Examples of the nutritional substances include meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A medium (Inui, M. et al., Metabolic analysis of *Corynebacterium glutamicum* during lactate and succinate productions under oxygen deprivation conditions. J. Mol. Microbiol. Biotechnol. 7:182-196 (2004)), BT medium (Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)), etc. Such a culture medium can be used after prepared so as to contain a sugar at a concentration in the above-mentioned range.

Reaction Mixture

The reaction mixture may be a natural or synthetic reaction mixture containing a carbon source, a nitrogen source, inorganic salts, other nutritional substances, etc.

The carbon source may be one or more of the above-described starting compounds, or a molasses or a saccharified solution containing such compounds. As the carbon source, besides sugars, sugar alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

These carbon sources may be used singly or as a mixture of two or more kinds.

The concentration of the starting compound in the reaction mixture is preferably about 1 to 20 w/v %, more preferably about 2 to 10 w/v %, and still more preferably about 2 to 5 w/v %.

The total concentration of the carbon sources including the starting compound in the reaction mixture is usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used singly or as a mixture of two or more kinds. The concentration of these nitrogen sources in the reaction mixture varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron(II) nitrate, manganese sulfate, zinc sulfate, cobalt sulfate, and calcium carbonate. These inorganic salts may be used singly or as a mixture of two or more kinds. The concentration of the inorganic salts in the reaction mixture varies depending on the kind of the inorganic salts, but is usually about 0.01 to 1 w/v %.

Further, vitamins may be added as needed. Examples of the vitamins include biotin, thiamine (vitamin B1), pyridoxine (vitamin B6), pantothenic acid, inositol, nicotinic acid, etc.

The pH of the reaction mixture is preferably about 6 to 8.

Specific examples of the preferable reaction mixture for coryneform bacteria include the above-mentioned BT medium, etc. Such a culture medium can be used after prepared so as to contain a sugar at a concentration in the above-mentioned range.

Reaction Conditions

The reaction temperature, that is, the temperature for keeping the transformant alive during the reaction is preferably about 15 to 50° C., and more preferably about 25 to 45° C. When the temperature is in the above range, an organic compound can be efficiently produced.

The reaction period is preferably about 1 to 7 days, and more preferably about 1 to 3 days.

The culture may be a batch process, a fed-batch process, or a continuous process. In particular, preferred is the use of a fed-batch fermentor, which allows controlling the temperature, the pH, the aeration conditions, and the oxygen concentration.

The reaction may be performed under aerobic conditions or reducing conditions. The organic compound production ability of the transformant of the present invention is higher under aerobic conditions. The dissolved oxygen concentration (D.O.) in the culture medium is preferably maintained at the D.O. of about 5 to 30% of air saturation. However, aerobic conditions favor the growth of the transformant and the starting compound is consumed for the growth of the bacterial cells. Accordingly, the efficiency of the organic compound production is lowered.

Therefore, in the present invention, it is preferred that the reaction is performed under aerobic conditions where the transformant does not grow. In the present invention, "does not grow" includes "substantially does not grow" and "hardly grows". For example, it is preferred to inhibit the growth of the transformant by the use of a reaction mixture having deficiency or limitation in one or more of vitamins, such as biotin and thiamine, metal salts, nitrogen sources, etc. as compounds which do not have influence on the production of the objective compound by the transformant but are indispensable for the growth of the microorganism. In the present invention, it is more preferred to use a reaction mixture not supplemented with biotin, which is an indispensable vitamin for aerobic growth of a coryneform bacterium.

Under reducing conditions, coryneform bacteria substantially do not grow, and therefore, the starting compound is not consumed for the growth, which leads to a higher efficiency of organic compound production.

The "reducing conditions" is defined based on the oxidation-reduction potential of the reaction mixture. The oxidation-reduction potential of the reaction mixture is preferably about −200 mV to −500 mV, and more preferably about −150 mV to −500 mV.

The reducing conditions of the reaction mixture can be simply estimated using resazurin indicator (in reducing conditions, decolorization from blue to colorless is observed). However, for precise measurement, a redox-potential meter (for example, ORP Electrodes made by BROADLEY JAMES) is used.

As a method of preparing a reaction mixture under reducing conditions, any publicly known method can be used without limitation. For example, as a liquid medium for preparation of the reaction mixture, an aqueous solution for a reaction mixture may be used instead of distilled water or the like. As reference for preparation of the aqueous solution for a reaction mixture, for example, the method for preparing a culture medium for strictly anaerobic microorganisms, such as sulfate-reducing microorganisms (Pfennig, N. et al.: The dissimilatory sulfate-reducing bacteria, In The Prokaryotes, A Handbook on Habitats, Isolation and Identification of Bacteria, Ed. by Starr, M. P. et al. Berlin, Springer Verlag, 926-940, 1981, or Nogeikagaku Jikkensho, Ed. by Kyoto Daigaku Nogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction mixture under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction mixture under reducing conditions can be prepared.

These methods may be suitably combined to prepare an effective aqueous solution for a reaction mixture under reducing conditions.

In the case of a reaction under reducing conditions, it is preferred to maintain the reducing conditions of the reaction mixture during the reaction. For maintenance of reducing conditions, it is preferred that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed. In such a case, for more effective prevention of oxygen incorporation, it is effective to remove oxygen in the solutions to be added, in advance.

Recovery of Organic Compound

Through the culture performed in the above manner, the objective organic compound is produced in the reaction mixture. The objective organic compound can be recovered by collecting the reaction mixture, and it is also feasible to isolate the objective organic compound from the reaction mixture by a known method. Examples of such a known method include the ion-exchange resin method, the concentration method, the crystallization method, the membrane separation method, the organic solvent extraction method, various adsorption methods, etc.

EXAMPLES

Example 1

Construction of Shikimic Acid Producing Strain
(1) Extraction of Chromosomal DNA from Microorganisms To extract chromosomal DNA from *Corynebacterium glutamicum* R (FERM BP-18976), the bacterium was inoculated, using a platinum loop, into A Medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $FeSO_4.7H_2O+0.042\%$ (w/v) $MnSO_4.2H_2O$, 1 mL of 0.02% (w/v) biotin solution, 2 mL of 0.01% (w/v) thiamin solution, 2 g of yeast extract, and 7 g of vitamin assay casamino acid were dissolved in 1 L of distilled water) supplemented with 50% (w/v) glucose as a carbon source to a final concentration of 4%, and cultured with shaking at 33° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

To extract chromosomal DNA from *Escherichia coli* (K12 MG1655), the bacterium was inoculated into LB Medium (10 g of tryptone, 5 g of yeast extract, and 5 g of NaCl were dissolved in 1 L of distilled water) using a platinum loop, and cultured with shaking at 37° C. until the logarithmic growth phase. After the bacterial cells were collected, chromosomal DNA was recovered from the collected cells using a DNA extraction kit (trade name: GenomicPrep Cells and Tissue DNA Isolation Kit, made by Amersham) according to the instruction manual.

(2) Construction of Cloning Vector (2-1) Construction of Cloning Vector pCRB240

A DNA fragment comprising a promoter sequence of the gapA gene encoding the glyceraldehyde-3-phosphate dehydrogenase of *Corynebacterium glutamicum* R, and a DNA fragment comprising an rrnBT1T2 bidirectional terminator sequence (hereinafter abbreviated as terminator sequence) of a cloning vector pKK223-3 (made by Pharmacia) were amplified by the following method.

In the PCR, the following sets of primers were synthesized based on a gene sequence comprising the gapA promoter of *Corynebacterium glutamicum* R (SEQ ID NO: 12: *Corynebacterium glutamicum* gapA promoter sequence) and a cloning vector pKK223-3 (SEQ ID NO: 13: pKK$^{223}$-3), and were used.

Primers for amplification of *Corynebacterium glutamicum* gapA promoter sequence

```
(a-1);
                                            (SEQ ID NO: 14)
5'-CTCTCTGCAGTCGCTCGTCTCATAAAAACGAC-3'

(b-1);
                                            (SEQ ID NO: 15)
5'-CTCTAAGCTTGTCGACGGATCCGCAT

GCTGTGTCTCCTCTAAAGATTGTAGG-3'
```

Primer (a-1) has a PstI restriction enzyme site added thereto, and primer (b-1) has HindIII restriction enzyme site added thereto.

Primers for amplification of pKK223-3 rrnB terminator sequence

```
(a-2);
                                            (SEQ ID NO: 16)
5'-CTCTGCATGCCTGTTTTGGCGGATGAGAGA-3'

(b-2);
                                            (SEQ ID NO: 17)
5'-CTCTAAGCTTGTCGACGGATCCAAGAGTTT

GTAGAAACGCAAAAAGG-3'
```

Primer (a-2) has a SphI restriction enzyme site added thereto, and primer (b-2) has HindIII restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R and the plasmid pKK223-3 were used.

Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |
| Template DNA | 1 μL (DNA content: 1 μg or less) |
| The above set of 2 primers*) | 1 μL each (final conc.: 0.2 μM) |
| Sterile distilled water | 32.5 μL |

*)For amplification of the gapA promoter sequence of *Corynebacterium glutamicum*, a combination of primers (a-1) and (b-1) was used, and for amplification of the rrnB terminator sequence of pKK223-3 plasmid, a combination of primers (a-2) and (b-2) was used.

The above ingredients were mixed, and 50 μL of the reaction mixture was subjected to PCR.

PCR Cycle:
Denaturation step: 98° C., 10 seconds
Annealing step: 55° C., 5 seconds
Extension step: 72° C.
gapA promotor sequence, 29 seconds
rrnB terminator sequence, 26 seconds A cycle consisting of the above 3 steps was repeated 30 times.

Using 10 μL of the above-produced reaction mixture, 0.8% agarose gel electrophoresis was performed, and an about 0.5-kb DNA fragment comprising the gapA promoter sequence of *Corynebacterium glutamicum* R and an about 0.4-kb DNA fragment comprising the rrnB terminator sequence of the plasmid pKK223-3 were detected. The DNA fragments were purified using NucleoSpin Gel and PCR Clean-Up (made by Takara Bio, Inc.).

The about 0.5-kb DNA fragment comprising the gapA promoter sequence of *Corynebacterium glutamicum* R, which was amplified by the above PCR, was cut with the use of restriction enzymes PstI and HindIII, and was purified using NucleoSpin Gel and PCR Clean-Up (made by Takara Bio, Inc.). Also, a cloning vector pCRB1 (J Mol Microbiol Biotechnol. 8(4):243-254 2004)) comprising the pBL1 ori sequence was cut with the use of restriction enzymes PstI and HindIII, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the gapA promoter sequence of *Corynebacterium glutamicum* R and 2 μL of the pCRB1 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture medium and cut with the use of the restriction enzymes to confirm the inserted fragment. As a result, in addition to an about 4.1-kb DNA fragment of the plasmid pCRB1, an about 0.5-kb inserted fragment of the gapA promotor sequence of *Corynebacterium glutamicum* R was confirmed.

The obtained plasmid comprising the gapA promotor sequence from *Corynebacterium glutamicum* R was named Lgap4.

Next, the about 0.4-kb DNA fragment comprising the rrnB terminator sequence of the plasmid pKK223-3, which was amplified by the above PCR, was cut with the use of restriction enzymes SphI and HindIII, and was purified using NucleoSpin Gel and PCR Clean-Up (made by Takara Bio, Inc.). Also, the cloning vector Lgap4 comprising the gapA promoter was with the use of restriction enzymes SphI and HindIII, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the rrnB terminator sequence of the plasmid pKK223-3 and 2 μL of the Lgap4 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture medium and cut with the use of the restriction enzymes to confirm the inserted fragment. As a result, in addition to an about 4.5-kb DNA fragment of the plasmid Lgap4, an about 0.4-kb inserted fragment of the rrnB terminator sequence of the plasmid pKK223-3 was confirmed.

The obtained cloning vector comprising the gapA promoter sequence of *Corynebacterium glutamicum* R and the rrnB terminator sequence of the plasmid pKK223-3 was named pCRB240.

(3) Construction of Shikimic Acid-Producing Gene Expression Plasmids (3-1) Construction of pCRB237 Plasmid A DNA fragment comprising the aroG gene which encodes the 3-deoxy-D-arabino-heptulosonate-7-phosphate (DAHP) synthase gene from *Escherichia coli* K-12 was amplified by the PCR method as described below.

In the PCR, the set of primers shown below was synthesized based on a gene sequence comprising the aroG gene from *Escherichia coli* K-12 (SEQ ID NO: 18: *Escherichia coli* aroG gene), and used.

Primers for Amplification of *Escherichia coli* aroG Gene

```
(a-3);
                                      (SEQ ID NO: 19)
5'-CTCTGATATCATGAATTATCAGAACGACGATTTACGC-3'

(b-3);
                                      (SEQ ID NO: 20)
5'-CTCTGATATCGACTTATCAGGCCTGTGGTG-3'
```

Primers (a-3) and (b-3) each have an EcoRV restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Escherichia coli* K-12 MG1655 was used.

Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |

-continued

| | |
|---|---|
| Template DNA | 1 μL (DNA content: 1 μg or less) |
| The above 2 primers*⁾ | 1 μL each (final conc.: 0.2 μM) |
| Sterile distilled water | 32.5 μL |

*⁾For amplification of the aroG gene of *Escherichia coli*, a combination of primers (a-3) and (b-3) was used.

The above ingredients were mixed, and 50 μL of the reaction mixture was subjected to PCR.

PCR Cycle:

Denaturation step: 98° C., 10 seconds

Annealing step: 55° C., 5 seconds

Extension step: 72° C., 67 seconds

A cycle consisting of the above 3 steps was repeated 30 times.

Using 10 μL of the above-produced reaction mixture, 0.8% agarose gel electrophoresis was performed, and an about 1.1-kb DNA fragment of the aroG gene of *Escherichia coli* K-12 was detected. The DNA fragment was purified using NucleoSpin Gel and PCR Clean-Up (made by Takara Bio, Inc.).

The about 1.1-kb DNA fragment comprising the aroG gene of *Escherichia coli* K-12, which was amplified by the above PCR, was cut with the use of a restriction enzyme EcoRV, and was purified using NucleoSpin Gel and PCR Clean-Up (made by Takara Bio, Inc.). Also, a cloning vector pCRB210 (WO2012/033112) comprising the gapA promoter was cut with the use of restriction enzyme EcoRV, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the aroG gene of *Escherichia coli* K-12 and 2 μL of the pCRB210 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture medium and cut with the use of the restriction enzyme to confirm the inserted fragment. As a result, in addition to an about 5.1-kb DNA fragment of the plasmid pCRB210, an about 1.1-kb inserted fragment of the aroG gene of *Escherichia coli* K-12 was confirmed.

The plasmid comprising the aroG gene of *Escherichia coli* K-12 was named pSKM1.

Using the above-described plasmid pSKM1, a mutant having phenylalanine (F) at the S180 site was prepared by Inverse PCR.

In the PCR, the set of primers shown below was synthesized based on SEQ ID NO: 18 (*Escherichia coli* aroG gene), and used for introduction of mutation to the S180 site of the aroG gene.

Primers for Mutation of *Escherichia coli* aroG Gene (a-4);
(SEQ ID NO: 21)
5'-TTTGTCCGGTCGGCTTCAAAAATG-3'

(b-4);
(SEQ ID NO: 22)
5'-AAAGCCCTGATGCCAGTTC-3'

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the plasmid pSKM1 comprising the aroG gene of *Escherichia coli* K-12 was used.
Reaction Mixture:

| | |
|---|---:|
| PrimeSTAR HS DNA Polymerase (2.5 U/μL) | 0.5 μL |
| 5× PrimeSTAR HS Buffer ($Mg^{2+}$ plus) | 10 μL |
| dNTP Mixture (2.5 mM each) | 4 μL |
| Template DNA | 1 μL (DNA content: 1 μg or less) |
| The above 2 primers*) | 1 μL each (final conc.: 0.2 μM) |
| Sterile distilled water | 32.5 μL |

The above ingredients were mixed, and 50 μL of the reaction mixture was subjected to PCR.

PCR Cycle:
Denaturation step: 98° C., 10 seconds
Annealing step: 60° C., 5 seconds
Extension step: 68° C., 374 seconds A cycle consisting of the above 3 steps was repeated 30 times.

Using 10 μL of the above-produced reaction mixture, 0.8% agarose gel electrophoresis was performed, and an about 6.2-kb DNA fragment comprising the aroG gene of *Escherichia coli* K-12 was detected. The DNA fragment was purified using NucleoSpin Gel and PCR Clean-Up (made by Takara Bio, Inc.).

The purified amplification product was phosphorylated using T4 Polynucleotide Kinase (made by Takara Bio, Inc.) and then purified using NucleoSpin Gel and PCR Clean-Up (made by Takara Bio, Inc.). The obtained phosphorylated DNA fragment was allowed to self-ligate using the DNA Ligation Kit (made by Takara Bio, Inc.). Using the obtained ligation liquid, *Escherichia coli* HST02 was transformed by the calcium chloride method (J. Mol. Biol. 53:159-162 (1970)) and was applied to LB agar medium (1% polypeptone, 0.5% yeast extract, 0.5% sodium chloride, and 1.5% agar) containing 50 μg/mL of kanamycin. A growing strain on the culture medium was subjected to liquid culture in the usual manner. Plasmid DNA was extracted from the culture, and the introduction of the mutation into the S180 site of the aroG gene was confirmed by the sequence analysis of the plasmid.

The obtained plasmid was named pCRB237. The outline of gene recombination of the plasmid is shown in Table 1 below.

(3-2) Construction of pCRB239 Plasmid

Using the above-described plasmid pSKM1, a mutant having leucine (L) at the P150-site was prepared by Inverse PCR.

In the PCR, the set of primers shown below was synthesized based on SEQ ID NO: 18 (*Escherichia coli* aroG gene), and used for introduction of mutation to the P150 site of the aroG gene.

Primers for Mutation of *Escherichia coli* aroG Gene (a-5);
(SEQ ID NO: 23)
5'-TACAATATCTCGCTGACCTGATG-3'

(b-5);
(SEQ ID NO: 24)
5'-GGGTGATCATATCGAGAAACTC-3'

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the plasmid pSKM1 comprising the aroG gene of *Escherichia coli* K-12 was used.
Reaction Mixture:

| | |
|---|---:|
| PrimeSTAR HS DNA Polymerase (2.5 U/μL) | 0.5 μL |
| 5× PrimeSTAR HS Buffer ($Mg^{2+}$ plus) | 10 μL |
| dNTP Mixture (2.5 mM each) | 4 μL |
| Template DNA | 1 μL (DNA content: 1 μg or less) |
| The above 2 primers*) | 1 μL each (final conc.: 0.2 μM) |
| Sterile distilled water | 32.5 μL |

The above ingredients were mixed, and 50 μL of the reaction mixture was subjected to PCR.

PCR Cycle:
Denaturation step: 98° C., 10 seconds
Annealing step: 60° C., 5 seconds
Extension step: 68° C., 374 seconds A cycle consisting of the above 3 steps was repeated 30 times.

Using 10 μL of the above-produced reaction mixture, 0.8% agarose gel electrophoresis was performed, and an about 6.2-kb DNA fragment comprising the aroG gene of *Escherichia coli* K-12 was detected. The DNA fragment was purified using NucleoSpin Gel and PCR Clean-Up (made by Takara Bio, Inc.).

The purified amplification product was phosphorylated using T4 Polynucleotide Kinase (made by Takara Bio, Inc.) and then purified using NucleoSpin Gel and PCR Clean-Up (made by Takara Bio, Inc.). The obtained phosphorylated DNA fragment was allowed to self-ligate using the DNA Ligation Kit (made by Takara Bio, Inc.). Using the obtained ligation liquid, *Escherichia coli* HST02 was transformed by the calcium chloride method (J. Mol. Biol. 53:159-162 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture, and the introduction of the mutation into the P150 site of the aroG gene was confirmed by the sequence analysis of the plasmid.

The obtained plasmid was named pCRB239. The outline of gene recombination of the plasmid is shown in Table 1.

(3-3) Construction of pCRB238 Plasmid

DNA fragments comprising the aroB gene which encodes 3-dehydroquinate synthase gene, the aroD gene which encodes 3-dehydroquinate dehydratase, and the aroE gene which encodes shikimate dehydrogenase of *Corynebacterium glutamicum* R, were amplified by the PCR method as described below.

In the PCR, the following sets of primers were synthesized based on a gene sequence comprising the aroB gene (SEQ ID NO: 25: *Corynebacterium glutamicum* aroB gene), a gene sequence comprising the aroD gene (SEQ ID NO: 26: *Corynebacterium glutamicum* aroD gene), and a gene sequence comprising the aroE gene (SEQ ID NO: 27: *Corynebacterium glutamicum* aroE gene), and were used.
Primers for Amplification of *Corynebacterium glutamicum* aroB Gene

```
(a-6);
                                    (SEQ ID NO: 28)
5'-CTCTGAATTCATGAGCGCAGCGCAGATTTT-3'

(b-6);
                                    (SEQ ID NO: 29)
5'-CTCTCCCGGGAAGTGGATAACTTCTAGTCC-3'
```

Primer (a-6) has an EcoRI restriction enzyme site added thereto, and primer (b-6) has a SmaI restriction enzyme site added thereto.
Primers for Amplification of *Corynebacterium glutamicum* aroD gene

```
(a-7);
                                    (SEQ ID NO: 30)
5'-CTCTGAATTCATGCTTGGAAAAATTCTCCTCC-3'

(b-7);
                                    (SEQ ID NO: 31)
5'-CTCTCCCGGGCTACTTTTTGAGATTTGCCA-3'
```

Primer (a-7) has an EcoRI restriction enzyme site added thereto, and primer (b-7) has a SmaI restriction enzyme site added thereto.
Primers for Amplification of *Corynebacterium glutamicum* aroE Gene

```
(a-8);
                                    (SEQ ID NO: 32)
5'-CTCTCCCGGGATAAGGATCAACGAATAAAA-3'

(b-8);
                                    (SEQ ID NO: 33)
5'-CTCTCTGCAGCTAGTGTTCTTCCGAGATGC-3'
```

Primer (a-8) has a SmaI restriction enzyme site added thereto, and primer (b-8) has PstI restriction enzyme site added thereto.
Actual PCR was performed using a Veriti thermal cycler (made by Applied Biosystems) and PrimeSTAR HS DNA Polymerase (made by Takara Bio, Inc.) as a reaction reagent under the conditions described below. As the template DNA, the chromosomal DNA extracted from *Corynebacterium glutamicum* R was used.
Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |
| Template DNA | 1 μL (DNA content: 1 μg or less) |
| The above set of 2 primers*) | 1 μL each (final conc.: 0.2 μM) |
| Sterile distilled water | 32.5 μL |

*)For amplification of the aroB gene of *Corynebacterium glutamicum*, a combination of primers (a-6) and (b-6) was used, for amplification of the aroD gene of *Corynebacterium glutamicum*, a combination of primers (a-7) and (b-7) was used, and for amplification of the aroE gene of *Corynebacterium glutamicum*, a combination of primers (a-8) and (b-8) was used.

The above ingredients were mixed, and 50 μL of the reaction mixture was subjected to PCR.

PCR Cycle:
  Denaturation step: 98° C., 10 seconds
  Annealing step: 55° C., 5 seconds
  Extension step: 72° C.
  *Corynebacterium glutamicum* aroB gene, 68 seconds
  *Corynebacterium glutamicum* aroD gene, 26 seconds
  *Corynebacterium glutamicum* aroE gene, 50 seconds
  A cycle consisting of the above 3 steps was repeated 30 times.

Using 10 μL of the above-produced reaction mixture, 0.8% agarose gel electrophoresis was performed, and an about 1.1-kb DNA fragment comprising the aroB gene of *Corynebacterium glutamicum*, an about 0.4-kb DNA fragment comprising the aroD gene of *Corynebacterium glutamicum*, and an about 0.8-kb DNA fragment comprising the aroE gene of *Corynebacterium glutamicum* were detected. Each DNA fragment was purified using NucleoSpin Gel and PCR Clean-Up (made by Takara Bio, Inc.).

The about 1.1-kb DNA fragment comprising the aroB gene of *Corynebacterium glutamicum* R, the about 0.4-kb DNA fragment comprising the aroD gene, and the about 0.8-kb DNA fragment comprising the aroE gene, which fragments were amplified by the above PCR, were cut with the use of restriction enzymes EcoRI and SmaI (aroB gene and aroD gene) or SmaI and PstI (aroE gene), and were purified using NucleoSpin Gel and PCR Clean-Up (made by Takara Bio, Inc.). Also, a cloning vector pKK223-3 (made by Pharmacia) comprising the Ptac promoter was cut with the use of restriction enzymes EcoRI and SmaI (aroB gene and aroD gene) or SmaI and PstI (aroE gene), purified using NucleoSpin Gel and PCR Clean-Up (made by Takara Bio, Inc.), and then subjected to dephosphorization using Alkaline Phosphatase, Calf Intestinal (CIP). 10 μL of each of the DNA fragment comprising the aroB gene of *Corynebacterium glutamicum* R, the DNA fragment comprising the aroD gene, and the DNA fragment comprising the aroE gene, was mixed with 2 μL of the pKK223-3 plasmid fragment, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on each culture medium was subjected to liquid culture in the usual manner. Plasmid DNA was extracted from the culture medium and cut with the use of the restriction enzymes to confirm the inserted fragment. As a result, in addition to an about 4.6-kb DNA fragment of the plasmid pKK223-3, an about 1.1-kb inserted fragment of the aroB gene of *Corynebacterium glutamicum* R, an about 0.4-kb inserted fragment of the aroD gene, and an about 0.8-kb inserted fragment of the aroE gene were confirmed.

The obtained plasmid comprising the aroB gene of *Corynebacterium glutamicum* R was named pSKM2, the plasmid comprising the aroD gene was named pSKM3, and the plasmid comprising the aroE gene was named pSKM4.

Next, the above plasmid pSKM3 was cut with the use of restriction enzymes KpnI and SalI. After agarose gel electrophoresis, an about 0.7-kb DNA fragment comprising the aroD gene of *Corynebacterium glutamicum* R was recovered from the agarose gel with the use of QIAquick Gel Extraction Kit (made by QIAGEN). Also, a cloning vector pCRB22 (Appl Environ 5 Microbiol. 78(3):865-875 (2012)) comprising the pCASE1 ori sequence was cut with the use of restriction enzymes KpnI and SalI, purified using Nucleo-Spin Gel and PCR Clean-Up (made by Takara Bio, Inc.), and then subjected to dephosphorization using Alkaline Phosphatase, Calf Intestinal (CIP). 10 µL of the DNA fragment of pSKM3 and 2 µL of the pCRB22 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzymes to confirm the inserted fragment.

The plasmid comprising the araD gene of *Corynebacterium glutamicum* R was named pSKM5.

Next, the above plasmid pSKM2 comprising the aroB gene of *Corynebacterium glutamicum* R was cut with the use of a restriction enzyme SalI. After agarose gel electrophoresis, an about 1.7-kb DNA fragment comprising the aroB gene of *Corynebacterium glutamicum* R was recovered from the agarose gel with the use of QIAquick Gel Extraction Kit (made by QIAGEN). Also, the above plasmid pSKM5 comprising the aroD gene of *Corynebacterium glutamicum* R was cut with the use of a restriction enzyme SalI, and subjected to dephosphorization using Alkaline Phosphatase, Calf Intestinal (CIP). 10 µL of the DNA fragment comprising the aroB gene of pSKM2 and 2 µL of the pSKM5 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzyme to confirm the inserted fragment.

The plasmid comprising the aroB gene and the araD gene of *Corynebacterium glutamicum* R was named pSKM6.

Next, a DNA fragment comprising the aroE gene was amplified from the plasmid pSKM4 comprising the aroE gene of *Corynebacterium glutamicum* R by the PCR method as described below.

In the PCR, the following set of primers was synthesized based on the gene sequence of the plasmid pSKM4 comprising the aroE gene (SEQ ID NO: 34: pSKM4 plasmid sequence), and was used.

Primers for Amplification of *Corynebacterium glutamicum* aroE Gene (a-9);
(SEQ ID NO: 35)
5'-CTCTGGTACCGGCTGTGCAGGTCGTAAATC-3'

(b-9);
(SEQ ID NO: 36)
5'-CTCTGGTACCCTAGTGTTCTTCCGAGATGC-3'

Primers (a-9) and (b-9) each have an KpnI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the plasmid pSKM4 comprising the aroE gene of *Corynebacterium glutamicum* was used.
Reaction Mixture:

| | |
|---|---|
| PrimeSTAR HS DNA Polymerase (2.5 U/µL) | 0.5 µL |
| 5× PrimeSTAR HS Buffer (Mg$^{2+}$ plus) | 10 µL |
| dNTP Mixture (2.5 mM each) | 4 µL |
| Template DNA | 1 µL (DNA content: 1 µg or less) |
| The above 2 primers* | 1 µL each (final conc.: 0.2 µM) |
| Sterile distilled water | 32.5 µL |

*)For amplification of the aroE gene of *Corynebacterium glutamicum*, a combination of primers (a-9) and (b-9) was used.

The above ingredients were mixed, and 50 µL of the reaction mixture was subjected to PCR.
PCR Cycle:
Denaturation step: 98° C., 10 seconds
Annealing step: 55° C., 5 seconds
Extension step: 72° C., 63 seconds
A cycle consisting of the above 3 steps was repeated 30 times.

Using 10 µL of the above-produced reaction mixture, 0.8% agarose gel electrophoresis was performed, and an about 1.0-kb DNA fragment comprising the aroE gene of *Corynebacterium glutamicum* was detected. The DNA fragment was purified using NucleoSpin Gel and PCR Clean-Up (made by Takara Bio, Inc.).

The about 1.0-kb DNA fragment comprising the aroE gene of *Corynebacterium glutamicum* R, which was amplified by the above PCR, was cut with the use of restriction enzyme KpnI, and was purified using NucleoSpin Gel and PCR Clean-Up (made by Takara Bio, Inc.). Also, the above plasmid pSKM6 comprising the aroB gene and the araD gene of *Corynebacterium glutamicum* R was cut with the use of a restriction enzyme KpnI, and subjected to dephosphorization using Alkaline Phosphatase, Calf Intestinal (CIP). 10 µL of the DNA fragment comprising the aroE gene of pSKM4 and 2 µL of the pSKM6 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzyme to confirm the inserted fragment.

The plasmid comprising the aroB gene, the aroD gene, and the aroE gene of *Corynebacterium glutamicum* R was named pSKM7.

Next, a DNA fragment comprising the aroB gene, the aroD gene, and the aroE gene was amplified from the plasmid pSKM7 comprising the aroB gene, the aroD gene, and the aroE gene of *Corynebacterium glutamicum* R by the PCR method as described below.

In the PCR, the following set of primers was synthesized based on the gene sequence of the plasmid pSKM7 comprising the aroB gene, the aroD gene, and the aroE gene of *Corynebacterium glutamicum* R (SEQ ID NO: 37: pSKM7 plasmid sequence), and was used.

Primers for Amplification of *Corynebacterium glutamicum* aroB, aroD, and aroE Genes

```
(a-10);
                             (SEQ ID NO: 38)
5'-CAGGAAACAGCTATGAC-3'

(b-10);
                             (SEQ ID NO: 39)
5'-GTTTTCCCAGTCAGGAC-3'
```

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the plasmid pSKM7 comprising the aroB gene, the aroD gene, and the aroE gene of *Corynebacterium glutamicum* R was used.

Reaction Mixture:

| | |
|---|---|
| PrimeSTAR HS DNA Polymerase (2.5 U/μL) | 0.5 μL |
| 5× PrimeSTAR HS Buffer (Mg²⁺ plus) | 10 μL |
| dNTP Mixture (2.5 mM each) | 4 μL |
| Template DNA | 1 μL (DNA content: 1 μg or less) |
| The above 2 primers*⁾ | 1 μL each (final conc.: 0.2 μM) |
| Sterile distilled water | 32.5 μL |

*⁾For amplification of the aroB gene, the aroD gene, and the aroE gene of *Corynebacterium glutamicum* R, a combination of primers (a-10) and (b-10) was used.

The above ingredients were mixed, and 50 μL of the reaction mixture was subjected to PCR.

PCR Cycle:
Denaturation step: 98° C., 10 seconds
Annealing step: 55° C., 5 seconds
Extension step: 72° C., 215 seconds A cycle consisting of the above 3 steps was repeated 30 times.

Using 10 μL of the above-produced reaction mixture, 0.8% agarose gel electrophoresis was performed, and an about 3.6-kb DNA fragment comprising the aroB gene, the aroD gene, and the aroE gene of *Corynebacterium glutamicum* R was detected. The DNA fragment was purified using NucleoSpin Gel and PCR Clean-Up (made by Takara Bio, Inc.).

The purified amplification product was phosphorylated using T4 Polynucleotide Kinase (made by Takara Bio, Inc.) and then purified using NucleoSpin Gel and PCR Clean-Up (made by Takara Bio, Inc.). Also, a cloning vector pCRB1 (J Mol Microbiol Biotechnol. 8(4):243-254 (2004)) comprising the pBL1 ori sequence was cut using a restriction enzyme SmaI, and subjected to dephosphorization using Alkaline Phosphatase, Calf Intestinal (CIP). 10 μL of the DNA fragment comprising the aroB gene, the aroD gene of pSKM7 and 2 μL of the pCRB1 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture medium and cut with the use of the restriction enzyme to confirm the inserted fragment.

The plasmid comprising the aroB gene, the aroD gene, and the aroE gene of *Corynebacterium glutamicum* R was named pCRB238. The outline of gene recombination of the plasmid is shown in Table 1.

TABLE 1

Plasmids for shikimic acid-producing gene expression

| Plasmids | Introduced gene | Origin of gene | ori | Drug marker |
|---|---|---|---|---|
| pCRB237 | aroG (S180F) | *Escherichia coli* | pCASE1 | Kanamycin |
| pCRB239 | aroG (P150L) | *Escherichia coli* | pCASE1 | Kanamycin |
| pCRB238 | aroB, aroD, aroE | *Corynebacterium glutamicum* | pBL1 | Chloramphenicol |

(4) Enhancement of Gene Expression for Pentose Phosphate Pathway (4-1) Construction of Plasmid for Markerless Chromosomal Introduction of Tkt-Tal Gene A DNA fragment comprising the tkt gene encoding the transketolase of *Corynebacterium glutamicum* R and the tal gene encoding the transaldolase of *Corynebacterium glutamicum* R was amplified by the PCR method as described below.

In the PCR, the set of primers shown below was synthesized based on the gene sequence comprising the tkt gene and the tal gene (SEQ ID NO: 40: *Corynebacterium glutamicum* tkt-tal gene), and was used.

Primers for Amplification of *Corynebacterium glutamicum* Tkt-Tal Gene

```
(a-11);
                             (SEQ ID NO: 41)
5'-CTCTCATATGACGCTGTCACCTGAAC-3'

(b-11);
                             (SEQ ID NO: 42)
5'-CTCTCATATGCTACTTCAGGCGAGCTTC-3'
```

Primers (a-11) and (b-11) each have an NdeI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.

Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |
| Template DNA | 1 μL (DNA content: 1 μg or less) |
| The above 2 primers*) | 1 μL each (final conc.: 0.2 μM) |
| Sterile distilled water | 32.5 μL |

*)For amplification of the tkt-tal gene of *Corynebacterium glutamicum*, a combination of primers (a-11) and (b-11) was used.

The above ingredients were mixed, and 50 μL of the reaction mixture was subjected to PCR.

PCR Cycle:
Denaturation step: 98° C., 10 seconds
Annealing step: 55° C., 5 seconds
Extension step: 72° C., 225 seconds
A cycle consisting of the above 3 steps was repeated 30 times.

Using 10 μL of the above-produced reaction mixture, 0.8% agarose gel electrophoresis was performed, and an about 3.4-kb DNA fragment comprising the tkt-tal gene of *Corynebacterium glutamicum* R was detected. The DNA fragment was purified using NucleoSpin Gel and PCR Clean-Up (made by Takara Bio, Inc.).

The about 3.4-kb DNA fragment comprising the tkt-tal gene of *Corynebacterium glutamicum* R, which was amplified by the above PCR, was cut with the use of a restriction enzyme NdeI, and was purified using NucleoSpin Gel and PCR Clean-Up (made by Takara Bio, Inc.). Also, a cloning vector pCRB209 (WO2012/033112) comprising the PgapA promoter was cut with the use of a restriction enzyme NdeI, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the tkt-tal gene of *Corynebacterium glutamicum* R and 2 μL of the pCRB209 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture medium and cut with the use of the restriction enzyme to confirm the inserted fragment. As a result, in addition to an about 5.1-kb DNA fragment of the plasmid pCRB209, an about 3.4-kb inserted fragment comprising the tkt-tal gene of *Corynebacterium glutamicum* R was confirmed.

The plasmid comprising the tkt-tal gene of *Corynebacterium glutamicum* R was named pSKM8.

Next, a DNA region necessary for markerless introduction of the tkt-tal gene into the chromosome of *Corynebacterium glutamicum* R was determined based on the sequences reported to be nonessential for *Corynebacterium glutamicum* R to grow (Appl. Environ. Microbiol. Vol. 71, 3369-3372 (2005)) (SSI region). The DNA region (SSI9 region) was amplified by the PCR method as described below.

In the PCR, the set of primers shown below was synthesized based on the gene sequence comprising the SSI9 region (SEQ ID NO: 43: *Corynebacterium glutamicum* SSI9 region), and was used.

Primers for Amplification of *Corynebacterium glutamicum* SSI9 Region (a-12);
(SEQ ID NO: 44)
5'-CTCTCCTGCAGGTAATGGTGTCGACCGACATC-3'

(b-12);
(SEQ ID NO: 45)
5'-CTCTCCTGCAGGAAGTTAGATGTGGCTCCGAC-3'

Primers (a-12) and (b-12) each have an Sse8387I restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.

Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |
| Template DNA | 1 μL (DNA content: 1 μg or less) |
| The above 2 primers*) | 1 μL each (final conc.: 0.2 μM) |
| Sterile distilled water | 32.5 μL |

*)For amplification of the SSI9 region of *Corynebacterium glutamicum* R, a combination of primers (a-12) and (b-12) was used.

The above ingredients were mixed, and 50 μL of the reaction mixture was subjected to PCR.

PCR Cycle:
Denaturation step: 98° C., 10 seconds
Annealing step: 55° C., 5 seconds
Extension step: 72° C., 180 seconds
A cycle consisting of the above 3 steps was repeated 30 times.

Using 10 μL of the above-produced reaction mixture, 0.8% agarose gel electrophoresis was performed, and an about 3.0-kb DNA fragment comprising the SSI9 region of *Corynebacterium glutamicum* R was detected. The DNA fragment was purified using NucleoSpin Gel and PCR Clean-Up (made by Takara Bio, Inc.).

The about 3.0-kb DNA fragment comprising the SSI9 region of *Corynebacterium glutamicum* R, which was amplified by the above PCR, was cut with the use of restriction enzyme Ssd8387I, and was purified using NucleoSpin Gel and PCR Clean-Up (made by Takara Bio, Inc.). Also, a plasmid for markerless gene introduction, pCRA725 (J. Mol. Microbiol. Biotechnol. 8:243-254 (2004), (JP 2006-124440 A)) was cut with the use of a restriction enzyme EcoRV, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the SSI9 region of *Corynebacterium glutamicum* R and 2 μL of the pCRA725 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on each culture medium was subjected to liquid culture in the usual manner. Plasmid DNA was extracted from the culture medium and cut with the use of the restriction enzyme to confirm the inserted fragment. As a result, in addition to an about 4.4-kb DNA fragment of the plasmid pCRA725, an about 3.0-kb inserted fragment of the SSI9 region of *Corynebacterium glutamicum* R was confirmed.

The plasmid comprising the SSI9 region of *Corynebacterium glutamicum* R was named pSKM9.

Next, the above plasmid pSKM8 was cut with the use of restriction enzymes BglII and SphI. After agarose gel electrophoresis, an about 4.3-kb DNA fragment comprising the tkt-tal gene of *Corynebacterium glutamicum* R was recovered from the agarose gel with the use of QIAquick Gel Extraction Kit (made by QIAGEN), and then blunting was performed with the use of DNA Blunting Kit (made by Takara Bio, Inc.). Also, the above-described plasmid pSKM9 was cut with the use of a restriction enzyme NaeI, purified using NucleoSpin Gel and PCR Clean-Up (made by Takara Bio, Inc.), and then subjected to dephosphorization using Alkaline Phosphatase, Calf Intestinal (CIP). 10 µL of the DNA fragment comprising the tkt-tal gene of *Corynebacterium glutamicum* R and 2 µL of the pSKM9 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzyme to confirm the inserted fragment.

The obtained plasmid for introduction of the SSI9 region of the tkt-tal gene of *Corynebacterium glutamicum* R was named pSKM10.

(5) Enhancement of Sugar Uptake Activity Mediated by Glucose Transport System Different from PTS (Mediated by Non-PTS Glucose Permease)

(5-1) Construction of Plasmid for Markerless Chromosomal Introduction of iolT1 Gene A DNA fragment comprising the iolT1 gene encoding the inositol transporter of *Corynebacterium glutamicum* R, which is a non-PTS glucose permease, was amplified by the PCR method as described below.

In the PCR, the set of primers shown below was synthesized based on the gene sequence comprising the iolT1 gene (SEQ ID NO: 46: *Corynebacterium glutamicum* iolT1 gene), and was used.

Primers for Amplification of *Corynebacterium glutamicum* iolT1 Gene (a-13);
(SEQ ID NO: 47)
5'-GGAGACCATATGGCTAGTACCTTCATTCAG-3'

(b-13);
(SEQ ID NO: 48)
5'-CCTATTGCATATGAGTGTGCTTCACTCCCG-3'

Primers (a-13) and (b-13) each have an NdeI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.

Reaction Mixture:

| | |
|---|---|
| PrimeSTAR HS DNA Polymerase (2.5 U/µL) | 0.5 µL |
| 5× PrimeSTAR HS Buffer (Mg$^{2+}$ plus) | 10 µL |
| dNTP Mixture (2.5 mM each) | 4 µL |
| Template DNA | 1 µL (DNA content: 1 µg or less) |
| The above 2 primers*⁾ | 1 µL each (final conc.: 0.2 µM) |
| Sterile distilled water | 32.5 µL |

*⁾For amplification of the iolT1 gene of *Corynebacterium glutamicum* R, a combination of primers (a-13) and (b-13) was used.

The above ingredients were mixed, and 50 µL of the reaction mixture was subjected to PCR.

PCR Cycle:
Denaturation step: 98° C., 10 seconds
Annealing step: 55° C., 5 seconds
Extension step: 72° C., 97 seconds
A cycle consisting of the above 3 steps was repeated 30 times.

Using 10 µL of the above-produced reaction mixture, 0.8% agarose gel electrophoresis was performed, and an about 1.6-kb DNA fragment of the iolT1 gene of *Corynebacterium glutamicum* R was detected. The DNA fragment was purified using NucleoSpin Gel and PCR Clean-Up (made by Takara Bio, Inc.).

Next, a DNA region necessary for markerless introduction of the iolT1 gene into the chromosome of *Corynebacterium glutamicum* R was determined based on the sequences reported to be nonessential for *Corynebacterium glutamicum* R to grow (Appl. Environ. Microbiol. Vol. 71, 3369-3372 (2005)) (SSI region). The DNA region (SSI3 region) was amplified by the PCR method as described below.

In the PCR, the set of primers shown below was synthesized based on the gene sequence comprising the SSI3 region (SEQ ID NO: 49: *Corynebacterium glutamicum* SSI3 region), and was used.

Primers for Amplification of *Corynebacterium glutamicum* SSI3 Region (a-14);
(SEQ ID NO: 50)
5'-CTCTGTCGACGAGATCGTACTTCGTAGGC-3'

(b-14);
(SEQ ID NO: 51)
5'-CTCTGTCGACAGCTCGAAATCGAAGACCG-3'

Primers (a-14) and (b-14) each have a SalI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.
Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |
| Template DNA | 1 μL (DNA content: 1 μg or less) |
| The above 2 primers*⁾ | 1 μL each (final conc.: 0.2 μM) |
| Sterile distilled water | 32.5 μL |

*⁾For amplification of the SSI3 region of *Corynebacterium glutamicum* R, a combination of primers (a-14) and (b-14) was used.

The above ingredients were mixed, and 50 μL of the reaction mixture was subjected to PCR.
PCR Cycle:
  Denaturation step: 98° C., 10 seconds
  Annealing step: 55° C., 5 seconds
  Extension step: 72° C., 181 seconds
  A cycle consisting of the above 3 steps was repeated 30 times.

Using 10 μL of the above-produced reaction mixture, 0.8% agarose gel electrophoresis was performed, and an about 3.0-kb DNA fragment comprising the SSI3 region of *Corynebacterium glutamicum* R was detected. The DNA fragment was purified using NucleoSpin Gel and PCR Clean-Up (made by Takara Bio, Inc.).

The about 3.0-kb DNA fragment comprising the SSI3 region of *Corynebacterium glutamicum* R, which was amplified by the above PCR, was cut with the use of restriction enzyme SalI, and was purified using NucleoSpin Gel and PCR Clean-Up (made by Takara Bio, Inc.). Also, a plasmid for markerless gene introduction, pCRA725 (J. Mol. Microbiol. Biotechnol. 8:243-254 (2004), (JP 2006-124440 A)) was cut with the use of a restriction enzyme SalI, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the SSI3 region of *Corynebacterium glutamicum* R and 2 μL of the pCRA725 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture medium and cut with the use of the restriction enzyme to confirm the inserted fragment. As a result, in addition to an about 4.4-kb DNA fragment of the plasmid pCRA725, an about 3.0-kb inserted fragment comprising the SSI3 region of *Corynebacterium glutamicum* R was confirmed.

The obtained plasmid comprising the SSI3 region of *Corynebacterium glutamicum* R was named pSKM11.

Next, Inverse PCR was performed to introduce a restriction enzyme site (unique site) for gene integration into the SSI3 region of the above-described plasmid pSKM11.

In the PCR, the set of primers shown below was synthesized based on the gene sequence comprising the SSI3 region (SEQ ID NO: 49: *Corynebacterium glutamicum* SSI3), and was used.

Primer for Introduction of *Corynebacterium glutamicum* SSI3 Region Restriction Enzyme Site (a-15);
(SEQ ID NO: 52)
5'-CTCTAGATCTACCAACTCCCAGAGCC-3'

(b-15);
(SEQ ID NO: 53)
5'-CTCTAGATCTTTGGCCAGGTCGAACAG-3'

Primers (a-15) and (b-15) each have a BglII restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the plasmid pSKM11 comprising the SSI3 region of *Corynebacterium glutamicum* was used.
Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |
| Template DNA | 1 μL (DNA content: 1 μg or less) |
| The above 2 primers*⁾ | 1 μL each (final conc.: 0.2 μM) |
| Sterile distilled water | 32.5 μL |

*⁾For amplification of the plasmid comprising the SSI3 region of *Corynebacterium glutamicum* R, a combination of primers (a-15) and (b-15) was used.

The above ingredients were mixed, and 50 μL of the reaction mixture was subjected to PCR.
PCR Cycle:
  Denaturation step: 98° C., 10 seconds
  Annealing step: 60° C., 5 seconds
  Extension step: 68° C., 448 seconds
  A cycle consisting of the above 3 steps was repeated 30 times.

Using 10 μL of the above-produced reaction mixture, 0.8% agarose gel electrophoresis was performed, and an about 7.5-kb DNA fragment comprising the SSI3 region of *Corynebacterium glutamicum* R was detected. The DNA fragment was purified using NucleoSpin Gel and PCR Clean-Up (made by Takara Bio, Inc.).

The purified amplification product was subjected to BglII treatment, and then allowed to self-ligate using the DNA Ligation Kit (made by Takara Bio, Inc.). Using the obtained ligation liquid, *Escherichia coli* HST02 was transformed by the calcium chloride method (J. Mol. Biol. 53:159-162 (1970)) and was applied to LB agar medium (1% polypeptone, 0.5% yeast extract, 0.5% sodium chloride, and 1.5% agar) containing 50 g/mL of kanamycin. A growing strain on the culture medium was subjected to liquid culture in the usual manner. Plasmid DNA was extracted from the culture, and the introduction of the BglI restriction enzyme site into the SSI3 region was confirmed by the sequence analysis of the plasmid.

The obtained plasmid comprising the SSI3 region of *Corynebacterium glutamicum* R was named pSKM12.

Next, in order to introduce a tac promotor and a rrnB terminator into the above-described plasmid pSKM12, the tac promoter-comprising cloning vector pCRB214 (FEBS Letters, 586 (23):4228-4232 (2012)) was cut with the use of a restriction enzyme BamHI. After agarose gel electrophoresis, an about 0.7-kb DNA fragment in which the tac promoter and the rrnB terminator were coupled was recovered from the agarose gel with the use of QIAquick Gel Extraction Kit (made by QIAGEN). Also, the plasmid pSKM12 comprising the SSI3 region of *Corynebacterium glutamicum* R was cut with the use of a restriction enzyme BglII, purified using NucleoSpin Gel and PCR Clean-Up (made by Takara Bio, Inc.), and then subjected to dephosphorization using Alkaline Phosphatase, Calf Intestinal (CIP). 10 µL of the DNA fragment comprising the tac promoter and the rrnB terminator recovered from pCRB214 and 2 µL of the pSKM12 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzyme to confirm the inserted fragment.

The obtained plasmid comprising the tac promoter, the rrnB terminator, and the SSI3 region was named pSKM13.

The about 1.6-kb DNA fragment comprising the iolT1 gene of *Corynebacterium glutamicum* R, which was amplified by the above PCR, was cut with the use of a restriction enzyme NdeI, and was purified using NucleoSpin Gel and PCR Clean-Up (made by Takara Bio, Inc.). Also, the cloning vector pSKM13 comprising the tac promoter sequence, the rrnB terminator sequence, and the SSI3 region was cut using a restriction enzyme NdeI, purified using NucleoSpin Gel and PCR Clean-Up (made by Takara Bio, Inc.), and then subjected to dephosphorization using Alkaline Phosphatase, Calf Intestinal (CIP). 10 µL of the DNA fragment comprising the iolT1 gene of *Corynebacterium glutamicum* R and 2 µL of the pSKM13 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on each culture medium was subjected to liquid culture in the usual manner. Plasmid DNA was extracted from the culture medium and cut with the use of the restriction enzyme to confirm the inserted fragment. As a result, in addition to an about 8.5-kb DNA fragment of the plasmid pSKM13, an about 1.6-kb inserted fragment of the iolT1 gene of *Corynebacterium glutamicum* R was confirmed.

The obtained plasmid for introduction of the SSI3 region of the iolT1 gene of *Corynebacterium glutamicum* R was named pSKM14.

(6) Enhancement of Glucokinase Activity (6-1) Construction of Plasmid for Markerless Chromosomal Introduction of Glucokinase Gene A DNA fragment comprising the glk1 gene, the glk2 gene, and the ppgK gene encoding glucokinase of *Corynebacterium glutamicum* R was amplified by the PCR method as described below.

In the PCR, the following sets of primers were synthesized based on the gene sequence comprising the glk1 gene (SEQ ID NO: 54: *Corynebacterium glutamicum* glk1 gene), the gene sequence comprising the glk2 gene (SEQ ID NO: 55: *Corynebacterium glutamicum* glk2 gene), and the gene sequence comprising the ppgK gene (SEQ ID NO: 56: *Corynebacterium glutamicum* ppgK gene), and were used.

Primers for Amplification of *Corynebacterium glutamicum* Glk1 Gene

```
(a-16);
                              (SEQ ID NO: 57)
5'-CTCTGCATGCCACAAAAACCGGCC-3'

(b-16);
                              (SEQ ID NO: 58)
5'-CTCTGCATGCCTAGTTGGCTTCCAACACG-3'
```

Primers (a-16) and (b-16) each have a SphI restriction enzyme site added thereto.

Primers for Amplification of *Corynebacterium glutamicum* Glk2 Gene

```
(a-17);
                              (SEQ ID NO: 59)
5'-CTCTCATATGACTGATCCCACTTGCAC-3'

(b-17);
                              (SEQ ID NO: 60)
5'-CTCTCATATGGAGAACAGCGTTTTAGGTGC-3'
```

Primers (a-17) and (b-17) each have an NdeI restriction enzyme site added thereto.

Primers for Amplification of *Corynebacterium glutamicum* ppgK Gene

```
(a-18);
                              (SEQ ID NO: 61)
5'-CTCTCATATGGCGCGCGGCG-3'

(b-18);
                              (SEQ ID NO: 62)
5'-CTCTCATATGTTATGGGGTGAGGTGTTGG-3'
```

Primers (a-18) and (b-18) each have an NdeI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.

Reaction Mixture:

| | |
|---|---|
| PrimeSTAR HS DNA Polymerase (2.5 U/μL) | 0.5 μL |
| 5× PrimeSTAR HS Buffer (Mg²⁺ plus) | 10 μL |
| dNTP Mixture (2.5 mM each) | 4 μL |
| Template DNA | 1 μL (DNA content: 1 μg or less) |
| The above set of 2 primers*⁾ | 1 μL each (final conc.: 0.2 μM) |
| Sterile distilled water | 32.5 μL |

*⁾For amplification of the glk1 gene of *Corynebacterium glutamicum* R, a combination of primers (a-16) and (b-16) was used, for amplification of the glk2 gene, a combination of primers (a-17) and (b-17) was used, and for amplification of the ppgK gene, a combination of primers (a-18) and (b-18) was used.

The above ingredients were mixed, and 50 μL of the reaction mixture was subjected to PCR.
PCR Cycle:
   Denaturation step: 98° C., 10 seconds
   Annealing step: 55° C., 5 seconds
   Extension step: 72° C.
   glk1 gene, 58 seconds
   glk2 gene, 56 seconds
   ppgK gene, 74 seconds A cycle consisting of the above 3 steps was repeated 30 times.

Using 10 μL of the above-produced reaction mixture, 0.8% agarose gel electrophoresis was performed, and an about 1.0-kb DNA fragment comprising the glk1 gene of *Corynebacterium glutamicum* R, an about 0.9-kb DNA fragment comprising the glk2 gene of *Corynebacterium glutamicum* R, and an about 1.2-kb DNA fragment comprising the ppgK gene of *Corynebacterium glutamicum* R were detected. Each DNA fragment was purified using NucleoSpin Gel and PCR Clean-Up (made by Takara Bio, Inc.).

The about 1.0-kb DNA fragment comprising the glk1 gene of *Corynebacterium glutamicum* R, which was amplified by the above PCR, was cut with the use of restriction enzyme SphI, and was purified using NucleoSpin Gel and PCR Clean-Up (made by Takara Bio, Inc.). Also, a cloning vector pCRB240 comprising the gapA promoter was cut using a restriction enzyme SphI, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the glk1 gene of *Corynebacterium glutamicum* R and 2 μL of the pCRB240 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of chloramphenicol.

A growing strain on the culture medium was subjected to liquid culture in the usual manner. Plasmid DNA was extracted from the culture medium and cut with the use of the restriction enzyme to confirm the inserted fragment. As a result, in addition to an about 5.0-kb DNA fragment of the plasmid pCRB240, an about 1.0-kb inserted fragment of the glk1 gene of *Corynebacterium glutamicum* R was confirmed.

The plasmid comprising the glk1 gene of *Corynebacterium glutamicum* R was named pSKM15.

Next, the about 0.9-kb DNA fragment comprising the glk2 gene of *Corynebacterium glutamicum* R and the about 1.2-kb DNA fragment comprising the ppgK gene of *Corynebacterium glutamicum* R, which fragments were amplified by the above PCR, were cut with the use of a restriction enzyme NdeI, and were purified using NucleoSpin Gel and PCR Clean-Up (made by Takara Bio, Inc.). Also, a cloning vector pCRB210 (WO2012/033112) comprising the gapA promoter was cut with the use of a restriction enzyme NdeI, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the glk2 gene of *Corynebacterium glutamicum* R or the ppgK gene of *Corynebacterium glutamicum* R and 2 μL of the pCRB210 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on each culture medium was subjected to liquid culture in the usual manner. Plasmid DNA was extracted from the culture medium and cut with the use of the restriction enzyme to confirm the inserted fragment. As a result, in addition to an about 5.1-kb DNA fragment of the plasmid pCRB210, an about 0.9-kb inserted fragment in the case of the glk2 gene of *Corynebacterium glutamicum* R, and an about 1.2-kb inserted fragment in the case of the ppgK gene were confirmed.

The obtained plasmid comprising the glk2 gene of *Corynebacterium glutamicum* R was named pSKM16, and the plasmid comprising the ppgK gene of *Corynebacterium glutamicum* R was named pSKM17.

Next, a DNA region necessary for markerless introduction of the glucokinase gene into the chromosome of *Corynebacterium glutamicum* R was determined based on the sequences reported to be nonessential for *Corynebacterium glutamicum* R to grow (Appl. Environ. Microbiol. Vol. 71, 3369-3372 (2005)) (SSI region). The DNA regions (SSI9, 10, 6 regions) were amplified by the PCR method as described below.

In the PCR, the following sets of primers were synthesized based on the gene sequence comprising the SSI9 region (SEQ ID NO: 63: *Corynebacterium glutamicum* SSI9 region), the gene sequence comprising the SSI10 region (SEQ ID NO: 64: *Corynebacterium glutamicum* SSI10 region), and the gene sequence comprising the SSI6 region (SEQ ID NO: 65: *Corynebacterium glutamicum* SSI6 region), and were used.

Primers for Amplification of *Corynebacterium glutamicum* SSI9 Region (a-19);
(SEQ ID NO: 66)
5'-CTCTCCTGCAGGTCCAGTGTGGATCGCAAC-3'

-continued (b-19);
(SEQ ID NO: 67)
5'-CTCTCCTGCAGGGAGGATATGGTGACTAGCTTG-3

Primers (a-19) and (b-19) each have an Sse8387I restriction enzyme site added thereto.
Primers for Amplification of *Corynebacterium glutamicum* SSI10 Region (a-20);
(SEQ ID NO: 68)
5'-CTCTCCTGCAGGCACGGTTGTCAGCTTCACT-3'

(b-20);
(SEQ ID NO: 69)
5'-CTCTCCTGCAGGCTGACTGTGGCATACCTCTA-3'

Primers (a-20) and (b-20) each have an Sse8387I restriction enzyme site added thereto.
Primers for Amplification of *Corynebacterium glutamicum* SSI6 Region (a-21);
(SEQ ID NO: 70)
5'-CTCTCCTGCAGGTTGGGAACTTAGCTAGGTCG-3'

(b-21);
(SEQ ID NO: 71)
5'-CTCTCCTGCAGGTGGAATCAGGATCAGATGCG-3'

Primers (a-21) and (b-21) each have an Sse8387I restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.
Reaction Mixture:

| | |
|---|---|
| PrimeSTAR HS DNA Polymerase (2.5 U/μL) | 0.5 μL |
| 5× PrimeSTAR HS Buffer (Mg$^{2+}$ plus) | 10 μL |
| dNTP Mixture (2.5 mM each) | 4 μL |
| Template DNA | 1 μL (DNA content: 1 μg or less) |
| The above set of 2 primers*⁾ | 1 μL each (final conc.: 0.2 μM) |
| Sterile distilled water | 32.5 μL |

*⁾For amplification of the SSI9 region of *Corynebacterium glutamicum* R, a combination of primers (a-19) and (b-19) was used, for amplification of the SSI10 region, a combination of primers (a-20) and (b-20) was used, and for amplification of the SSI6 region, a combination of primers (a-21) and (b-21) was used.

The above ingredients were mixed, and 50 μL of the reaction mixture was subjected to PCR.
PCR Cycle:
Denaturation step: 98° C., 10 seconds
Annealing step: 55° C., 5 seconds
Extension step: 72° C.
SSI9 region, 194 seconds
SSI10 region, 151 seconds
SSI6 region, 188 seconds
A cycle consisting of the above 3 steps was repeated 30 times.

Using 10 μL of the above-produced reaction mixture, 0.8% agarose gel electrophoresis was performed, and an about 3.2-kb DNA fragment comprising the SSI9 region of *Corynebacterium glutamicum* R, an about 2.5-kb DNA fragment comprising the SSI10 region, and an about 3.1-kb DNA fragment comprising the SSI6 region were detected.

Each DNA fragment was purified using NucleoSpin Gel and PCR Clean-Up (made by Takara Bio, Inc.).

The about 3.2-kb DNA fragment comprising the SSI9 region of *Corynebacterium glutamicum* R, the about 2.5-kb DNA fragment comprising the SSI10 region, and the about 3.1-kb DNA fragment comprising the SSI6 region, which fragments were amplified by the above PCR, were cut with the use of a restriction enzyme Sse8387I, and were purified using NucleoSpin Gel and PCR Clean-Up (made by Takara Bio, Inc.). Also, a plasmid for markerless gene introduction, pCRA725 (J. Mol. Microbiol. Biotechnol. 8:243-254 (2004), (JP 2006-124440 A)) was cut with the use of a restriction enzyme Sse8387I, purified using NucleoSpin Gel and PCRClean-Up (made by Takara Bio, Inc.), and then subjected to dephosphorization using Alkaline Phosphatase, Calf Intestinal (CIP). 10 μL of the DNA fragment comprising the SSI9 region of *Corynebacterium glutamicum* R, the DNA fragment comprising the SSI10 region, or the DNA fragment comprising the SSI6 region was mixed with 2 μL of the pCRA725 plasmid fragment, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on each culture medium was subjected to liquid culture in the usual manner. Plasmid DNA was extracted from the culture medium and cut with the use of the restriction enzyme to confirm the inserted fragment. As a result, in addition to an about 4.4-kb DNA fragment of the plasmid pCRA725, an about 3.2-kb inserted fragment comprising the SSI9 region of *Corynebacterium glutamicum* R, an about 2.5-kb inserted fragment comprising the SSI10 region, and an about 3.1-kb inserted fragment comprising the SSI6 region were confirmed.

The obtained plasmid comprising the SSI9 region of *Corynebacterium glutamicum* R was named pSKM18, the plasmid comprising the SSK10 region was named pSKM19, and the plasmid comprising the SSI6 region was named pSKM20.

Inverse PCR was performed to introduce a restriction enzyme site (unique site) for gene integration into the plasmid pSKM18 comprising the SSI9 region and into the plasmid pSKM20 comprising the SSI6 region.

In the PCR, the following sets of primers were synthesized based on the gene sequence comprising the SSI9 region (SEQ ID NO: 63: *Corynebacterium glutamicum* SSI9 region) and the gene sequence comprising the SSI6 region (SEQ ID NO: 65: *Corynebacterium glutamicum* SSI6 region), and were used.
Primer for Introduction of *Corynebacterium glutamicum* SSI9 Region Restriction Enzyme Site (a-22);
(SEQ ID NO: 72)
5'-CTCTGATATCCTTCCTAAACGATGAGCGAG-3'

(b-22);
(SEQ ID NO: 73)
5'-CTCTGATATCTTGGTCAGTTCAGTCTGGAG-3'

Primers (a-22) and (b-22) each have an EcoRV restriction enzyme site added thereto.

Primer for Introduction of *Corynebacterium glutamicum* SSI6 Region Restriction Enzyme Site

```
(a-23);
                                    (SEQ ID NO: 74)
5'-CTCTAGTACTGCAGATCCATTTCATTGCGC-3'

(b-23);
                                    (SEQ ID NO: 75)
5'-CTCTAGTACTTGGTGGAATTACACGCACC-3'
```

Primers (a-23) and (b-23) each have a ScaI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the plasmid pSKM18 comprising the SSI9 region and the plasmid pSKM20 comprising the SSI6 region were used.

| | |
|---|---|
| PrimeSTAR HS DNA Polymerase (2.5 U/μL) | 0.5 μL |
| 5× PrimeSTAR HS Buffer (Mg²⁺ plus) | 10 μL |
| dNTP Mixture (2.5 mM each) | 4 μL |
| Template DNA | 1 μL (DNA content: 1 μg or less) |
| The above set of 2 primers*⁾ | 1 μL each (final conc.: 0.2 μM) |
| Sterile distilled water | 32.5 μL |

*⁾For amplification of the plasmid comprising the SSI9 region of *Corynebacterium glutamicum* R, a combination of primers (a-22) and (b-22) was used, and for amplification of the plasmid comprising the SSI6 region, a combination of primers (a-23) and (b-23) was used.

Reaction Mixture:

The above ingredients were mixed, and 50 μL of the reaction mixture was subjected to PCR.

PCR Cycle:
Denaturation step: 98° C., 10 seconds
Annealing step: 55° C., 5 seconds
Extension step: 72° C.
SSI9 region, 461 seconds
SSI6 region, 454 seconds A cycle consisting of the above 3 steps was repeated 30 times.

Using 10 μL of the above-produced reaction mixture, 0.8% agarose gel electrophoresis was performed, and an about 7.7-kb DNA fragment comprising the SSI9 region of *Corynebacterium glutamicum* R and an about 7.6-kb DNA fragment comprising the SSI6 region were detected. Each DNA fragment was purified using NucleoSpin Gel and PCR Clean-Up (made by Takara Bio, Inc.).

The above amplified DNA fragment comprising the SSI9 region was treated with a restriction enzyme EcoRV and the above amplified DNA fragment comprising the SSI6 region was treated with a restriction enzyme ScaI. Both were purified using NucleoSpin Gel and PCR Clean-Up (made by Takara Bio, Inc.), and then allowed to self-ligate using the DNA Ligation Kit (made by Takara Bio, Inc.). Using the obtained ligation liquid, *Escherichia coli* HST02 was transformed by the calcium chloride method (J. Mol. Biol. 53:159-162 (1970)) and was applied to LB agar medium (1% polypeptone, 0.5% yeast extract, 0.5% sodium chloride, and 1.5% agar) containing 50 μg/mL of kanamycin.

A growing strain on each culture medium was subjected to liquid culture in the usual manner. Plasmid DNA was extracted from the culture, and the introduction of the EcoRV restriction enzyme site into the SSI9 region or the introduction of the ScaI restriction enzyme site into the SSI6 region was confirmed by the sequence analysis of the plasmid.

The obtained plasmid comprising the SSI9 region of *Corynebacterium glutamicum* R was named pSKM21, and the plasmid comprising the SSI6 region was named pSKM22.

The above plasmid pSKM15 was cut with the use of restriction enzymes PstI and HindIII. After agarose gel electrophoresis, an about 1.9-kb DNA fragment comprising the gkl1 gene of *Corynebacterium glutamicum* R was recovered from the agarose gel with the use of QIAquick Gel Extraction Kit (made by QIAGEN), and then blunting was performed with the use of DNA Blunting Kit (made by Takara Bio, Inc.). Also, the above-described plasmid pSKM21 was cut with the use of a restriction enzyme EcoRV, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the glk1 gene of *Corynebacterium glutamicum* R and 2 μL of the pSKM21 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture medium and cut with the use of the restriction enzyme to confirm the inserted fragment.

The plasmid for introduction of the gkl1 gene of *Corynebacterium glutamicum* R into the chromosomal SSI9 region was named pSKM23.

The above plasmid pSKM16 was cut with the use of a restriction enzyme SalI. After agarose gel electrophoresis, an about 1.9-kb DNA fragment comprising the gkl2 gene of *Corynebacterium glutamicum* R was recovered from the agarose gel with the use of QIAquick Gel Extraction Kit (made by QIAGEN). Also, the above-described plasmid pSKM19 was cut with the use of a restriction enzyme XhoI, purified using NucleoSpin Gel and PCR Clean-Up (made by Takara Bio, Inc.), and then subjected to dephosphorization using Alkaline Phosphatase, Calf Intestinal (CIP). 10 μL of the DNA fragment comprising the glk2 gene of *Corynebacterium glutamicum* R and 2 μL of the pSKM19 plasmid fragment were mixed, and 1 μL of T4 DNA ligase 10× buffer solution and 1 unit of T4 DNA ligase (made by Takara Bio, Inc.) were added thereto. Sterile distilled water was added thereto so that the total amount was 10 μL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 μg/mL of kanamycin.

A growing strain on the culture medium was subjected to liquid culture in the usual manner. Plasmid DNA was extracted from the culture medium and cut with the use of the restriction enzyme to confirm the inserted fragment.

The plasmid for introduction of the gkl2 gene of *Corynebacterium glutamicum* R into the chromosomal SSI10 region was named pSKM24.

The above plasmid pSKM17 was cut with the use of restriction enzymes XbaI and PstI. After agarose gel electrophoresis, an about 1.9-kb DNA fragment comprising the ppgK gene of *Corynebacterium glutamicum* R was recovered from the agarose gel with the use of QIAquick Gel Extraction Kit (made by QIAGEN), and then blunting was performed with the use of DNA Blunting Kit (made by Takara Bio, Inc.). Also, the above-described plasmid pSKM22 was cut with the use of a restriction enzyme ScaI, purified using NucleoSpin Gel and PCR Clean-Up (made by Takara Bio, Inc.), and then subjected to dephosphorization using Alkaline Phosphatase, Calf Intestinal (CIP). 10 µL of the DNA fragment comprising the ppgK gene of *Corynebacterium glutamicum* R and 2 µL of the pSKM22 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzyme to confirm the inserted fragment.

The plasmid for introduction of the ppgK gene of *Corynebacterium glutamicum* R into the chromosomal SSI6 region was named pSKM25.

(7) Construction of Plasmids for *Corynebacterium glutamicum* Chromosomal Gene Disruption (7-1) Construction of Plasmids for *Corynebacterium glutamicum* R qsuB Gene, qsuD Gene, and hdpA Gene Disruption DNA fragments necessary for the construction of plasmids for markerless disruption of the chromosomal qsuB gene encoding 3-dehydroshikimate dehydratase, the qsuD gene encoding quinate/shikimate dehydrogenase, and the hdpA gene encoding dihydroxyacetone phosphate phosphatase (HAD (haloacid dehalogenase) superfamily phosphatase) were amplified by the PCR method as described below.

In the PCR, the following sets of primers were synthesized based on a sequence comprising the qsuB gene (SEQ ID NO: 76: *Corynebacterium glutamicum* qsuB gene), a sequence comprising the qsuD gene (SEQ ID NO: 77: *Corynebacterium glutamicum* qsuD gene), and a sequence comprising the hdpA gene (SEQ ID NO: 78: *Corynebacterium glutamicum* hdpA gene), and were used.

Primers for Amplification of *Corynebacterium glutamicum* qsuB Gene (a-24);
(SEQ ID NO: 79)
5'-CTCTGTCGACCTCAGATTGGTTTCGCAGTC-3'

(b-24);
(SEQ ID NO: 80)
5'-CTGATTGCGCACCAAACCAAGAACGTATCCAAGCAGGTTC-3'

(a-25);
(SEQ ID NO: 81)
5'-TTGGTTTGGTGCGCAATCAG-3'

(b-25);
(SEQ ID NO: 82)
5'-CTCTGTCGACTCAACGGTAGGAAGCTCAG-3'

Primers (a-24) and (b-25) each have a SalI restriction enzyme site added thereto.

Primers for Amplification of *Corynebacterium glutamicum* qsuD Gene (a-26);
(SEQ ID NO: 83)
5'-CTCTGTCGACGTTCTTCGAAGTGGTGGAAC-3'

(b-26);
(SEQ ID NO: 84)
5'-GTGAGGCAGCTGACATCAAACGTTGAAGCCAAGGTAGAG-3'

(a-27);
(SEQ ID NO: 85)
5'-TTTGATGTCAGCTGCCTCAC-3'

(b-27);
(SEQ ID NO: 86)
5'-CTCTGTCGACTGATCACCTTAAAGGGCGAC-3'

Primers (a-26) and (b-27) each have a SalI restriction enzyme site added thereto.

Primers for Amplification of *Corynebacterium glutamicum* hdpA Gene (a-28);
(SEQ ID NO: 87)
5'-CTCTCTGCAGTTGTGGTAGACCTTGGGTG-3'

(b-28);
(SEQ ID NO: 88)
5'-AACACCATTGTCCCTGTTTTGG-3'

(a-29);
(SEQ ID NO: 89)
5'-TCGCCCAAAACAGGGACAATGGTGTTTATTCTGTAGGTCATGGCATTTGC-3'

(b-29);
(SEQ ID NO: 90)
5'-CTCTTCTAGAATTGCAACACCTGCGATGC-3'

Primer (a-28) has a PstI restriction enzyme site added thereto, and primer (b-29) has XbaI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.

Reaction Mixture:

| | |
|---|---|
| PrimeSTAR HS DNA Polymerase (2.5 U/µL) | 0.5 µL |
| 5× PrimeSTAR HS Buffer (Mg$^{2+}$ plus) | 10 µL |
| dNTP Mixture (2.5 mM each) | 4 µL |
| Template DNA | 1 µL (DNA content: 1 µg or less) |

| The above set of 2 primers*) | 1 µL each (final conc.: 0.2 µM) |
| Sterile distilled water | 32.5 µL |

*)For amplification of qsuB-1, a combination of primers (a-24) and (b-24); for amplification of qsuB-2, a combination of primers (a-25) and (b-25); for amplification of qsuD-1, a combination of primers (a-26) and (b-26); for amplification of qsuD-2, a combination of primers (a-27) and (b-27); for amplification of hdpA-1, a combination of primers (a-28) and (b-28); and for amplification of hdpA-2, a combination of primers (a-29) and (b-29) were used.

The above ingredients were mixed, and 50 µL of the reaction mixture was subjected to PCR.
PCR Cycle:
Denaturation step: 98° C., 10 seconds
Annealing step: 55° C., 5 seconds
Extension step: 72° C., 50 seconds
A cycle consisting of the above 3 steps was repeated 30 times.

Using the above-produced reaction mixture, 0.8% agarose gel electrophoresis was performed. In the case of qsuB-1, an about 0.8-kb DNA fragment was detected; in the case of qsuB-2, an about 0.8-kb DNA fragment was detected; in the case of qsuD-1, an about 0.7-kb DNA fragment was detected; in the case of qsuD-2, an about 0.8-kb DNA fragment was detected; in the case of hdpA-1, an about 0.9-kb DNA fragment was detected; and in the case of hdpA-2, an about 0.9-kb DNA fragment was detected. Each DNA fragment was purified using NucleoSpin Gel and PCR Clean-Up (made by Takara Bio, Inc.).

About 20 bps of the 3' end of the DNA fragments qsuB-1, qsuD-1, and hdpA-1, and about 20 bps of the 5' end of the DNA fragments qsuB-2, qsuD-2, and hdpA-2, which fragments were amplified in the above PCR, are designed to overlap, and therefore corresponding two DNA fragments can be ligated by denaturation and subsequent annealing.

Actual ligation was performed using a Veriti thermal cycler (made by Applied Biosystems) and PrimeSTAR HS DNA Polymerase (made by Takara Bio, Inc.) as a reaction reagent under the conditions described below.

The DNA fragments were used as a mixture of qsuB-1 with qsuB-2, qsuD-1 with qsuD-2, and hdpA-1 with hdpA-2.
Reaction Mixture:

| PrimeSTAR HS DNA Polymerase (1.25 U/µL) | 1 µL |
| 5× PrimeSTAR HS Buffer (Mg²⁺ plus) | 10 µL |
| dNTP Mixture (2.5 mM each) | 4 µL |
| DNA fragments | 1 µL each |
| Sterile distilled water | 34 µL |

The above ingredients were mixed, and 50 µL of the reaction mixture was subjected to PCR.
PCR Cycle:
Denaturation step: 98° C., 10 seconds
Annealing step: 50° C., 5 seconds
Extension step: 68° C., 90 seconds
A cycle consisting of the above 3 steps was repeated 15 times.

Using the reaction mixture after the ligation as the template, second PCR was performed under the conditions described below.
Reaction Mixture:

| PrimeSTAR HS DNA Polymerase (2.5 U/µL) | 0.5 µL |
| 5× PrimeSTAR HS Buffer (Mg²⁺ plus) | 10 µL |
| dNTP Mixture (2.5 mM each) | 4 µL |
| Reaction mixture after the ligation | 1 µL (DNA content: 1 µg or less) |
| The above set of 2 primers*) | 1 µL each (final conc.: 0.2 µM) |
| Sterile distilled water | 32.5 µL |

*)For amplification of the qsuB gene of *Corynebacterium glutamicum* R, a combination of primers (a-24) and (b-25) was used, for amplification of the qsuD gene, a combination of primers (a-26) and (b-27) was used, and for amplification of the hdpA gene, a combination of primers (a-28) and (b-29) was used.

The above ingredients were mixed, and 50 µL of the reaction mixture was subjected to PCR.
PCR Cycle:
Denaturation step: 98° C., 10 seconds
Annealing step: 50° C., 5 seconds
Extension step: 68° C.
qsuB gene, 96 seconds
qsuD gene, 92 seconds
hdpA gene, 110 seconds
A cycle consisting of the above 3 steps was repeated 20 times.

Using the above generated reaction mixture, 0.8% agarose gel electrophoresis was performed. In the case of the qsuB gene, the qsuD gene, and the hdpA gene, about 1.6-kb, about 1.5-kb, and about 1.8-kb DNA fragments were respectively detected. Each DNA fragment was purified using NucleoSpin Gel and PCR Clean-Up (made by Takara Bio, Inc.).

After amplification by the above PCR, the DNA fragment comprising the qsuB gene of *Corynebacterium glutamicum* R and the DNA fragment comprising the qsuD gene were cut with the use of a restriction enzyme SalI, and the DNA fragment comprising the hdpA gene was cut with the use of restriction enzymes PstI and XbaI, and then purification using NucleoSpin Gel and PCR Clean-Up (made by Takara Bio, Inc.) was performed. Also, a plasmid for markerless gene disruption, pCRA725 (J. Mol. Microbiol. Biotechnol. 8:243-254 (2004), (JP 2006-124440 A)) was cut with the use of a restriction enzyme SalI (qsuB gene and qsuD gene) or restriction enzymes PstI and XbaI (hdpA gene), and then subjected to dephosphorization using Alkaline Phosphatase, Calf Intestinal (CIP). 10 µL of the DNA fragment comprising the qsuB gene of *Corynebacterium glutamicum* R, the DNA fragment comprising the qsuD gene, or the DNA fragment comprising the hdpA gene was mixed with 2 µL of the pCRA725 plasmid fragment, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (J. Mol. Biol. 53:159-162 (1970)) and was applied to LB agar medium (1% polypeptone, 0.5% yeast extract, 0.5% sodium chloride, and 1.5% agar) containing 50 µg/mL of kanamycin.

A growing strain on each culture medium was subjected to liquid culture in the usual manner. Plasmid DNA was extracted from the culture medium and cut with the use of the restriction enzyme(s) to confirm the inserted fragment. As a result, in addition to an about 4.0-kb DNA fragment of the plasmid pCRB725, an about 1.6-kb fragment in the case of the qsuB gene, an about 1.5-kb DNA fragment in the case of the qsuD gene, and an about 1.8-kb fragment in the case of the hdpA gene were detected.

The obtained plasmid for disruption of the qsuB gene of *Corynebacterium glutamicum* R was named pSKM26, the plasmid for disruption of the qsuD gene was named pSKM27, and the plasmid for disruption of the hdpA gene was named pSKM28.

(7-2) Construction of Plasmid for *Corynebacterium glutamicum* R aroK Gene Disruption A DNA fragment necessary for the construction of a plasmid for markerless disruption of the aroK gene encoding the shikimate kinase of *Corynebacterium glutamicum* R was amplified by the PCR method as described below.

In the PCR, the set of primers shown below was synthesized based on the gene sequence comprising the aroK gene (SEQ ID NO: 91: *Corynebacterium glutamicum* aroK gene), and was used.

Primers for Amplification of *Corynebacterium glutamicum* aroK Gene (a-30);
(SEQ ID NO: 92)
5'-AGGCATGCGGAGGTGCTCTCTCACGTAA-3'

(b-30);
(SEQ ID NO: 93)
5'-TCCCCCGGGCGAGCACTACCGCAACCT-3'

(a-31);
(SEQ ID NO: 94)
5'-TCCCCCGGGCCGGAGGATTTCAGTGCTT-3'

(b-31);
(SEQ ID NO: 95)
5'-AGGCATGCCACTGCAACGGCATTGCCGT-3'

Primers (a-30) and (b-31) each have a SphI restriction enzyme site added thereto, and primers (a-31) and (b-30) each have a SmaI restriction enzyme site added thereto.

Actual PCR was performed using a Veriti thermal cycler (made by Applied Biosystems) and PrimeSTAR HS DNA Polymerase (made by Takara Bio, Inc.) as a reaction reagent under the conditions described below.

As the template DNA, the chromosomal DNA extracted from *Corynebacterium glutamicum* R was used.

Reaction Mixture:

| | |
|---|---|
| PrimeSTAR HS DNA Polymerase (2.5 U/µL) | 0.5 µL |
| 5× PrimeSTAR HS Buffer (Mg²⁺ plus) | 10 µL |
| dNTP Mixture (2.5 mM each) | 4 µL |
| Template DNA | 1 µL (DNA content: 1 µg or less) |
| The above set of 2 primers*⁾ | 1 µL each (final conc.: 0.2 µM) |
| Sterile distilled water | 32.5 µL |

*⁾For amplification of the aroK-1, a combination of primers (a-30) and (b-30), and for amplification of the aroK-2, a combination of primers (a-31) and (b-31) were used.

The above ingredients were mixed, and 50 µL of the reaction mixture was subjected to PCR.

PCR Cycle:
Denaturation step: 98° C., 10 seconds
Annealing step: 55° C., 5 seconds
Extension step: 72° C.
aroK-1, 60 seconds
aroK-2, 62 seconds
A cycle consisting of the above 3 steps was repeated 30 times.

Using 10 µL of the above-produced reaction mixture, 0.8% agarose gel electrophoresis was performed, and an about 1.0-kb DNA fragment aroK-1 and an about 1.0-kb DNA fragment aroK-2 of *Corynebacterium glutamicum* R were detected. Each DNA fragment was purified using NucleoSpin Gel and PCR Clean-Up (made by Takara Bio, Inc.).

The about 1.0-kb DNA fragment aroK-1 and the about 1.0-kb DNA fragment aroK-2, which were amplified by the above PCR and comprise the aroK gene of *Corynebacterium glutamicum* R, were cut with the use of restriction enzymes SphI and SmaI, and were purified using NucleoSpin Gel and PCR Clean-Up (made by Takara Bio, Inc.). Also, a plasmid for markerless gene disruption, pCRA725 (J. Mol. Microbiol. Biotechnol. 8:243-254 (2004), (JP 2006-124440 A)) was cut with the use of a restriction enzyme SphI, purified using NucleoSpin Gel and PCR Clean-Up (made by Takara Bio, Inc.), and then subjected to dephosphorization using Alkaline Phosphatase, Calf Intestinal (CIP). 10 µL each of the two kinds of DNA fragments comprising the aroK gene of *Corynebacterium glutamicum* R and 2 µL of the pCRA725 plasmid fragment were mixed, and 1 µL of T4 DNA ligase 10× buffer solution and 1 unit of T4 DNA ligase (made by Takara Bio, Inc.) were added thereto. Sterile distilled water was added thereto so that the total amount was 10 µL, and the mixture was allowed to react at 15° C. for 3 hours for ligation.

Using the obtained ligation liquid, *Escherichia coli* HST02 was transformed by the calcium chloride method (Journal of Molecular Biology, 53, 159 (1970)) and was applied to LB agar medium (1% polypeptone, 0.5% yeast extract, 0.5% sodium chloride, and 1.5% agar) containing 50 µg/mL of kanamycin.

A growing strain on the culture medium was subjected to liquid culture in the usual manner. Plasmid DNA was extracted from the culture medium and cut with the use of the restriction enzymes to confirm the inserted fragment. As a result, in addition to an about 4.4-kb DNA fragment of the plasmid pCRA725, an about 2.0-kb inserted fragment having partially deleted aroK gene of *Corynebacterium glutamicum* R was confirmed.

The obtained plasmid for markerless disruption of the aroK gene of *Corynebacterium glutamicum* R was named pCRC329.

(8) Construction of Shikimic Acid Producing Strains by Chromosomal Gene Recombination Vector pCRA725 for markerless chromosomal gene transfection is a plasmid that cannot be replicated within *Corynebacterium glutamicum* R. With the use of the plasmid pCRA728 (J. Mol. Microbiol. Biotechnol. 8(4):243-254 (2004)) for *Corynebacterium glutamicum* R ldhA gene disruption, transformation of *Corynebacterium glutamicum* X5C1 strain (Appl Microbiol Biotechnol. 81(4):691-699 (2008)) was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin. The single crossover strain obtained on the above medium was applied to BT agar medium (2 g of (NH₂)₂CO, 7 g of (NH₄)₂SO₄, 0.5 g of KH₂PO₄, 0.5 g of K₂HPO₄, 0.5 g of MgSO₄.7H₂O, 1 mL of 0.06% (w/v) Fe₂SO₄.7H₂O+0.042% (w/v) MnSO₄.2H₂O, 1 mL of 0.02% (w/v) biotin solution, and 2 mL of 0.01% (w/v) thiamin solution dissolved in 1 L of distilled water, and 1.5% agar) containing 10% (w/v) sucrose.

In the case of a single crossover strain between the plasmid pCRA728 and the homologous region of the chromosome, the strain shows kanamycin resistance due to expression of the kanamycin-resistant gene on pCRA728 but lacks growing ability in culture medium containing sucrose due to expression of the sacR-sacB gene of *Bacillus subtilis*.

In the case of double crossover strain, the strain shows kanamycin sensitivity due to deletion of the kanamycin-resistant gene from pCRA728 and growing ability in culture medium containing sucrose due to deletion of the sacR-sacB gene from pCRA728. The markerless chromosomal gene disruptant shows kanamycin sensitivity and growing ability on a culture medium containing sucrose.

Therefore, a strain that showed kanamycin sensitivity and growing ability on a culture medium containing sucrose was selected. This strain, obtained by markerless disruption of the ldhA gene of *Corynebacterium glutamicum* R, was named *Corynebacterium glutamicum* X5C1ΔldhA.

Next, with the use of the plasmid pCRD109 for chromosomal introduction of arabinose utilization gene (Appl Microbiol Biotechnol. 85(1):105-115 (2009)), transformation of the *Corynebacterium glutamicum* X5C1ΔldhA was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained in the above culture medium was applied to BT agar medium (BT liquid medium containing 1.5% agar) containing 10% (w/v) sucrose.

A strain having kanamycin sensitivity and growing ability in a culture medium containing sucrose was selected from growing strains on the medium. The obtained strain having chromosomally introduced arabinose utilization gene was named *Corynebacterium glutamicum* A1X5C1ΔldhA.

Next, with the use of the plasmid pCRD108 for chromosomal introduction of arabinose transporter gene (Appl Microbiol Biotechnol. 85(1):105-115 (2009)), transformation of the *Corynebacterium glutamicum* A1X5C1ΔldhA was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained in the above culture medium was applied to BT agar medium (BT liquid medium containing 1.5% agar) containing 10% (w/v) sucrose.

A strain having kanamycin sensitivity and growing ability in a culture medium containing sucrose was selected from growing strains on the medium. The obtained strain having a chromosomally introduced arabinose transporter gene was named *Corynebacterium glutamicum* A1X5C1araEΔldhA.

Next, with the use of the plasmid pSKM26 for disruption of the qsuB gene of *Corynebacterium glutamicum*, transformation of the *Corynebacterium glutamicum* A1X5C1araEΔldhA was performed by electroporation (Agric. Biol. Chem., 54:443-447 (1990) and Res. Microbiol., 144:181-185 (1993)), and the strain was applied to A agar medium (A liquid medium and 1.5% agar) containing 50 μg/mL of kanamycin. The single crossover strain obtained in the above culture medium was applied to BT agar medium (BT liquid medium containing 1.5% agar) containing 10% (w/v) sucrose.

A strain having kanamycin sensitivity and growing ability in a culture medium containing sucrose was selected from growing strains on the medium. The *Corynebacterium glutamicum* R qsuB gene disruptant was named *Corynebacterium glutamicum* SKM8.

Next, with the use of the plasmid pSKM27 for disruption of the qsuD gene of *Corynebacterium glutamicum* R, transformation of the *Corynebacterium glutamicum* SKM8 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained in the above culture medium was applied to BT agar medium (BT liquid medium containing 1.5% agar) containing 10% (w/v) sucrose.

A strain having kanamycin sensitivity and growing ability in a culture medium containing sucrose was selected from growing strains on the medium. This strain, obtained by markerless disruption of the qsuD gene of *Corynebacterium glutamicum* R, was named *Corynebacterium glutamicum* SKM9.

Next, with the use of the plasmid pCRC329 for disruption of the aroK gene of *Corynebacterium glutamicum* R, transformation of the *Corynebacterium glutamicum* SKM9 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained in the above culture medium was applied to BT agar medium containing aromatic amino acids (BT liquid medium containing 1.5% agar, supplemented with 20 μg/mL each of phenylalanine, tyrosine, and tryptophan, and 10 μg/mL of p-aminobenzoic acid) and 10% (w/v) sucrose.

A strain having kanamycin sensitivity and growing ability in a culture medium containing sucrose was selected from growing strains on the medium. This strain, obtained by markerless disruption of the aroK gene of *Corynebacterium glutamicum* R, was named *Corynebacterium glutamicum* SKM1.

Next, with the use of the plasmid pSKM10 for introduction of the tkt-tal gene of *Corynebacterium glutamicum* R, transformation of the *Corynebacterium glutamicum* SKM1 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. The strain obtained by *Corynebacterium glutamicum* R tkt-tal gene markerless chromosomal introduction was named *Corynebacterium glutamicum* SKM2.

Next, with the use of the plasmid pSKM14 for introduction of the iolT1 gene of *Corynebacterium glutamicum* R, transformation of the *Corynebacterium glutamicum* SKM2 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 μg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. The strain obtained by *Corynebacterium glutamicum* R iolT1 gene markerless chromosomal introduction was named *Corynebacterium glutamicum* LHglc553.

Next, with the use of the plasmid pCRC809 (Microbiology, 155(Pt11):3652-3660 (2009)) for disruption of the ptsH gene of *Corynebacterium glutamicum* R, transformation of the *Corynebacterium glutamicum* LHglc533 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. This strain, obtained by markerless disruption of the ptsH gene of *Corynebacterium glutamicum* R, was named *Corynebacterium glutamicum* LHglc567.

Next, with the use of the plasmid pSKM25 for introduction of the ppgK gene of *Corynebacterium glutamicum* R, transformation of the *Corynebacterium glutamicum* LHglc567 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. The strain obtained by *Corynebacterium glutamicum* R ppgK gene markerless chromosomal introduction was named *Corynebacterium glutamicum* LHglc594.

Next, with the use of the plasmid pSKM23 for introduction of the glk1 gene of *Corynebacterium glutamicum* R, transformation of the *Corynebacterium glutamicum* LHglc594 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. The strain obtained by *Corynebacterium glutamicum* R glk1 gene markerless chromosomal introduction was named *Corynebacterium glutamicum* LHglc611.

Next, with the use of the plasmid pSKM24 for introduction of the glk2 gene of *Corynebacterium glutamicum* R, transformation of the *Corynebacterium glutamicum* LHglc611 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. The strain obtained by *Corynebacterium glutamicum* R glk2 gene markerless chromosomal introduction was named *Corynebacterium glutamicum* LHglc618.

Next, with the use of the plasmid pCRD906 (Appl Environ Microbiol. 78(12):4447-4457 (2012)) for introduction of the gapA gene of *Corynebacterium glutamicum* R, transformation of the *Corynebacterium glutamicum* LHglc618 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. The strain obtained by *Corynebacterium glutamicum* R gapA gene markerless chromosomal introduction was named *Corynebacterium glutamicum* LHglc741.

Next, with the use of the plasmid pSKM28 for disruption of the hdpA gene of *Corynebacterium glutamicum* R, transformation of the *Corynebacterium glutamicum* LHglc741 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. This strain, obtained by markerless disruption of the hdpA gene of *Corynebacterium glutamicum* R, was named *Corynebacterium glutamicum* LHglc753.

Also, with the use of the plasmid pCRD907 (Appl Environ Microbiol. 78(12):4447-4457 (2012)) for introduction of the gapA gene of *Corynebacterium glutamicum* R, transformation of the *Corynebacterium glutamicum* SKM2 was performed by electroporation (Agric. Biol. Chem., Vol. 54, 443-447 (1990) and Res. Microbiol., Vol. 144, 181-185 (1993)), and the strain was applied to A agar medium (A liquid medium and 1.5% agar) containing 50 µg/mL of kanamycin and aromatic amino acids. The single crossover strain obtained in the above culture medium was applied to BT agar medium containing 10% (w/v) sucrose and aromatic amino acids.

A strain having kanamycin sensitivity and growing ability in a culture medium containing sucrose was selected from growing strains on the medium. The strain obtained by *Corynebacterium glutamicum* R gapA gene markerless chromosomal introduction was named *Corynebacterium glutamicum* LHglc573.

TABLE 2

Construction of shikimic acid producing strains by chromosomal gene recombination

| Strain | Recombinant plasmid | Chromosomally introduced gene | Disrupted chromosomal gene |
|---|---|---|---|
| X5C1 | | xylAB, bglF(V317A)A | |
| 5C1ΔldhA | pCRA728 | xylAB, bglF(V317A)A | ldhA |
| A1X5C1ΔldhA | pCRD109 | xylAB, bglF(V317A)A, araBAD | ldhA |
| A1X5C1araEΔldhA | pCRD108 | xylAB, bglF(V317A)A, araBAD, araE | ldhA |
| LHglc453 | pSKM26 | xylAB, bglF(V317A)A, araBAD, araE | qsuB, ldhA |
| SKM9 | pSKM27 | xylAB, bglF(V317A)A, araBAD, araE | qsuB, qsuD, ldhA |
| SKM1 | pCRC329 | xylAB, bglF(V317A)A, araBAD, araE | qsuB, qsuD, aroK, ldhA |
| SKM2 | pSKM10 | xylAB, bglF(V317A)A, araBAD, araE, tkt-tal | qsuB, qsuD, aroK, ldhA |
| LHglc553 | pSKM14 | xylAB, bglF(V317A)A, araBAD, araE, tkt-tal, iolT1 | qsuB, qsuD, aroK, ldhA |
| LHglc567 | pCRC809 | xylAB, bglF(V317A)A, araBAD, araE, tkt-tal, iolT1 | qsuB, qsuD, aroK, ptsH, ldhA |
| LHglc594 | pSKM25 | xylAB, bglF(V317A)A, araBAD, araE, tkt-tal, iolT1, ppgK | qsuB, qsuD, aroK, ptsH, ldhA |
| LHglc611 | pSKM23 | xylAB, bglF(V317A)A, araBAD, araE, tkt-tal, iolT1, ppgK, glk1 | qsuB, qsuD, aroK, ptsH, ldhA |
| LHglc618 | pSKM24 | xylAB, bglF(V317A)A, araBAD, araE, tkt-tal, iolT1, ppgK, glk1, glk2 | qsuB, qsuD, aroK, ptsH, ldhA |
| LHglc741 | pCRD906 | xylAB, bglF(V317A)A, araBAD, araE, tkt-tal, iolT1, ppgK, glk1, glk2, gapA | qsuB, qsuD, aroK, ptsH, ldhA |
| LHglc753 | pSKM28 | xylAB, bglF(V317A)A, araBAD, araE, tkt-tal, iolT1, ppgK, glk1, glk2, gapA | qsuB, qsuD, aroK, ptsH, hdpA, ldhA |
| LHglc573 | pCRD907 | xylAB, bglF(V317A)A, araBAD, araE, tkt-tal, gapA | qsuB, qsuD, aroK, ldhA |

List of Abbreviations*
tkt-tal: transketolase (tkt) and transaldolase (tal)
iolT1: myo-inositol transporter
glk1: glucokinase 1
glk2: glucokinase 2
ppgK: polyphosphate/ATP dependent glucokinase
gapA: glyceraldehyde 3-phosphate dehydrogenase
xylAB: xylose isomerase and xylulokinase (*Escherichia coli*)
bglF(V317A)A: mutant β-glucosidase (bglF(V317A)) and 6-phospho-β-glucosidase (bglA) araBAD: arabinose isomerase, ribulokinase, and ribulose 5-phosphate 3-epimerase) (*Escherichia coli*)
araE: arabinose transporter (*Corynebacterium glutamicum* 31831)
ldhA: lactate dehydrogenase A
aroK: shikimate kinase
qsuB: 3-dehydroshikimate dehydratase
qsuD: quinate/shikimate dehydrogenase
ptsH: histidine-phosphorylatable protein
hdpA: HAD(haloacid dehalogenase) superfamily phosphatase
aroG(S180F): feedback-resistant mutant DAHP(3-deoxy-D-arabinoheptulo-sonate-7-phosphate) synthase (S180F) (*Escherichia coli*)
aroG(P150L): feedback-resistant mutant DAHP synthase (P150L) (*Escherichia coli*)
aroB: 3-dehydroquinate synthase
aroD: 3-dehydroquinate dehydratase
aroE: shikimate dehydrogenase
*Genes are of *Corynebacterium glutamicum* R origin unless otherwise stated (9) Construction of Strains Having Shikimic Acid-Producing Gene Expression Plasmids With the use of the above-described plasmid pCRB237, transformation of *Corynebacterium glutamicum* SKM2 was performed by electroporation (Agric. Biol. Chem., Vol. 54, 443-447 (1990) and Res. Microbiol., Vol. 144, 181-185 (1993)), and the strain was applied to A agar medium containing 50 μg/mL of kanamycin.

A growing strain on the culture medium was subjected to liquid culture in the usual manner. Plasmid DNA was extracted from the culture and cut with the use of a restriction enzyme to confirm the inserted plasmids. As a result, introduction of the above-constructed plasmid pCRB237 was confirmed.

The obtained strain was named *Corynebacterium glutamicum* SKM3. The outline of gene recombination of the plasmid is shown in Table 3.

With the use of the above-described plasmids pCRB237 and pCRB238, transformation of *Corynebacterium glutamicum* SKM2, LHglc618, LHglc741, LHglc753, and SKM1 was performed by electroporation (Agric. Biol. Chem., Vol. 54, 443-447 (1990) and Res. Microbiol., Vol. 144, 181-185

(1993)), and the strains were separately applied to A agar medium containing 50 µg/mL of kanamycin and 5 µg/mL of chloramphenicol.

A growing strain on each culture medium was subjected to liquid culture in the usual manner. Plasmid DNA was extracted from the culture and cut with the use of a restriction enzyme to confirm the inserted plasmids. As a result, introduction of the above-constructed plasmids pCRB237 and pCRB238 was confirmed.

The transformants obtained by introducing the plasmids pCRB237 and pCRB238 into each of *Corynebacterium glutamicum* SKM2, LHglc618, LHglc741, LHglc753, and SKM1 were named *Corynebacterium glutamicum* SKM4, SKM5, SKM6, SKM7, and SKM10, respectively. The outline of gene recombination of the plasmids is shown in Table 3.

With the use of the above-described plasmids pCRB239 and pCRB238, transformation of *Corynebacterium glutamicum* SKM2 and LHglc573 was performed by electroporation (Agric. Biol. Chem., Vol. 54, 443-447 (1990) and Res. Microbiol., Vol. 144, 181-185 (1993)), and the strains were separately applied to A agar medium containing 50 µg/mL of kanamycin and 5 µg/mL of chloramphenicol.

A growing strain on each culture medium was subjected to liquid culture in the usual manner. Plasmid DNA was extracted from the culture and cut with the use of a restriction enzyme to confirm the inserted plasmids. As a result, introduction of the above-constructed plasmids pCRB239 and pCRB238 was confirmed.

The obtained strains were named *Corynebacterium glutamicum* SK11 and SKM12.

The outline of gene recombination of the plasmids is shown in Table 3.

*Corynebacterium glutamicum* SKM7 was deposited in Incorporated Administrative Agency National Institute of Technology and Evaluation, NITE Patent Microorganisms Depositary (2-5-8 Kazusakamatari, Kisarazu-shi, Chiba 292-0818 Japan) under Accession Number NITE BP-01903 on Jul. 29, 2014.

TABLE 3

Strains used in shikimic acid-production experiment

| Strain | Chromosomally introduced gene*) | Disrupted chromosomal gene | Introduced gene on plasmid |
|---|---|---|---|
| A1X5C1araEΔldhA | | ΔldhA | |
| SKM1 | | ΔaroK, ΔqsuB, ΔqsuD, ΔldhA | |
| SKM2 | tkt-tal | ΔaroK, ΔqsuB, ΔqsuD, ΔldhA | |
| SKM3 | tkt-tal | ΔaroK, ΔqsuB, ΔqsuD, ΔldhA | aroG(S180F) |
| SKM4 | tkt-tal | ΔaroK, ΔqsuB, ΔqsuD, ΔldhA | aroG(S180F), aroB, aroD, aroE |
| SKM5 | tkt-tal, iolT1, glk1, glk2, ppgK | ΔaroK, ΔqsuB, ΔqsuD, ΔldhA, ΔptsH | aroG(S180F), aroB, aroD, aroE |
| SKM6 | tkt-tal, iolT1, glk1, glk2, ppgK, gapA | ΔaroK, ΔqsuB, ΔqsuD, ΔldhA, ΔptsH | aroG(S180F), aroB, aroD, aroE |
| SKM7 | tkt-tal, iolT1, glk1, glk2, ppgK, gapA | ΔaroK, ΔqsuB, ΔqsuD, ΔldhA, ΔptsH, hdpA | aroG(S180F), aroB, aroD, aroE |
| SKM8 | | ΔqsuB, ΔldhA | |
| SKM9 | | ΔqsuB, ΔqsuD, ΔldhA | |
| SKM10 | | ΔaroK, ΔqsuB, ΔqsuD, ΔldhA | aroG(S180F), aroB, aroD, aroE |
| SKM11 | tkt-tal | ΔaroK, ΔqsuB, ΔqsuD, ΔldhA | aroG(P150L), aroB, aroD, aroE |
| SKM12 | tkt-tal, gapA | ΔaroK, ΔqsuB, ΔqsuD, ΔldhA | aroG(P150L), aroB, aroD, aroE |

*)Mixed sugar utilization genes, namely, xylA gene (xylose isomerase), xylB gene (xylulokinase), araA gene (arabinose isomerase), araB gene (ribulokinase), and araD gene (ribulose-5-phosphate 3-epimerase) of *Escherichia coli* K-12; bglF(V317A) gene (beta-glucosidase) and bglA gene (6-phospho-beta-glucosidase) of *Corynebacterium glutamicum* R; and araE gene (arabinose transporter) of *Corynebacterium glutamicum* ATCC 31831, are introduced into each strain.

For an explanation of gene name abbreviations, see Table 2.

Example 2

Shikimic Acid Production by *Corynebacterium glutamicum* Transformant

Using a shikimic acid-producing strain SKM6 (see Example 1 (Table 3)) constructed based on the A1X5C1araEΔldhA strain, which is a mixed sugar utilization strain obtained from a shikimic acid-producing transformant of *Corynebacterium glutamicum* R, a shikimic acid-production experiment was conducted by aerobic fed-batch reaction with use of a jar fermentor (made by Able Corp., Type: BMJ1L) as described below.

The SKM6 strain was inoculated into 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose dissolved in 1 L of distilled water) containing 20 µg/mL each of phenylalanine, tyrosine, and tryptophan, 10 µg/mL of p-aminobenzoic acid, 50 µg/mL of kanamycin, and 5 µg/mL of chloramphenicol in a test tube, and then aerobically cultured with shaking at 33° C. for 16 hours.

The *Corynebacterium glutamicum* SKM6 strain grown under the conditions as above was inoculated into 100 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042$% (w/v) $MnSO_4 \cdot 2H_2O$, 1 mL of 0.02% (w/v) biotin solution, 2 mL of 0.01% (w/v) thiamin solution, 2 g of yeast extract, 7 g of vitamin assay casamino acid, and 40 g of glucose dissolved in 1 L of distilled water) containing 20 μg/mL each of phenylalanine, tyrosine, and tryptophan, 10 μg/mL of p-aminobenzoic acid, 50 μg/mL of kanamycin, and 5 μg/mL of chloramphenicol in a 500-mL flask, and then aerobically cultured with shaking at 33° C. for 16 hours.

The bacterial cells of the *Corynebacterium glutamicum* SKM6 strain grown under the conditions as above were collected by centrifugation (4° C., 3000×g, 10 min) and suspended at a concentration corresponding to an $OD_{610}$ of 0.5 in 600 mL of A (-urea, 3× ammonium sulfate, 5 μg/L of biotin, 2× yeast extract, 2× vitamin assay casamino acid) liquid medium (21 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042$% (w/v) $MnSO_4 \cdot 2H_2O$, 25 μL of 0.02% (w/v) biotin solution, 2 mL of 0.01% (w/v) thiamin solution, 4 g of yeast extract, and 14 g of vitamin assay casamino acid dissolved in 1 L of distilled water) containing 60 g/L of glucose, 100 mg/L each of phenylalanine, tyrosine, and tryptophan, 50 mg/L of p-aminobenzoic acid, 50 μg/mL of kanamycin, 5 μg/mL of chloramphenicol, and 5 g/L of a defoamant (DISFOAM (registered trademark) CB-442) in a 1000-mL jar fermenter (made by Able Corp., Type: BMJ1L), and then aerobically cultured with stirring under the conditions of 33° C., pH 7.0 (controlled by addition of 5.0 N aqueous ammonia), aeration at 0.6 L/min (air, 1 vvm), and dissolved oxygen level (DO) of 10% (relative to saturated dissolved oxygen level at atmospheric pressure at 100%) for 18 hours.

The bacterial cells of the *Corynebacterium glutamicum* SKM6 strain grown under the conditions as above were collected by centrifugation (4° C., 5000×g, 10 min), washed once with 0.9% sodium chloride aqueous solution, and suspended at a concentration corresponding to 100 g wet bacterial cells/L (10% by weight of wet bacterial cells per medium volume) in 250 mL of BT (-urea, -biotin) liquid medium (7 g of $(NH_4)_2SO_4$, 0.5 g of $KH_2PO_4$, 0.5 g of $K_2HPO_4$, 0.5 g of $MgSO_4 \cdot 7H_2O$, 1 mL of 0.06% (w/v) $Fe_2SO_4 \cdot 7H_2O + 0.042$% (w/v) $MnSO_4 \cdot 2H_2O$, and 2 mL of 0.01% (w/v) thiamin solution dissolved in 1 L of distilled water) containing 10% glucose in a 1000-mL jar fermenter (made by Able Corp., Type: BMJ1L), and then shikimic acid-producing reaction was performed under the conditions of 33° C., pH 7.0 (controlled by addition of 5.0 N aqueous ammonia), aeration at 0.25 L/min (air, 1 vvm), and dissolved oxygen level (DO) of 5% (relative to saturated dissolved oxygen level at atmospheric pressure at 100%). The glucose concentration in the reaction mixture was monitored using a glucose sensor (Oji Scientific Instruments, BF-5i), and glucose replenishment was performed before complete depletion. The aromatic metabolite concentration in the culture supernatant was analyzed by high-performance liquid chromatography (separated using Prominence HPLC device (made by Shimadzu), COSMOSIL Packed column 5C18-AR-II, mobile phase: 20% methanol and 0.07% perchloric acid). The results are shown in Table 4. The SKM6 strain produced 480 mM (83.6 g/L) of shikimic acid (shikimic acid production rate: 20.0 mM/h=3.5 g/L·h), 90.3 mM (15.5 g/L) of 3-DHS, and 6.9 mM (1.3 g/L) of 3-DHQ in 24 hours of reaction. Also, the strain produced only a slight amount (1 mM or less) of quinate, which is known to be a major by-product generated by shikimic acid-producing strains of *Escherichia coli*. Also, the amount of consumed glucose was 1119 mM, and the sugar-based yield (mol/(mol glucose), %) was 42.9% for shikimic acid and 51.6% for shikimic acid combined with 3-DHS and 3-DHQ. In addition, in the reaction of shikimic acid production by the SKM6 strain, bacterial cell growth was not observed. These results show that, in a reaction process where a minimal inorganic salts medium is used and bacterial cells do not grow, the SKM6 strain exhibits an extremely high shikimic acid productivity and an extremely high sugar-based yield. The shikimic acid productivity of the SKM6 strain was significantly higher than that of *Escherichia coli* SP1.1 pts-/pSC6.090B (shikimic acid production rate: 1.8 g/L*h, shikimic acid yield: 27% (Patent Literature 4 (U.S. Pat. No. 6,472,169))), which is known to be the most highly productive recombinant strain of *Escherichia coli* in the fermentation method from sugars using minimal medium. Also, the above shikimic acid-producing strain of *Escherichia coli* is seriously disadvantageous in that quinate as a by-product is produced in a large amount and is hard to separate from shikimic acid in a later step of purification of shikimic acid (Patent Literature 3 (U.S. Pat. No. 6,613,552) and Patent Literature 4 (U.S. Pat. No. 6,472,169)). In contrast, the SKM6 strain of the present invention hardly produced quinate and therefore is advantageous in that the step of purification of shikimic acid is not hindered. Meanwhile, the supernatant of the reaction mixture was subjected to quantitative analysis for organic acids by HPLC (Prominence HPLC (made by Shimadzu), TSK-gel Oapak-A column (made by Tosoh)). As a result, as shown in Table 4, the SKM6 strain remarkably accumulated dihydroxyacetone (DHA) produced by the dephosphorization of dihydroxyacetone phosphate (DHAP), which is a metabolic intermediate in the glycolytic pathway. Regarding organic acids other than DHA, remarkable accumulation was not observed.

Example 3

Effect of Dihydroxyacetone Phosphate (DHAP) Phosphatase Gene (hdpA) Disruption on Shikimic Acid Production As described in Example 2, in the shikimic acid-producing reaction by the SKM6 strain, remarkable accumulation of dihydroxyacetone (DHA) produced by dephosphorization of dihydroxyacetone phosphate (DHAP), which is a metabolic intermediate in the glycolytic system, was observed. Based on the fact, it was assumed that inhibition of DHA production by blocking the DHA biosynthetic pathway would further increase the efficiency of shikimic acid production. To investigate the effect, a strain SKM7 in which the hdpA gene encoding DHAP phosphatase (HAD (haloacid dehalogenase) superfamily phosphatase) was disrupted in addition to the genetic modifications in SKM6 (see Example 1 (Table 3)) was constructed, and an experiment of shikimic acid production using the strain was conducted under the same conditions and in the same manner as in Example 2. As shown in Table 4, the SKM7 strain produced 536 mM (93.3 g/L) of shikimic acid (shikimic acid production rate: 22.3 mM/h=3.9 g/L·h), 97.3 mM (16.7 g/L) of 3-DHS, and 6.9 mM (1.3 g/L) of 3-DHQ in 24 hours of reaction. Also, the amount of consumed glucose was 1136 mM, and the sugar-based yield (mol/mol, %) was 47.2% for shikimic acid and 56.3% for shikimic acid combined with 3-DHS and 3-DHQ. The results show that disruption of the hdpA gene in addition to the genetic modifications in SKM6

(ptsH disruption, higher expression of the genes of non-PTS glucose permease, glucokinase, and GAPDH, etc.) inhibits DHA production, and further increases both the amount of shikimic acid production and the sugar-based yield as compared to those of SKM6 (12% increase in the amount produced and 9% increase in the yield). In contrast, as with the case of SKM6, quinate production was hardly observed. Meanwhile, as shown in Table 4, organic acid analysis showed that DHA production was completely inhibited in the case of SKM7. Also, regarding organic acids other than DHA, remarkable accumulation was not observed. In addition, in the reaction of shikimic acid production by the SKM7 strain, changes in bacterial cell concentration were not observed. These results show that, in a reaction process where bacterial cells do not grow, the SKM7 strain exhibited a further higher shikimic acid productivity and a further higher sugar-based yield than the SKM6 strain.

Comparative Example 1

Effect of Enhancement of GAPDH Activity on Shikimic Acid Production

To investigate the degree of contribution of higher expression of glyceraldehyde-3-phosphate dehydrogenase (GAPDH) gene (gapA) to the shikimic acid-producing ability of the SKM6 strain shown in Example 2, using the SKM5 strain having the same genotype as that of SKM6 except that chromosomal introduction of the gapA gene encoding GAPDH of *Corynebacterium glutamicum* has not been conducted (see Table 3 in Example 1), an experiment of shikimic acid production was conducted under the same conditions and in the same manner as in Example 2. As a result, as shown in Table 4, the SKM5 strain produced 394 mM (68.6 g/L) of shikimic acid (shikimic acid production rate: 16.4 mM/h=2.9 g/L·h), 64.5 mM (11.1 g/L) of 3-DHS, and 5.9 mM (1.1 g/L) of 3-DHQ in 24 hours of reaction. Also, the amount of consumed glucose was 881 mM, and the sugar-based yield (mol/mol, %) was 44.7% for shikimic acid and 52.7% for shikimic acid combined with 3-DHS and 3-DHQ. The results show that the amount of shikimic acid production (Table 4) by the SKM6 strain having the gapA gene introduced thereinto (described in Example 2) was 22% higher than the amount produced by the SKM5 strain and that the higher expression of the GAPDH gene in the transformant leads to remarkably increased shikimic acid production. The SKM6 strain exhibited, as compared to the SKM5 strain, a considerably (27%) increased glucose consumption and a slightly decreased sugar-based yields of shikimic acid and of shikimic acid combined with 3-DHS and 3-DHQ. From these facts, the main cause of the increased shikimic acid productivity of the SKM6 strain is considered to be the increased shikimic acid-production rate associated with the increased glucose consumption. That is, it was shown that the enhancement of the GAPDH activity in the transformant activates the glucose consumption and thereby improves the shikimic acid productivity. At 6 hours after the start of the reaction in the SKM5 strain and the SKM6 strain, a crude enzyme extract was obtained from the bacterial cells of each strain and was measured for the GAPDH activity. As a result, as shown in Table 4, the GAPDH activity of the SKM6 strain (5.4 U/mg protein) was about 4.3 times higher than that of the SKM5 strain (1.3 U/mg protein), which confirmed the enhancement of the GAPDH activity in the SKM6 strain having the chromosomally introduced gapA gene.

Comparative Example 2

Verification on Whether the Shikimic Acid-Productivity Enhancing Effect by Way of Enhancement of GAPDH Activity is Specific to Strains with Enhanced Non-PTS Glucose Permease System As described in Comparative Example 1, it was shown that introduction and higher expression of the glycolytic GAPDH gene (gapA) in addition to ptsH gene disruption, iolT1 gene higher expression, and glucokinase gene (glk1, glk2, and ppgK) higher expression (hereinafter, the combination of these genetic modifications is called "enhancement of non-PTS glucose permease system") facilitates glucose consumption and greatly increases shikimic acid production. To verify whether the shikimic acid-productivity enhancing effect by way of higher expression of the gapA gene is specific to strains with enhanced non-PTS glucose permease system, the effect of gapA gene higher expression was examined using, as a reference, a shikimic acid-producing strain which depends on PTS for intracellular uptake of glucose.

Using SKM11 being a shikimic acid-producing strain having a non-disrupted ptsH gene and SKM12 having the same genotype as that of SKM11 except for highly expressing the gapA gene as a result of chromosomal introduction of the gene under the control of a promoter for high expression (see Example 1 (Table 3); in both of the strains, aroK gene, qsuB gene, and qsuD gene were disrupted, and tkt-tal gene and shikimic acid biosynthetic pathway genes (aroG, aroB, aroD, and aroE) had been introduced), an experiment of shikimic acid production was conducted under the same conditions and in the same manner as in Example 2 except that the bacterial cell concentration for use in the reaction was 50 g wet cells/L (the weight of wet cells was 5% of the medium volume). The DAHP synthase gene introduced into these two strains was aroG(P150L). The mutation site of this gene is different from that of other shikimic acid-producing strains, but it has already been confirmed that the product of this gene has almost the same enzymatic characteristic (feedback inhibition resistance to aromatic amino acids) as that of the DAHP synthase encoded by aroG(S180F), and when introduced into *Corynebacterium glutamicum*, exhibits the same effect on shikimic acid production.

The results show that, as shown in Table 5, the SKM11 strain produced 139 mM of shikimic acid and 24.5 mM of 3-DHS, while the SKM12 strain produced 115 mM of shikimic acid and 17.2 mM of 3-DHS in 24 hours of reaction. At 6 hours after the start of the reaction in the strains, the bacterial cells of each strain were collected, and each crude enzyme extract obtained therefrom was measured for the GAPDH activity. As a result, as shown in Table 5, the GAPDH activity of the SKM12 strain, into which the gapA gene had been introduced, was about 10 times higher than that of the SKM11 strain, which did not have the gene. Therefore, it was confirmed that the GAPDH activity was enhanced in the SKM12 strain. Therefore, it can be said that, when a shikimic acid-producing strain having PTS was used as a reference, enhancement of the GAPDH activity did not increase sugar consumption or shikimic acid production. The fact shows that the improvement of the shikimic acid productivity by way of enhancement of GAPDH activity is specific to transformants of coryneform bacteria which depend on non-PTS glucose permease for glucose transport.

Comparative Example 3

Effects of Enhancement of Non-PTS Glucose Permease System and Enhancement of GAPDH Activity on Shikimic Acid Production To investigate the degree of contribution of the enhancement of non-PTS glucose permease system (ptsH gene disruption, iolT1 gene higher expression, and glucokinase gene (glk1, glk2, and ppgK) higher expression) and of the enhancement of GAPDH activity on the shikimic acid-producing ability of the SKM6 strain shown in Example 2, using the SKM4 strain having the same genotype as that of SKM6 except that none of enhancement of non-PTS glucose permease system and enhancement of GAPDH activity has been performed (see Table 3 in Example 1), an experiment of shikimic acid production was conducted under the same conditions and in the same manner as in Example 2 for the comparison with the productivity of the SPM6 strain. As a result, as shown in Table 4, the SKM4 strain produced 291 mM (50.7 g/L) of shikimic acid (shikimic acid production rate: 12.1 mM/h=2.1 g/L·h), 48.1 mM (8.3 g/L) of 3-DHS, and 4.7 mM (0.9 g/L) of 3-DHQ in 24 hours of reaction. Also, the amount of consumed glucose was 676 mM, and the sugar-based yield (mol/mol, %) was 43.0% for shikimic acid and 50.8% for shikimic acid combined with 3-DHS and 3-DHQ. That is, it was shown that the amount of shikimic acid produced and the amount of glucose consumed by the SKM6 strain were both about 65% higher than those of the SKM4 strain. The results show that the combination of the enhancement of non-PTS glucose permease system and the enhancement of GAPDH activity greatly increases the shikimic acid productivity in association with the glucose consumption.

Comparative Example 4

Effect of Enhancement of Non-PTS Glucose Permease System on Shikimic Acid Production A comparison was made (Table 4) between the SKM4 strain described in the above Comparative Example 3 and the SKM5 strain (Comparative Example 1) in which, in addition to the genetic modifications in SKM4, the enhancement of non-PTS glucose permease system (ptsH gene disruption for blocking the PTS sugar transport, iolT1 gene higher expression, and glucokinase gene (glk1, glk2, and ppgK) higher expression)) was made. The SKM5 strain produced a 35% increased amount of shikimic acid in association with increased amount of glucose consumption as compared to that of the SKM4 strain. That is, it was shown that the enhancement of non-PTS glucose permease system alone also considerably increases the amount of shikimic acid produced.

TABLE 4

Shikimic acid-production experiment by jar fermentor reaction (24-hour reaction)

| Strain | Product concentration (mM) | | | | Shikimic acid production rate (mM/h) | Glucose consumption (mM) | Yield (%, mol/(mol glucose)) | | GAPDH activity (U/mg protein) |
| --- | --- | --- | --- | --- | --- | --- | --- | --- | --- |
| | Shikimic acid | 3-DHS | 3-DHQ | DHA | | | Shikimic acid | Shikimic acid + 3-DHS + 3-DHQ | |
| SKM4 | 291 | 48.1 | 4.7 | 4.3 | 12.1 | 676 | 43.0 | 50.8 | 1.1 |
| SKM5 | 394 | 64.5 | 5.9 | 109 | 16.4 | 881 | 44.7 | 52.7 | 1.3 |
| SKM6 | 480 | 90.3 | 6.9 | 51.9 | 20.0 | 1119 | 42.9 | 51.6 | 5.4 |
| SKM7 | 536 | 97.3 | 6.9 | 0.0 | 22.3 | 1136 | 47.2 | 56.3 | 5.7 |

TABLE 5

Effect of enhanced GAPDH activity in shikimic acid-producing strains having PTS (24-hour reaction)

| Strain | Product concentration (mM) | | Glucose consumption (mM) | Yield (%, mol/(mol glucose)) | | GAPDH activity (U/mg protein) |
| --- | --- | --- | --- | --- | --- | --- |
| | Shikimic acid | 3-DHS | | Shikimic acid | Shikimic acid + DNS | |
| SKM11 | 139 | 24.5 | 312 | 44.4 | 52.3 | 0.8 |
| SKM12 | 115 | 17.2 | 256 | 44.9 | 51.7 | 8.0 |

Shikimic Acid Production Using Mixed Sugars as Carbon Sources

The shikimic acid-producing strain constructed in the present invention, into which strain genes for mixed sugar utilization have been introduced, can simultaneously utilize xylose, arabinose, and cellobiose, in addition to glucose (Sasaki, M., et al, Engineering of pentose transport in *Corynebacterium glutamicum* to improve simultaneous utilization of mixed sugars. Appl. Microbiol. Biotechnol. 85: 105-115 (2009)). To confirm this, with the use of the SKM7 strain, an experiment of shikimic acid production was conducted using mixed sugars of glucose, xylose, and arabinose as carbon sources. The shikimic acid-production experiment was conducted under the same conditions and in the same manner as in Example 2 except that the medium used for the reaction contained 60 g/L of glucose, 35 g/L of xylose, and 5 g/L of arabinose (initial concentrations) as carbon sources.

(When the concentrations of the carbon sources decreased, the three kinds at the same ratio as above were added before depletion.)

As a result, as shown in Table 6, the SKM7 strain produced 518 mM (90.2 g/L) of shikimic acid (shikimic acid production rate: 21.6 mM/h=3.8 g/L·h), 122 mM (21.0 g/L) of 3-DHS, and 6.7 mM (1.3 g/L) of 3-DHQ in 24 hours of reaction. In the reaction, 656 mM of glucose, 497 mM of xylose, and 75 mM of arabinose were consumed, and therefore, the sugar-based yield (mol/mol, %) was 45.8% for shikimic acid and 57.2% for shikimic acid combined with 3-DHS and 3-DHQ.

Thus, it was shown that the SKM7 strain exhibits almost the same level of shikimic acid-productivity and yield based on sugar even in a reaction using mixed sugars of glucose, xylose, and arabinose as carbon sources as in a reaction using glucose as a single carbon source. Also, it was confirmed that the transformant is capable of simultaneously utilizing the sugars.

TABLE 6

Shikimic acid-production experiment using mixed sugars as carbon sources by jar fermentor reaction (24-hour reaction)

| Strain | Product concentration (mM) | | | Shikimic acid production rate (mM/h) | Sugar consumption (mM) | | | Yield (%, mol/mol$^a$) | |
|---|---|---|---|---|---|---|---|---|---|
| | Shikimic acid | 3-DHS | 3-DHQ | | Glucose | Xylose | Arabinose | Shikimic acid | Shikimic acid + 3-DHS + 3-DHQ |
| SKM7 | 518 | 122 | 6.7 | 21.6 | 656 | 497 | 75.0 | 45.8 | 57.2 |

$^a$The rate of [amount produced] relative to [sugar consumption (6 mol of xylose or arabinose is converted to 5 mol of glucose)] is expressed in percentage.

Comparative Example 5

Effect of Enhancement of 3-Deoxy-D-Arabino-Heptulosonate-7-Phosphate (DAHP) Synthase Activity on Shikimic Acid Production To examine the effect of the enhancement of DAHP synthase activity on shikimic acid production by *Corynebacterium glutamicum* transformants, the shikimic acid productivity of the SKM2 strain and the SKM3 strain (see Example 1, Table 2 and Table 3) were compared. The SKM3 strain is a strain into which, in addition to the genetic modifications in SKM2 (disruption of aroK gene, qsuB gene, and qsuD gene, and higher expression of tkt gene and tal gene), a feedback inhibition-resistant DAHP synthase gene (aroG (S180F)) of *Escherichia coli* has been introduced using a plasmid. The SKM2 strain and the SKM3 strain were separately inoculated into 10 mL of A liquid medium (2 g of $(NH_2)_2CO$, 7 g of $(NH_4)_2SO_4$, 0.5 g of $KH_2PO_4$, 0.5 g of $K_2HPO_4$, 0.5 g of $MgSO_4.7H_2O$, 1 mL of 0.06% (w/v) $Fe_2SO_4.7H_2O$+0.042% (w/v) $MnSO_4.2H_2O$, 1 mL of 0.02% (w/v) biotin solution, 2 mL of 0.01% (w/v) thiamin solution, 2 g of yeast extract, 7 g of vitamin assay casamino acid, and 40 g of glucose dissolved in 1 L of distilled water) containing 20 μg/mL each of phenylalanine, tyrosine, and tryptophan, and 10 μg/mL of p-aminobenzoic acid (and 50 μg/mL (final concentration) of kanamycin for the culture of the SKM3 strain) in a test tube, and then aerobically cultured with shaking at 33° C. for 16 hours.

The bacterial cells grown in the above conditions were inoculated at a concentration corresponding to an $OD_{610}$ of 0.5 into 10 mL of A liquid medium containing 20 μg/mL each of phenylalanine, tyrosine, and tryptophan, and 10 μg/mL of p-aminobenzoic acid (and 50 μg/mL (final concentration) of kanamycin for the culture of the SKM3 strain) in a test tube, and aerobically cultured with shaking at 33° C. for 24 hours. After 24 hours of culture, the culture medium was centrifuged (4° C., 15,000 rpm for 5 minutes), and the obtained supernatant was subjected to high-performance liquid chromatography (HPLC) to quantify related aromatic compounds including shikimic acid. The test results are shown in Table 7. The SKM2 strain produced 10.2 mM of shikimic acid and 2.5 mM of 3-DHS (sugar-based yield of shikimic acid and the total sugar-based yield of shikimic acid and 3-DHS were 8.6% and 10.6%, respectively), while the SKM3 strain produced 18.9 mM of shikimic acid and 6.6 mM of 3-DHS (sugar-based yield of shikimic acid and the total sugar-based yield of shikimic acid and 3-DHS were 16.0% and 21.9%, respectively) in 24 hours of aerobic culture. The amounts of 3-DHQ produced by the two strains were both very slight (1 mM or less). The results show that higher expression of the feedback inhibition-resistant DAHP synthase gene (aroG(S180F)) of *Escherichia coli* greatly increases the amounts of shikimic acid and 3-DHS produced.

Comparative Example 6

Effect of Activity Enhancement of Shikimic Acid Biosynthetic Pathway on Shikimic Acid Production To examine the effects of activity enhancement of the shikimic acid biosynthetic pathway genes (aroB, aroD, aroE) encoding 3-dehydroquinate (3-DHQ) synthase, 3-DHQ dehydratase, and shikimate dehydrogenase, which sequentially catalyze the conversion from DAHP to shikimic acid in the shikimic acid production by *Corynebacterium glutamicum* transformants, using the SKM4 strain in which the genes are highly expressed as a result of plasmid introduction (see Example 1 (Table 3)), an experiment of shikimic acid production was conducted under the same conditions and in the same manner as in the above-described Comparative Example 5. (For the culture of the SKM4 strain, 50 μg/mL (final concentration) of kanamycin and 5 μg/mL (final concentration) of chloramphenicol were added to the culture medium.)

As a result, as shown in Table 7, the SKM4 strain produced 28.8 mM of shikimic acid and 4.9 mM of 3-DHS (sugar-based yield of shikimic acid and the total sugar-based yield of shikimic acid and 3-DHS were 28.7% and 33.0%, respectively). Comparison of these results and the results of the SKM3 strain not having the aroB gene, the aroD gene, or the aroE gene introduced thereinto (described in Comparative Example 5) show that the SKM4 strain produced a greatly (52%) increased amount of shikimic acid. Meanwhile, the SKM4 strain produced a 26% reduced amount of 3-DHS as compared to the SKM3 strain. These results show that higher expression of the shikimic acid biosynthetic pathway genes (aroB, aroD, aroE) facilitates the conversion from 3-DHS to shikimic acid and greatly increases the amount of shikimic acid produced.

Comparative Example 7

Effect of Enhancement of Transketolase Activity and Transaldolase Activity on Shikimic Acid Production To examine the effect of activity enhancement of the transketolase gene (tkt) and the transaldolase gene (tal) involved in supplying erythrose-4-phosphate (E4P), which is a precursor of shikimic acid in the shikimic acid production by Corynebacterium glutamicum transformants, comparisons were made between the SKM1 strain and the SKM2 strain, and between the SKM10 strain and the SKM4 strain (see Example 1 (Table 2, Table 3)) in their shikimic acid productivity.

Using the SKM1 strain and the SKM10 strain, an experiment of shikimic acid production was conducted under the same conditions and in the same manner as in Comparative Example 5. As a result, as shown in Table 7, the SKM1 strain, into which the tkt-tal gene had not been introduced, produced 10.0 mM of shikimic acid and 1.6 mM of 3-DHS in 24 hours of culture. It was shown that the amount of shikimic acid produced by the SKM1 strain was almost equal to that of the SKM2 strain described in Comparative Example 5, into which strain the tkt-tal gene had been introduced (Table 7). Therefore, it was shown that the introduction of the tkt-tal gene in the genotype common to these two strains did not significantly increase the amount of shikimic acid produced.

Meanwhile, the SKM10 strain, into which the shikimic acid biosynthetic pathway genes had been introduced and were highly expressed but the tkt-tal gene had not been introduced, produced 20.2 mM of shikimic acid and 2.0 mM of 3-DHS, and the sugar-based yield of shikimic acid was 21.7% in 24 hours of culture. Comparison of these results and the productivity of the SKM4 strain having both the shikimic acid biosynthetic pathway genes and the tkt-tal gene introduced thereinto (Table 7) as described in Comparative Example 6 shows that the amount of shikimic acid produced and the yield of SKM4 were both greatly (43% and 32%, respectively) increased. Therefore, it was shown that in the cases where the shikimic acid biosynthetic pathway genes (aroG, aroB, aroD, and aroE) are highly expressed, higher expression of the tkt-tal gene exhibits a remarkable effect of increasing shikimic acid productivity in a transformant having an enhanced carbon flux to the shikimic acid biosynthetic pathway.

Comparative Example 8

Effect of Disruption of Shikimate Kinase Gene, 3-Dehydroshikimate (3-DHS) Dehydratase Gene, and Quinate/Shikimate Dehydrogenase Gene on Shikimic Acid Production To examine the effects of disruption of chromosomal genes each encoding shikimate kinase, 3-dehydroshikimate (3-DHS) dehydratase, and quinate/shikimate dehydrogenase (the disruption was made for the purpose of inhibiting the metabolism by the enzymes, the metabolism leading to consumption of shikimic acid (and 3-DHS)) in Corynebacterium glutamicum transformants on shikimic acid production, the shikimic acid productivity was compared among the A1X5C1araEΔldhA strain (the original strain of the shikimic acid-producing strains, a mixed sugar utilization strain), the SKM1 strain, the SKM8 strain, and the SKM9 strain (see Example 1, Table 3).

Using the A1X5C1araEΔldhA strain, the SKM8 strain, and the SKM9 strain, an experiment of shikimic acid production by culture in test tubes was conducted under the same conditions and in the same manner as in Comparative Example 5 except that the antibiotic was not added to the medium. As a result, as shown in Table 7, the A1X5C1araEΔldhA strain, the SKM8 strain, and the SKM9 strain hardly produced shikimic acid and 3-DHS (each produced 0.3 mM and 0.1 mM, respectively), while the SKM1 strain produced 10.0 mM of shikimic acid and 1.6 mM of 3-DHS. These results show that the original strain, the qsuB gene disruptant, and the qsuB/qsuD double gene disruptant of the shikimic acid-producing strain hardly accumulate shikimic acid, while the disruption of the gene encoding shikimate kinase (aroK) present on the main metabolic pathway of shikimic acid remarkably increases the amount of shikimic acid produced.

TABLE 7

Shikimic acid-production experiment by test-tube culture (24-hour reaction)

| Strain | Amount produced (mM) | | Glucose consumption (mM) | Yield (%, mol/mol glucose) | |
| --- | --- | --- | --- | --- | --- |
| | Shikimic acid | 3-DHS | | Shikimic acid | Shikimic acid + 3-DHS |
| A1X5C1-araEΔldhA | 0.3 | 0.1 | 93 | 0.3 | 0.4 |
| SKM1 | 10.0 | 1.6 | 122 | 6.9 | 8.0 |
| SKM2 | 10.2 | 2.5 | 116 | 8.6 | 10.6 |
| SKM3 | 18.9 | 6.6 | 97 | 16.0 | 21.9 |
| SKM4 | 28.8 | 4.9 | 100 | 28.7 | 33.0 |
| SKM8 | 0.4 | 0.1 | 108 | 0.3 | 0.4 |
| SKM9 | 0.4 | 0.1 | 108 | 0.3 | 0.4 |
| SKM10 | 20.2 | 2.0 | 93 | 21.7 | 23.8 |

INDUSTRIAL APPLICABILITY

According to the process of the present invention, using microorganisms, organic compounds, such as shikimic acid, can be produced from glucose or the like with a practical efficiency.

The invention claimed is:

1. A coryneform bacterium transformant engineered by the following (A) to (D):
 (A) enhancement of 3-deoxy-D-arabino-heptulosonate-7-phosphate (DAHP) synthase activity by introducing a DNA that encodes the DHAP;
 (B) prevention, inhibition, or reduction of intracellular sugar uptake mediated by phosphoenolpyruvate:sugar phosphotransferase system (PTS);
 (C) enhancement of intracellular sugar uptake activity mediated by a sugar transporter different from phosphoenolpyruvate:sugar phosphotransferase system and enhancement of glucokinase activity by introducing a DNA that encodes the glucokinase; and
 (D) enhancement of glyceraldehyde-3-phosphate dehydrogenase (GAPDH) activity by introducing a DNA that encodes the GAPDH.

2. The coryneform bacterium transformant of claim 1, wherein dihydroxyacetone phosphate phosphatase activity is prevented, inhibited, or reduced.

3. The coryneform bacterium transformant of claim 1, wherein one or more of 3-dehydro-quinate synthase activity, 3-dehydro-quinate dehydratase activity, and shikimate dehydrogenase activity are enhanced.

4. The coryneform bacterium transformant of claim 1, wherein one or more of transketolase activity and transaldolase activity are enhanced.

5. The coryneform bacterium transformant of claim 1, wherein one or more of shikimate kinase activity, quinate/shikimate dehydrogenase activity, and 3-dehydroshikimate dehydratase activity are prevented, inhibited, or reduced.

6. The coryneform bacterium transformant of claim 1, which is capable of utilizing glucose and at least one kind of sugar selected from the group consisting of xylose, arabinose, and cellobiose.

7. The coryneform bacterium transformant of claim 1, wherein 3-deoxy-D-arabino-heptulosonate-7-phosphate synthase activity is enhanced by a DNA introduced thereinto, the DNA being
 (a) a DNA consisting of the base sequence of SEQ ID NO: 1; or
 (b) a DNA consisting of a base sequence which has 90% or more of identity with the base sequence of SEQ ID NO: 1 and encodes 3-deoxy-D-arabino-heptulosonate-7-phosphate synthase.

8. The coryneform bacterium transformant of claim 1, wherein intracellular sugar uptake mediated by phosphoenolpyruvate:sugar phosphotransferase system (PTS) is prevented, inhibited, or reduced by disruption, deletion, or mutation of one or more of ptsH encoding histidine-phosphorylatable protein (HPr), ptsI encoding Enzyme I, and ptsG encoding glucose-specific Enzyme II as genes encoding components of PTS.

9. The coryneform bacterium transformant of claim 1, wherein the sugar transporter different from phosphoenolpyruvate:sugar phosphotransferase system (PTS) is an inositol transporter.

10. The coryneform bacterium transformant of claim 9, wherein the intracellular sugar uptake activity mediated by the inositol transporter is enhanced by a DNA introduced thereinto, the DNA being
 (c) a DNA consisting of the base sequence of SEQ ID NO: 2; or
 (d) a DNA consisting of a base sequence which has 90% or more of identity with the base sequence of SEQ ID NO: 2 and encodes the inositol transporter.

11. The coryneform bacterium transformant of claim 1, wherein the glucokinase activity is enhanced by a DNA introduced thereinto, the DNA being
 (e) a DNA consisting of the base sequence of SEQ ID NO: 3, 4, or 5; or
 (f) a DNA consisting of a base sequence which has 90% or more of identity with the base sequence of SEQ ID NO: 3, 4, or 5 and encodes glucokinase.

12. The coryneform bacterium transformant of claim 1, wherein the glyceraldehyde-3-phosphate dehydrogenase activity is enhanced by a DNA introduced thereinto, the DNA being
 (g) a DNA consisting of the base sequence of SEQ ID NO: 6; or
 (h) a DNA consisting of a base sequence which has 90% or more of identity with the base sequence of SEQ ID NO: 6 and encodes glyceraldehyde-3-phosphate dehydrogenase.

13. The coryneform bacterium transformant of claim 3, wherein the enhancement of the 3-dehydro-quinate synthase activity is achieved by introducing
 (i) a DNA consisting of the base sequence of SEQ ID NO: 7 or (j) a DNA consisting of a base sequence which has 90% or more of identity with the base sequence of SEQ ID NO: 7 and encodes 3-dehydro-quinate synthase;

the enhancement of the 3-dehydro-quinate dehydratase activity is achieved by introducing (k) a DNA consisting of the base sequence of SEQ ID NO: 8 or (l) a DNA consisting of a base sequence which has 90% or more of identity with the base sequence of SEQ ID NO: 8 and encodes 3-dehydro-quinate dehydratase; and the enhancement of the shikimate dehydrogenase activity is achieved by introducing (m) a DNA consisting of the base sequence of SEQ ID NO: 9 or (n) a DNA consisting of a base sequence which has 90% or more of identity with the base sequence of SEQ ID NO: 9 and encodes shikimate dehydrogenase.

14. The coryneform bacterium transformant of claim 4, wherein the enhancement of the transketolase activity is achieved by introducing (o) a DNA consisting of the base sequence of SEQ ID NO: 10 or (p) a DNA consisting of a base sequence which has 90% or more of identity with the base sequence of SEQ ID NO: 10 and encodes transketolase; and the enhancement of the transaldolase activity is achieved by introducing (q) a DNA consisting of the base sequence of SEQ ID NO: 11 or (r) a DNA consisting of a base sequence which has 90% or more of identity with the base sequence of SEQ ID NO: 11 and encodes transaldolase.

15. The coryneform bacterium transformant of claim 1, wherein the coryneform bacterium is *Corynebacterium glutamicum*.

16. The coryneform bacterium transformant of claim 15, which is *Corynebacterium glutamicum* R (FERM BP-18976), ATCC13032, or ATCC13869 strain engineered as described above.

17. *Corynebacterium glutamicum* SKM7 (Accession Number: NITE BP-01903).

18. A process for producing an organic compound, which comprises a step of culturing the transformant of claim 1 in a reaction mixture containing a sugar, and a step of recovering at least one kind of organic compound selected from the group consisting of shikimic acid, 3-dehydroshikimic acid, 3-dehydroquinic acid, protocatechuic acid, chorismic acid, gallic acid, phenylalanine, tyrosine, tryptophan, anthranilic acid, p-hydroxybenzoic acid, p-aminobenzoic acid, phenol, and catechol from the reaction mixture.

19. The process of claim 18, wherein the coryneform bacterium transformant is cultured under aerobic conditions where the coryneform bacterium transformant does not grow.

20. The coryneform bacterium transformant of claim 2, wherein one or more of 3-dehydroquinate synthase activity, 3-dehydroquinate dehydratase activity, and shikimate dehydrogenase activity are enhanced;

one or more of transketolase activity, and transaldolase activity are enhanced; and one or more of shikimate kinase activity, quinate/shikimate dehydrogenase activity, and 3-dehydroshikimate dehydratase activity are prevented, inhibited, or reduced.

21. The coryneform bacterium transformant of claim 3, wherein one or more of transketolase activity and transaldolase activity are enhanced; and one or more of shikimate kinase activity, quinate/shikimate dehydrogenase activity, and 3-dehydroshikimate dehydratase activity are prevented, inhibited, or reduced.

* * * * *

```
                         SEQUENCE LISTING

<160> NUMBER OF SEQ ID NOS: 95

<210> SEQ ID NO 1
<211> LENGTH: 1053
<212> TYPE: DNA
<213> ORGANISM: Escherichia coli

<400> SEQUENCE: 1
atgaattatc agaacgacga tttacgcatc aaagaaatca aagagttact tcctcctgtc      60
gcattgctgg aaaaattccc cgctactgaa aatgccgcga atacggttgc ccatgcccga     120
aaagcgatcc ataagatcct gaaaggtaat gatgatcgcc tgttggttgt gattggccca     180
tgctcaattc atgatcctgt cgcggcaaaa gagtatgcca ctcgcttgct ggcgctgcgt     240
gaagagctga agatgagct ggaaatcgta atgcgcgtct attttgaaaa gccgcgtacc     300
acggtgggct ggaaagggct gattaacgat ccgcatatgg ataatagctt ccagatcaac     360
gacggtctgc gtatagcccg taaattgctg cttgatatta cgacagcgg tctgccagcg     420 gcaggtgagt ttctcgatat gatcacccca caatatctcg ctgacctgat gagctggggc     480
gcaattggcg cacgtaccac cgaatcgcag gtgcaccgcg aactggcatc agggcttttt     540
tgtccggtcg gcttcaaaaa tggcaccgac ggtacgatta agtggctat cgatgccatt     600 aatgccgccg gtgcgccgca ctgcttcctg tccgtaacga aatgggggca ttcggcgatt     660
gtgaatacca gcggtaacgg cgattgccat atcattctgc gcggcggtaa agagcctaac     720
tacagcgcga agcacgttgc tgaagtgaaa gaagggctga acaaagcagg cctgccagca     780
caggtgatga tcgatttcag ccatgctaac tcgtccaaac aattcaaaaa gcagatggat     840
gtttgtgctg acgtttgcca gcagattgcc ggtggcgaaa aggccattat ggcgtgatg     900 gtggaaagcc atctggtgga aggcaatcag agcctcgaga gcggggagcc gctggcctac     960
ggtaagagca tcaccgatgc ctgcatcggc tgggaagata ccgatgctct gttacgtcaa    1020
ctggcgaatg cagtaaaagc gcgtcgcggg taa                                 1053

<210> SEQ ID NO 2
<211> LENGTH: 1476
<212> TYPE: DNA
<213> ORGANISM: Corynebacterium glutamicum

<400> SEQUENCE: 2
atggctagta ccttcattca ggccgacagc cctgaaaaaa gtaagaagct accccactc       60 acagaaggtc cgtatagaaa gcggctgttc tacgttgcac tagttgcgac gtttggtggg     120
ctgctcttcg gatatgacac cggagtaatc aacggtgcac tcaacccaat gacacgtgag     180
ctcggactaa ccgcgttcac cgagggtgtt gtaacttctt ccctgctgtt tggtgcagca     240
gctggtgcga tgttttcgg tcgcatttcc gacaactggg tcgccggaa aacaatcatc      300 tcacttgcag tagctttctt tgtcggcacc atgatctgcg tgtttgctcc atctttgca     360 gtaatggttg tcggacgtgt gcttcttgga ctcgcagttg gtgcgcttc cactgttgtc     420 cctgtctacc tggctgaact tgctcctttt gaaatccgtg gctcactggc tggccgtaat    480
gagttgatga ttgttgttgg tcagctcgca gctttcgtca tcaatgcgat tattggaaat    540
```

-continued

```
gtttttggac accacgatgg tgtgtggcgc tacatgctgg caattgccgc aatcccagca      600
attgccctct tctttggaat gctccgagtt ccagaatccc cacgctggct tgttgagcga      660
ggacgcattg atgaggctcg cgcagttctt gaaaccattc gccctctaga acgtgcccat      720
gcagaagttg ctgatgttga gcacctagca aagaagagc acgccatttc cgagaagtcc      780
atgggcttaa gggaaatttt gtccagcaag tggcttgtgc gcatcctcct ggtaggtatc      840
ggattgggtg tcgcacagca gctgactggc atcaactcca tcatgtacta cggccaggtt      900
gttctcattg aggctggttt ctccgaaaat gcagctctga tcgccaacgt ggcgccagga      960
gtgatcgcag ttgtcggtgc atttatcgca ctgtggatga tggatcgcat caaccgccgt     1020
accaccctca ttaccggcta ctctctcact accattagcc acgtgttgat cggcatcgca     1080
tccgtagcat tctcagtcgg cgatccactt cgcccatacg ttattttgac cctagttgtg     1140
atcttcgtag gatccatgca gaccttcctc aacgtagcca cctgggtcat gctctccgag     1200
ctcttcccgc tggcaatgcg aggtttcgca atcggtatct cagtgttctt cctctggatc     1260
gcaaacgcgt tcctcggatt gttcttcccc accatcatgg aagcagtagg actaaccgga     1320
accttcttca tgttcgccgg aatcggtgtg gttgccttga tcttcatcta cacccaggtt     1380
cctgaaactc gtggacgtac cttggaggag attgatgagg atgttacttc cggtgtcatt     1440
ttcaacaagg acatccgaaa aggaaaggtg cactaa                               1476
```

<210> SEQ ID NO 3
<211> LENGTH: 972
<212> TYPE: DNA
<213> ORGANISM: Corynebacterium glutamicum

<400> SEQUENCE: 3

```
atgccacaaa aaccggccag tttcgcggtg ggctttgaca tcggcggcac caacatgcga       60
gctgggcttg tcgacgaatc cgggcgcatc gtgaccagtt tgtcggcgcc gtcgccgcgc      120
acgacgcagg caatggaaca ggggattttt gatctagtcg aacagctcaa ggccgaatac      180
ccggttggtg ctgtgggact tgccgtcgcg ggatttttgg atcctgagtg cgaggttgtt      240
cgatttgccc cgcaccttcc ttggcgcgat gagccagtcg gtgaaaagtt ggaaaacctt      300
ttgggcctgc ctgttcgttt ggaacatgat gccaactcag cagcgtgggg tgagcatcgt      360
tttggtgcag ctcaaggcgc tgacaactgg gttttgttgg cactcggcac tggaattggt      420
gcagcgctga ttgaaaaagg cgaaatttac cgtggtgcat atggcacggc accagaattt      480
ggtcatttgc gtgttgttcg tggcggacgc gcatgtgcgt gtggcaaaga aggctgcctg      540
gagcgttact gttccggtac tgccttggtt tacactgcgc gtgaattggc ttcgcatggc      600
tcattccgca acagcgggct gtttgacaag atcaaagccg atccgaattc catcaatgga      660
aaaacgatca ctgcggcagc gcgccaagaa gacccacttg ctctcgccgt tctggaagat      720
ttcagcgagt ggctgggcga aactttggcg atcattgctg atgtccttga cccaggtatg      780
atcatcattg gtggcggact gtccaatgct gccgaccttt atttggatcg ctcggttaac      840
cactattcca cccgcatcgt cggcgcagga tatcgcccctt tggcacgcgt tgccacagct      900
cagttgggtg cggatgctgg catgatcggt gtcgctgatc tggctcgacg ttccgtgttg      960
gaagccaact ag                                                         972
```

<210> SEQ ID NO 4
<211> LENGTH: 912
<212> TYPE: DNA

<213> ORGANISM: Corynebacterium glutamicum

<400> SEQUENCE: 4

```
atgactgatc ccacttgcac ccttgccctt gatattggtg ccacaaagat tgcctacgca      60
ctagtccccg ataacgcccc gacgacaaca ttgtccacgg gacgcttggg aacaaaagaa     120
ggcgacagcc ctatcgagca gatccggctg gttcttctgg caggcttaaa agctgccgag     180
gaacacggtc tcagtgtcgc ccgcatcggc atgggcgctc tggtgtaat tctgggacca     240
gagggaacca tcgtgtacaa cggtgaaacc ctcacagagt gggcaggcac tgacctgcga     300
ggattatccc gagaagtcct caacgttcca ttcgcggcac acaatgatgt ccgcgtatgg     360
gcctacggtg agcaccactt aggcaccggc aaagacctca ccggcagggt tctctacgtg     420
tccctcggca ctggagtcgg cggagcaatc atcgaagacg aatcatgat gagtagcccc     480
actgaactg cgggagaatt cgcagaagtt gtgtgctctg accatgcagg attagccgtt     540
cggtgcgaaa atgtagcaag tggcaccggc ctaaccaggt actacaacga ggccgccgca     600
actcaacttg accttccgc catcatggag cgcttccacc aaggtgacgg cctggcacag     660
caaatcatta ctggaaatct ccgaggcttt ggccaagcgc taggcgcatt agtcacagtg     720
ctggaccttt ccgcagtagt agttggaggc ggagtcgcag gcatcggcgc accgtcatg      780
gatcccatca ccgcagggat tttcgatcga atgttagccc ccaacaaatc cgtacaagtt     840
ttaagcacgt cccttggtgc ccaagcagcc gtcatcgcag cagcaaaata tgcccgcgat     900
aacgcctttt aa                                                          912
```

<210> SEQ ID NO 5
<211> LENGTH: 1233
<212> TYPE: DNA
<213> ORGANISM: Corynebacterium glutamicum

<400> SEQUENCE: 5

```
gtggcgcgcg gcggtgtaca gcaccccggt gaccacattg atcacagcac ctgctacgac      60
ctcgccgtcg atcgccgcag cgatcgagac ggcgtattgg ggcaggccat aaaggaagtt     120
gacggtgccg tcaatggggt cgacgatcca ggtaactccg cttatcgacg ccgtccccgt     180
cccttcctcg cctatcagcc cgtctttagg ccgaagttcc tgcaacctat tggcgataaa     240
atcttcagcc aaagtatcta ctatcgtcac cggatcgact gtcgaacttt tggtgttggt     300
gtagtcccac aaattggtga gttcagcacg tttatccctg atacgtgtag cggtaagcgt     360
ggcagtttcc gcggcgatgg cacgcaactc attaaacgat tgttgttcca taagaccatc     420
atcgttgttt ttttagaaaa ttgcctgcca aaagccgaag taatttgtac acttgggcgc     480
atgactgaga ctggatttgg aattgatatc ggtggctccg gcatcaaagg cgcccgcgtt     540
aaccttaaga ccggtgagtt tattgatgaa cgcataaaaa tcgccacccc taagccagca     600
accccagagg ctgtcgccga agtagtcgca gagattattt ctcaagccga atgggagggt     660
ccggtcggaa ttaccctgcc gtctgtcgtt cgcgggcaga tcgcgctatc cgcagccaac     720
attgacaagt cctggatcgg caccgatgtg cacgaacttt ttgaccgcca cctaaatggc     780
cgagagatca ccgttctcaa tgacgcagac gccgccggca tcgccgaagc aacctttggc     840
aacgctgccg cacgcgaagg cgcagtcatc ctgctgaccc ttggtacagg tattggatcc     900
gcattccttg tggatggcca actgttcccc aacacagaac tcggtcacat gatcgttgac     960
ggcgaggaag cagaacacct tgcagcagca gccgtcaaag aaaacgaaga tctgtcatgg   1020
aagaaatggg cgaagcgcct gaacaaggtg ctgagcgaat acgagaaact tttctcccca   1080
```

| | | | |
|---|---|---|---|
| tccgtcttca | tcatcggtgg | cggaatttcc agaaagcacg aaaagtggct tccattgctg | 1140 |
| gagctagaca | ctgacattgt | cccagctgag ctgcgcaatc gagccggaat cgtaggagct | 1200 |
| gccatggcag | taaaccaaca | cctcaccca taa | 1233 |

<210> SEQ ID NO 6
<211> LENGTH: 1005
<212> TYPE: DNA
<213> ORGANISM: Corynebacterium glutamicum

<400> SEQUENCE: 6

| | | | | |
|---|---|---|---|---|
| atgaccattc | gtgttggtat | taacggattt | ggccgtatcg gacgtaactt cttccgcgca | 60 |
| gttctggagc | gcagcgacga | tctcgaggta | gttgcagtca acgacctcac cgacaacaag | 120 |
| accctttcca | cccttctcaa | gttcgactcc | atcatgggcc gccttggcca ggaagttgaa | 180 |
| tacgacgatg | actccatcac | cgttggtggc | aagcgcatcg ctgtttacgc agagcgcgat | 240 |
| ccaaagaacc | tggactgggc | tgcacacaac | gttgacatcg tgatcgagtc caccggcttc | 300 |
| ttcaccgatg | caaacgcggc | taaggctcac | atcgaagcag gtgccaagaa ggtcatcatc | 360 |
| tccgcaccag | caagcaacga | agacgcaacc | ttcgtttacg gtgtgaacca cgagtcctac | 420 |
| gatcctgaga | ccacaacgt | gatctccggc | gcatcttgca ccaccaactg cctcgcacca | 480 |
| atggcaaagg | tcctgaacga | caagttcggc | atcgagaacg gcctcatgac caccgttcac | 540 |
| gcatacaccg | gcgaccagcg | cctgcacgat | gcacctcacg gcgacctgcg tcgtgcacgt | 600 |
| gcagcagcag | tcaacatcgt | tcctacctcc | accggtgcag ctaaggctgt tgctctggtt | 660 |
| ctcccagagc | tcaagggcaa | gcttgacggc | tacgcacttc gcgttccagt tatcaccggt | 720 |
| tccgcaaccg | acctgacctt | caacaccaag | tctgaggtca ccgttgagtc catcaacgct | 780 |
| gcaatcaagg | aagctgcagt | cggcgagttc | ggcgagaccc tggcttactc cgaagagcca | 840 |
| ctggtttcca | ccgacatcgt | ccacgattcc | cacggctcca tcttcgacgc tggcctgacc | 900 |
| aaggtctccg | gcaacaccgt | caaggttgtt | tcctggtacg acaacgagtg gggctacacc | 960 |
| tgccagctcc | tgcgtctgac | cgagctcgta | gcttccaagc tctaa | 1005 |

<210> SEQ ID NO 7
<211> LENGTH: 1098
<212> TYPE: DNA
<213> ORGANISM: Corynebacterium glutamicum

<400> SEQUENCE: 7

| | | | | |
|---|---|---|---|---|
| atgagcgcag | cgcagatttt | caacaccgtc | cacgtcaatg gatcttcccc ctatgatgtc | 60 |
| cacattggtt | ccggcctcaa | cgagctcatt | gttcagcgcg cagcggaatc aggcgcggag | 120 |
| caggtagcga | ttttgcacca | gcccagcatg | gatgacattg catccgagtt ggatgcagca | 180 |
| ctagtcgctg | ctggtttgaa | ggtcctgcac | cttaatgttc ccgatgcgga aaacggcaag | 240 |
| tccttggaag | tagcggggca | gtgctgggat | gaattgggtg gcgcagcatt cggccgccgc | 300 |
| gatatcgtca | tcggacttgg | tggcggtgct | gccacagatc tcgcgggatt cgtcgctgct | 360 |
| gcgtggatgc | gtggcgtgcg | cgtcattcag | gttccaacca ccttgttggc catggtggac | 420 |
| gctgcggtgg | gcggcaagac | tggcatcaat | accgccgcag gcaagaacct tgtgggcgcg | 480 |
| ttccacgagc | ctgacgcagt | attcattgac | accgaacgcc tagccaccct gcctgacgcg | 540 |
| gaaatcatcg | cggatccgc | cgaaatcatc | aaaaactggt tcatcgccga cccagaaatc | 600 |
| ctgcgcccttt | acgaaactga | tcccgcagcc | tgcctgaaga aagaagtcga aggctcccac | 660 |

```
ctacctgaac tgatttggcg ctccgtcacc gtcaagggct ccgtggtcgg ccaagacctc      720
aaagaatcta gcctgcgcga aatcctcaac tacggacaca cctttgccca cgccgtcgaa      780
ctccgcgaaa acttccgctg gcgccacggc aatgccgttg cagtgggcat gatgttcatc      840
gctaacctct cccacaagct cgggcttatc gacgcgcccc tcctcgagcg ccaccgctca      900
atcctggcgg ccatcggtct gcccacttcc tacgaaggcg gagccttcga cgagctttac      960
gacggcatga cccgcgacaa gaaaaaccgc gacggcaaca tccgcttcgt cgcactgacc     1020
gccgtgggcg aggttacccg cattgagggg ccctcaaaac aagatttaca gagtgcttat     1080
gaggcaatca gccactaa                                                   1098

<210> SEQ ID NO 8
<211> LENGTH: 438
<212> TYPE: DNA
<213> ORGANISM: Corynebacterium glutamicum

<400> SEQUENCE: 8
atgcttggaa aaattctcct cctcaacggc ccaaacctga acatgctggg caaacgcgag       60
cctgacattt acggacacga caccttggaa gacgtcgtcg cgctggcaac cgctgaggct      120
gcgaagcacg gccttgaggt tgaggcgctg cagagcaatc acgaaggtga gctaatcgat      180
gcgctgcaca cgctcgcgg cacccacatc ggttgcgtga ttaaccccgg cggcctgact      240
cacacttcgg tggcgctttt ggatgcggtg aaggcgtctg agcttcctac cgttgaggtg      300
cacatttcca atccgcatgc ccgtgaagag ttccgccacc attcttacat ttccctcgcc      360
gcggtctccg ttatcgctgg cgctggcatc cagggttacc gtttcgcggt cgatatcctg      420
gcaaatctca aaaagtag                                                    438

<210> SEQ ID NO 9
<211> LENGTH: 831
<212> TYPE: DNA
<213> ORGANISM: Corynebacterium glutamicum

<400> SEQUENCE: 9
ttgggttctc acatcactca ccgggcggcc gtactcggct cacccatcga gcattccaaa       60
tccccagtcc tccacaacac cggctataaa gccctcggac tggaccaatg ggaatacgac      120
cgctttgagt gcaccggcga catgctcccc ggaatcgtct ccggcgctga tgaaacctac      180
cgcggattct ccgtcactat gccgtccaaa ttcgcagccc tcgaattcgc cgacgaagta      240
accgaacgcg cccgcgccat cggctccgca aacacacttc tgcgcaccga accggatgg       300 cgcgcagaca caccgacgt cgacggcatc aggggagccc tcggtgaact cctcggcagc      360
gcatcactgg ccggcaaaca cgccatcgtc atcggctccg gcggcaccgc acgcccccgcc    420 atctgggcac tcatcgaagc cggggtcgcg cggatcacgg tgctcaaccg ctccgatcga      480
accgccgaac tgcaaacgct tttcgacgaa accccaccaa ccttggccta cgccccgctc      540
gaacatctcg acatcgaagc cgacgtcgta gtctctacag tgcccctccgc agcaatcgca      600 ggcctcgaag acacactcgc aatcgcccca gtcctcgacg tcatctacga tccttggcca      660
acaccactcg tagaagtcgc acgagccaaa ggtctcaaag ctgtcggagg ccacgtcatg      720
ctggcacacc agtcctacgg acagtttgaa caattcaccg gaatggatgc accccgcgat      780
gctatgcgtg aggctttgga agaatcccta ggcatctcgg aagaacacta g              831

<210> SEQ ID NO 10
<211> LENGTH: 2094
```

<212> TYPE: DNA
<213> ORGANISM: Corynebacterium glutamicum

<400> SEQUENCE: 10

```
ttgacgctgt cacctgaact tcaggcgctc actgtacgca attaccctc tgattggtcc      60
gatgtggaca ccaaggctgt agacactgtt cgtgtcctcg ctgcagacgc tgtagaaaac    120
tgtggctccg gccacccagg caccgcaatg agcctggctc cccttgcata caccttgtac    180
cagcgggtta tgaacgtaga tccacaggac accaactggg caggccgtga ccgcttcgtt    240
ctttcttgtg gccactcctc tttgacccag tacatccagc tttacttggg tggattcggc    300
cttgagatgg atgacctgaa ggctctgcgc acctgggatt ccttgacccc aggacaccct    360
gagtaccgcc acaccaaggg cgttgagatc accactggcc ctcttggcca gggtcttgca    420
tctgcagttg gtatggccat ggctgctcgt cgtgagcgtg gcctattcga cccaaccgct    480
gctgagggcg aatccccatt cgaccaccac atctacgtca ttgcttctga tggtgacctg    540
caggaaggtg tcacctctga ggcatcctcc atcgctggca cccagcagct gggcaacatc    600
atcgtgttct gggatgacaa ccgcatctcc atcgaagaca cactgagat cgctttcaac    660
gaggacgttg ttgctcgtta caaggcttac ggctggcaga ccattgaggt tgaggctggc    720
gaggacgttg cagcaatcga agctgcagtg gctgaggcta agaaggacac caagcgacct    780
accttcatcc gcgttcgcac catcatcggc ttcccagctc caaccatgat gaacaccggt    840
gctgtgcacg gtgctgctct tggcgcagct gaggttgcag caaccaagac tgagcttgga    900
ttcgatcctg aggctcactt cgcgatcgac gacgaggtca tcgctcacac ccgctccctc    960
gcagagcgcg ctgcagagaa gaaggctgca tggcaggtca agttcgatga gtgggcagct   1020
gccaaccctg agaacaaggc tctgttcgat cgcctgaact cccgtgagct tccagcgggc   1080
tacgctgacg agctcccaac atgggatgca gatgagaagg gcgtcgcaac tcgtaaggcg   1140
tccgaggctg cacttcaggc actgggcaag acccttcctg agctgtgggg cggttccgct   1200
gacctcgcag gttccaacaa caccgtgatc aagggctccc cttccttcgg ccctgagtcc   1260
atctccaccg agacctggtc tgctgagcct tacggccgta acctgcactt cggtatccgt   1320
gagcacgcta tgggatccat cctcaacggc atttccctcc acggtggcac ccgcccatac   1380
ggcggaacct tcctcatctt ctccgactac atgcgtcctg cagttcgtct tgcagctctc   1440
atggagaccac acgcttacta cgtctggacc cacgactcca tcggtctggg cgaagatggc   1500
ccaacccacc agcctgttga aaccttggct gcactgcgcg ccatcccagg tctgtccgtc   1560
ctgcgtcctg cagatgcgaa tgagaccgcc caggcttggg ctgcagcact tgagtacaat   1620
gaaggcccta agggtcttgc actgacccgc cagaacgttc ctgttctgga aggcaccaag   1680
gagaaggctg ctgaaggcgt tcgccgcggt ggctacgtcc tggttgaggg ttccaaggaa   1740
accccagatg tgatcctcat gggctccggc tccgaggttc agcttgcagt taacgctgcg   1800
aaggctctgg aagctgaggg cgttgcagct cgcgttgttt ccgttccttg catggattgg   1860
ttccaggagc aggacgcaga gtacatcgag tccgttctgc ctgcagctgt gaccgctcgt   1920
gtgtctgttg aagctggcat cgcaatgcct tggtaccgct tcttgggcac ccagggccgt   1980
gctgtctccc ttgagcactt cggtgcttct gcggattacc agaccctgtt tgagaagttc   2040
ggcatcacca ccgatgcagt cgtggcagcg ccaaggact ccattaacgg ttaa          2094
```

<210> SEQ ID NO 11
<211> LENGTH: 1083
<212> TYPE: DNA

<213> ORGANISM: Corynebacterium glutamicum

<400> SEQUENCE: 11

```
atgtctcaca ttgatgatct ggcacagctc ggcacttcca cttggctcga cgacctctcc    60
cgcgagcgca ttacttccgg caatctcagc caggttattg aggaaaagtc tgtagtcggt   120
gtcaccacca acccagctat tttcgcagca gcaatgtcca agggcgattc ctacgacgct   180
cagatcgcag agctcaaggc cgctggcgca tctgttgacc aggctgttta cgccatgagc   240
atcgacgacg ttcgcaatgc ttgtgatctg tttaccggca tcttcgagtc ctccaacggc   300
tacgacggcc gcgtgtccat cgaggttgac ccacgtatct ctgcggaccg cgacgcaacc   360
ctggctcagg ccaaggagct gtgggcaaag gttgatcgtc aaacgtcat gatcaagatc   420
cctgctaccc caggttcttt gccagcaatc accgacgctt ggctgagggg catcagtgtt   480
aacgtcacct tgatcttctc cgttgctcgc taccgcgaag tcatcgctgc gttcatcgag   540
ggcatcaagc aggcagctgc aaacggccac gacgtatcca agatccactc tgtggcttcc   600
ttcttcgtct cccgcgtcga cgttgagatc gacaagcgcc tcgaggcaat cggatccgat   660
gaggctttgg ctctgcgtgg caaggcaggc gttgccaacg ctcagcgcgc ttacgctgtg   720
tacaaggagc ttttcgacgc cgccgagctg cctgaaggcg ccaacactca gcgcccactg   780
tgggcatcca ccggcgtgaa gaaccctgcg tacgctgcaa ctctttacgt ttccgagctg   840
gctggtccaa acaccgtcaa caccatgcca gaaggcacca tcgacgctgt tctgaactg   900
ggcaacctgc acggtgacac cctgtccaac tccgcggcag aagctgacgc tgtgttctcc   960
cagcttgagg ctctgggcgt tgacttggca gatgtcttcc aggtcctgga gaccgagggc  1020
gtggacaagt tcgttgcttc ttggagcgaa ctgcttgagt ccatggaagc tcgcctgaag  1080
tag                                                                1083
```

<210> SEQ ID NO 12
<211> LENGTH: 486
<212> TYPE: DNA
<213> ORGANISM: Corynebacterium glutamicum

<400> SEQUENCE: 12

```
tcgctcgtct cataaaaacg accgagccta ttgggattac cattgaagcc agtgtgagtt    60
gcatcacact ggcttcaaat ctgagacttt actttgtgga ttcacgggg tgtagtgcaa   120
ttcataatta gccccattcg ggggagcaga tcgcggcgcg aacgatttca ggttcgttcc   180
ctgcaaaaac tatttagcgc aagtgttgga aatgccccg tctggggtca atgtctattt    240
ttgaatgtgt ttgtatgatt ttgaatccgc tgcaaaatct ttgtttcccc gctaaagttg   300
gggacaggtt gacacggagt tgactcgacg aattatccaa tgtgagtagg tttggtgcgt   360
gagttggaaa atttcgccat actcgccctt gggttctgtc agctcaagaa ttcttgagtg   420
accgatgctc tgattgacct aactgcttga cacattgcat ttcctacaat ctttagagga   480
gacaca                                                              486
```

<210> SEQ ID NO 13
<211> LENGTH: 4586
<212> TYPE: DNA
<213> ORGANISM: Artificial sequence
<220> FEATURE:
<223> OTHER INFORMATION: plasmid pKK223-3

<400> SEQUENCE: 13

```
ttctgtttcc tgtgtgaaat tgttatccgc tcacaattcc acacattata cgagccgatg    60
```

```
attaattgtc aacagctcat ttcagaatat ttgccagaac cgttatgatg tcggcgcaaa    120
aaacattatc cagaacggga gtgcgccttg agcgacacga attatgcagt gatttacgac    180
ctgcacagcc ataccacagc ttccgatggc tgcctgacgc cagaagcatt ggtgcaccgt    240
gcagtcgata agctccggat cctctacgcc ggacgcatcg tggccggcat caccggcgcc    300
acaggtgcgg ttgctggcgc ctatatcgcc gacatcaccg atggggaaga tcgggctcgc    360
cacttcgggc tcatgagcgc ttgtttcggc gtgggtatgg tggcaggccc cgtgccgggg    420
ggactgttgg gcgccatctc cttgcatgca ccattccttg cggcggcggt gctcaacggc    480
ctcaacctac tactgggctg cttcctaatg caggagtcgc ataagggaga gcgtcgaccg    540
atgcccttga gagccttcaa cccagtcagc tccttccggt gggcgcgggg catgactatc    600
gtcgccgcac ttatgactgt cttctttatc atgcaactcg taggacaggt gccggcagcg    660
ctctgggtca ttttcggcga ggaccgcttt cgctggagcg cgacgatgat cggcctgtcg    720
cttgcggtat tcggaatctt gcacgccctc gctcaagcct tcgtcactgg tcccgccacc    780
aaacgtttcg gcgagaagca ggccattatc gccggcatgg cggccgacgc gctgggctac    840
gtcttgctgg cgttcgcgac gcgaggctgg atggccttcc ccattatgat tcttctcgct    900
tccggcggca tcgggatgcc cgcgttgcag gccatgctgt ccaggcaggt agatgacgac    960
catcagggac agcttcaagg atcgctcgcg gctcttacca gcctaacttc gatcactgga   1020
ccgctgatcg tcacggcgat ttatgccgcc tcggcgagca catggaacgg gttggcatgg   1080
attgtaggcg ccgccctata ccttgtctgc ctccccgcgt tgcgtcgcgg tgcatggagc   1140
cgggccacct cgacctgaat ggaagccggc ggcacctcgc taacggattc accactccaa   1200
gaattggagc caatcaattc ttgcggagaa ctgtgaatgc gcaaaccaac ccttggcaga   1260
acatatccat cgcgtccgcc atctccagca gccgcacgcg gcgcatctcg ggcagcgttg   1320
ggtcctggcc acgggtgcgc atgatcgtgc tcctgtcgtt gaggaccggg ctaggctggc   1380
ggggttgcct tactggttag cagaatgaat caccgatacg cgagcgaacg tgaagcgact   1440
gctgctgcaa aacgtctgcg acctgagcaa caacatgaat ggtcttcggt ttccgtgttt   1500
cgtaaagtct ggaaacgcgg aagtcagcgc cctgcaccat tatgttccgg atctgcatcg   1560
caggatgctg ctggctaccc tgtggaacac ctacatctgt attaacgaag cgctggcatt   1620
gaccctgagt gatttttctc tggtcccgcc gcatccatac cgccagttgt ttaccctcac   1680
aacgttccag taaccgggca tgttcatcat cagtaacccg tatcgtgagc atcctctctc   1740
gtttcatcgg tatcattacc cccatgaaca gaaattcccc cttacacgga ggcatcaagt   1800
gaccaaacag gaaaaaaccg cccttaacat ggcccgcttt atcagaagcc agacattaac   1860
gcttctggag aaactcaacg agctggacgc ggatgaacag gcagacatct gtgaatcgct   1920
tcacgaccac gctgatgagc tttaccgcag ctgcctcgcg cgtttcggtg atgacggtga   1980
aaacctctga cacatgcagc tcccggagac ggtcacagct tgtctgtaag cggatgccgg   2040
gagcagacaa gcccgtcagg gcgcgtcagc gggtgttggc gggtgtcggg gcgcagccat   2100
gacccagtca cgtagcgata gcggagtgta tactggctta actatgcggc atcagagcag   2160
attgtactga gagtgcacca tatgcggtgt gaaataccgc acagatgcgt aaggagaaaa   2220
taccgcatca ggcgctcttc cgcttcctcg ctcactgact cgctgcgctc ggtcgttcgg   2280
ctgcggcgag cggtatcagc tcactcaaag gcggtaatac ggttatccac agaatcaggg   2340
gataacgcag gaaagaacat gtgagcaaaa ggccagcaaa aggccaggaa ccgtaaaaag   2400
```

```
gccgcgttgc tggcgttttt ccataggctc cgccccctg acgagcatca caaaaatcga   2460
cgctcaagtc agaggtggcg aaacccgaca ggactataaa gataccaggc gtttccccct   2520
ggaagctccc tcgtgcgctc tcctgttccg accctgccgc ttaccggata cctgtccgcc   2580
tttctccctt cgggaagcgt ggcgctttct catagctcac gctgtaggta tctcagttcg   2640
gtgtaggtcg ttcgctccaa gctgggctgt gtgcacgaac cccccgttca gcccgaccgc   2700
tgcgccttat ccggtaacta tcgtcttgag tccaacccgg taagacacga cttatcgcca   2760
ctggcagcag ccactggtaa caggattagc agagcgaggt atgtaggcgg tgctacagag   2820
ttcttgaagt ggtggcctaa ctacggctac actagaagga cagtatttgg tatctgcgct   2880
ctgctgaagc cagttacctt cggaaaaaga gttggtagct cttgatccgg caaacaaacc   2940
accgctggta gcggtggttt ttttgtttgc aagcagcaga ttacgcgcag aaaaaaagga   3000
tctcaagaag atcctttgat cttttctacg gggtctgacg ctcagtggaa cgaaaactca   3060
cgttaaggga ttttggtcat gagattatca aaaaggatct tcacctagat ccttttaaat   3120
taaaaatgaa gttttaaatc aatctaaagt atatatgagt aaacttggtc tgacagttac   3180
caatgcttaa tcagtgaggc acctatctca gcgatctgtc tatttcgttc atccatagtt   3240
gcctgactcc ccgtcgtgta gataactacg atacgggagg gcttaccatc tggccccagt   3300
gctgcaatga taccgcgaga cccacgctca ccggctccag atttatcagc aataaaccag   3360
ccagccggaa gggccgagcg cagaagtggt cctgcaactt tatccgcctc catccagtct   3420
attaattgtt gccgggaagc tagagtaagt agttcgccag ttaatagttt gcgcaacgtt   3480
gttgccattg ctacaggcat cgtggtgtca cgctcgtcgt ttggtatggc ttcattcagc   3540
tccggttccc aacgatcaag gcgagttaca tgatccccca tgttgtgcaa aaaagcggtt   3600
agctccttcg gtcctccgat cgttgtcaga agtaagttgg ccgcagtgtt atcactcatg   3660
gttatggcag cactgcataa ttctcttact gtcatgccat ccgtaagatg cttttctgtg   3720
actggtgagt actcaaccaa gtcattctga gaatagtgta tgcggcgacc gagttgctct   3780
tgcccggcgt caacacggga taataccgcg ccacatagca gaactttaaa agtgctcatc   3840
attggaaaac gttcttcggg gcgaaaactc tcaaggatct taccgctgtt gagatccagt   3900
tcgatgtaac ccactcgtgc acccaactga tcttcagcat cttttacttt caccagcgtt   3960
tctgggtgag caaaaacagg aaggcaaaat gccgcaaaaa agggaataag ggcgacacgg   4020
aaatgttgaa tactcatact cttcctttt caatattatt gaagcattta tcagggttat   4080
tgtctcatga gcggatacat atttgaatgt atttagaaaa ataaacaaaa gagtttgtag   4140
aaacgcaaaa aggccatccg tcaggatggc cttctgctta atttgatgcc tggcagttta   4200
tggcgggcgt cctgcccgcc accctccggg ccgttgcttc gcaacgttca aatccgctcc   4260
cggcggattt gtcctactca ggagagcgtt caccgacaaa caacagataa aacgaaaggc   4320
ccagtctttc gactgagcct ttcgttttat ttgatgcctg gcagttccct actctcgcat   4380
ggggagaccc cacactacca tcggcgctac ggcgtttcac ttctgagttc ggcatggggt   4440
caggtgggac caccgcgcta ctgccgccag gcaaattctg ttttatcaga ccgcttctgc   4500
gttctgattt aatctgtatc aggctgaaaa tcttctctca tccgccaaaa cagaagcttg   4560
gctgcaggtc gacggatccc cgggaa                                       4586

<210> SEQ ID NO 14
<211> LENGTH: 32
<212> TYPE: DNA
<213> ORGANISM: Artificial sequence
```

```
<220> FEATURE:
<223> OTHER INFORMATION: PCR primer

<400> SEQUENCE: 14
ctctctgcag tcgctcgtct cataaaaacg ac                                    32

<210> SEQ ID NO 15
<211> LENGTH: 52
<212> TYPE: DNA
<213> ORGANISM: Artificial Sequence
<220> FEATURE:
<223> OTHER INFORMATION: PCR primer

<400> SEQUENCE: 15
ctctaagctt gtcgacggat ccgcatgctg tgtctcctct aaagattgta gg              52

<210> SEQ ID NO 16
<211> LENGTH: 30
<212> TYPE: DNA
<213> ORGANISM: Artificial sequence
<220> FEATURE:
<223> OTHER INFORMATION: PCR primer

<400> SEQUENCE: 16
ctctgcatgc ctgttttggc ggatgagaga                                       30

<210> SEQ ID NO 17
<211> LENGTH: 47
<212> TYPE: DNA
<213> ORGANISM: Artificial sequence
<220> FEATURE:
<223> OTHER INFORMATION: PCR primer

<400> SEQUENCE: 17
ctctaagctt gtcgacggat ccaagagttt gtagaaacgc aaaaagg                    47

<210> SEQ ID NO 18
<211> LENGTH: 1118
<212> TYPE: DNA
<213> ORGANISM: Escherichia coli

<400> SEQUENCE: 18
atgaattatc agaacgacga tttacgcatc aaagaaatca agagttact tcctcctgtc      60
gcattgctgg aaaaattccc cgctactgaa atgccgcga atacggttgc ccatgcccga     120
aaagcgatcc ataagatcct gaaaggtaat gatgatcgcc tgttggttgt gattggccca     180
tgctcaattc atgatcctgt cgcggcaaaa gagtatgcca ctcgcttgct ggcgctgcgt     240
gaagagctga agatgagct ggaaatcgta atgcgcgtct attttgaaaa gccgcgtacc     300
acggtgggct ggaaagggct gattaacgat ccgcatatgg ataatagctt ccagatcaac     360
gacggtctgc gtatagcccg taaattgctg cttgatatta cgacagcgg tctgccagcg     420
gcaggtgagt ttctcgatat gatcaccca caatatctcg ctgacctgat gagctggggc     480
gcaattggcg cacgtaccac cgaatcgcag gtgcaccgcg aactggcatc agggctttct     540
tgtccggtcg gcttcaaaaa tggcaccgac ggtacgatta agtggctat cgatgccatt     600
aatgccgccg gtgcgccgca ctgcttcctg tccgtaacga aatgggggca ttcggcgatt     660
gtgaatacca gcggtaacgg cgattgccat atcattctgc gcggcggtaa agagcctaac     720
tacagcgcga agcacgttgc tgaagtgaaa gaagggctga acaaagcagg cctgccagca     780
caggtgatga tcgatttcag ccatgctaac tcgtccaaac aattcaaaaa gcagatggat     840
```

```
gtttgtgctg acgtttgcca gcagattgcc ggtggcgaaa aggccattat tggcgtgatg    900
gtggaaagcc atctggtgga aggcaatcag agcctcgaga gcggggagcc gctggcctac    960
ggtaagagca tcaccgatgc ctgcatcggc tgggaagata ccgatgctct gttacgtcaa   1020
ctggcgaatg cagtaaaagc gcgtcgcggg taaggtttaa ttgtcggatg cgccgtcaga   1080
gtggcgtatc cgatgaatca ccacaggcct gataagtc                           1118
```

```
<210> SEQ ID NO 19
<211> LENGTH: 37
<212> TYPE: DNA
<213> ORGANISM: Artificial sequence
<220> FEATURE:
<223> OTHER INFORMATION: PCR primer

<400> SEQUENCE: 19
ctctgatatc atgaattatc agaacgacga tttacgc                              37

<210> SEQ ID NO 20
<211> LENGTH: 30
<212> TYPE: DNA
<213> ORGANISM: Artificial sequence
<220> FEATURE:
<223> OTHER INFORMATION: PCR primer

<400> SEQUENCE: 20
ctctgatatc gacttatcag gcctgtggtg                                      30

<210> SEQ ID NO 21
<211> LENGTH: 24
<212> TYPE: DNA
<213> ORGANISM: Artificial sequence
<220> FEATURE:
<223> OTHER INFORMATION: PCR primer

<400> SEQUENCE: 21
tttgtccggt cggcttcaaa aatg                                            24

<210> SEQ ID NO 22
<211> LENGTH: 19
<212> TYPE: DNA
<213> ORGANISM: Artificial sequence
<220> FEATURE:
<223> OTHER INFORMATION: PCR primer

<400> SEQUENCE: 22
aaagccctga tgccagttc                                                  19

<210> SEQ ID NO 23
<211> LENGTH: 23
<212> TYPE: DNA
<213> ORGANISM: Artificial sequence
<220> FEATURE:
<223> OTHER INFORMATION: PCR primer

<400> SEQUENCE: 23
tacaatatct cgctgacctg atg                                             23

<210> SEQ ID NO 24
<211> LENGTH: 22
<212> TYPE: DNA
<213> ORGANISM: Artificial sequence
<220> FEATURE:
<223> OTHER INFORMATION: PCR primer

<400> SEQUENCE: 24
```
gggtgatcat atcgagaaac tc                                           22

<210> SEQ ID NO 25
<211> LENGTH: 1140
<212> TYPE: DNA
<213> ORGANISM: Corynebacterium glutamicum

<400> SEQUENCE: 25
atgagcgcag cgcagatttt caacaccgtc cacgtcaatg gatcttcccc ctatgatgtc    60
cacattggtt ccggcctcaa cgagctcatt gttcagcgcg cagcggaatc aggcgcggag   120
caggtagcga ttttgcacca gcccagcatg gatgacattg catccgagtt ggatgcagca   180
ctagtcgctg ctggtttgaa ggtcctgcac cttaatgttc ccgatgcgga aaacggcaag   240
tccttggaag tagcggggca gtgctgggat gaattgggtg gcgcagcatt cggccgccgc   300
gatatcgtca tcggacttgg tggcggtgct gccacagatc tcgcgggatt cgtcgctgct   360
gcgtggatgc gtggcgtgcg cgtcattcag gttccaacca ccttgttggc catggtggac   420
gctgcggtgg gcggcaagac tggcatcaat accgccgcag gcaagaacct tgtgggcgcg   480
ttccacgagc ctgacgcagt attcattgac accgaacgcc tagccaccct gcctgacgcg   540
gaaatcatcg cgggatccgc cgaaatcatc aaaactggtt tcatcgccga cccagaaatc   600
ctgcgccttt acgaaactga tcccgcagcc tgcctgaaga agaagtcga aggctcccac   660
ctacctgaac tgatttggcg ctccgtcacc gtcaagggct ccgtggtcgg ccaagacctc   720
aaagaatcta gcctgcgcga atcctcaac tacggacaca cctttgccca cgccgtcgaa   780
ctccgcgaaa acttccgctg gcgccacggc aatgccgttg cagtgggcat gatgttcatc   840
gctaacctct cccacaagct cgggcttatc gacgcgcccc tcctcgagcg ccaccgctca   900
atcctggcgg ccatcggtct gcccacttcc tacgaaggcg gagccttcga cgagctttac   960
gacggcatga cccgcgacaa gaaaaaccgc gacggcaaca tccgcttcgt cgcactgacc  1020
gccgtgggcg aggttacccg cattgagggg ccctcaaaac aagatttaca gagtgcttat  1080
gaggcaatca gccactaagt gttgagtaat ctactagttt ggactagaag ttatccactt  1140

<210> SEQ ID NO 26
<211> LENGTH: 438
<212> TYPE: DNA
<213> ORGANISM: Corynebacterium glutamicum

<400> SEQUENCE: 26
atgcttggaa aaattctcct cctcaacggc ccaaacctga acatgctggg caaacgcgag    60
cctgacattt acggacacga caccttggaa gacgtcgtcg cgctggcaac cgctgaggct   120
gcgaagcacg gccttgaggt tgaggcgctg cagagcaatc acgaaggtga gctaatcgat   180
gcgctgcaca acgctcgcgg cacccacatc ggttgcgtga ttaaccccgg cggcctgact   240
cacacttcgg tggcgctttt ggatgcggtg aaggcgtctg agcttcctac cgttgaggtg   300
cacatttcca atccgcatgc ccgtgaagag ttccgccacc attcttacat ttccctcgcc   360
gcggtctccg ttatcgctgg cgctggcatc cagggttacc gtttcgcggt cgatatcctg   420
gcaaatctca aaaagtag                                                  438

<210> SEQ ID NO 27
<211> LENGTH: 851
<212> TYPE: DNA
<213> ORGANISM: Corynebacterium glutamicum

<400> SEQUENCE: 27

```
ataaggatca acgaataaaa ttgggttctc acatcactca ccgggcggcc gtactcggct       60
cacccatcga gcattccaaa tccccagtcc tccacaacac cggctataaa gccctcggac      120
tggaccaatg ggaatacgac cgctttgagt gcaccggcga catgctcccc ggaatcgtct      180
ccggcgctga tgaaacctac cgcggattct ccgtcactat gccgtccaaa ttcgcagccc      240
tcgaattcgc cgacgaagta accgaacgcg cccgcgccat cggctccgca aacacacttc      300
tgcgcaccga aaccggatgg cgcgcagaca acaccgacgt cgacggcatc aggggagccc      360
tcggtgaact cctcggcagc gcatcactgg ccggcaaaca cgccatcgtc atcggctccg      420
gcggcaccgc acgcccgcc atctgggcac tcatcgaagc cggggtcgcg cggatcacgg      480
tgctcaaccg ctccgatcga accgccgaac tgcaaacgct tttcgacgaa ccccccacca      540
ccttggccta cgccccgctc gaacatctcg acatcgaagc cgacgtcgta gtctctacag      600
tgccctccgc agcaatcgca ggcctcgaag acacactcgc aatcgcccca gtcctcgacg      660
tcatctacga tccttggcca acaccactcg tagaagtcgc acgagccaaa ggtctcaaag      720
ctgtcggagg ccacgtcatg ctggcacacc agtcctacgg acagtttgaa caattcaccg      780
gaatggatgc accccgcgat gctatgcgtg aggctttgga agaatcccta ggcatctcgg      840
aagaacacta g                                                          851
```

```
<210> SEQ ID NO 28
<211> LENGTH: 30
<212> TYPE: DNA
<213> ORGANISM: Artificial sequence
<220> FEATURE:
<223> OTHER INFORMATION: PCR primer

<400> SEQUENCE: 28
ctctgaattc atgagcgcag cgcagatttt                                       30

<210> SEQ ID NO 29
<211> LENGTH: 30
<212> TYPE: DNA
<213> ORGANISM: Artificial sequence
<220> FEATURE:
<223> OTHER INFORMATION: PCR primer

<400> SEQUENCE: 29
ctctcccggg aagtggataa cttctagtcc                                       30

<210> SEQ ID NO 30
<211> LENGTH: 32
<212> TYPE: DNA
<213> ORGANISM: Artificial Sequence
<220> FEATURE:
<223> OTHER INFORMATION: PCR primer

<400> SEQUENCE: 30
ctctgaattc atgcttggaa aaattctcct cc                                    32

<210> SEQ ID NO 31
<211> LENGTH: 30
<212> TYPE: DNA
<213> ORGANISM: Artificial sequence
<220> FEATURE:
<223> OTHER INFORMATION: PCR primer

<400> SEQUENCE: 31
ctctcccggg ctacttttg agatttgcca                                        30
```

<210> SEQ ID NO 32
<211> LENGTH: 30
<212> TYPE: DNA
<213> ORGANISM: Artificial sequence
<220> FEATURE:
<223> OTHER INFORMATION: PCR primer

<400> SEQUENCE: 32
ctctcccggg ataaggatca acgaataaaa                                      30

<210> SEQ ID NO 33
<211> LENGTH: 30
<212> TYPE: DNA
<213> ORGANISM: Artificial sequence
<220> FEATURE:
<223> OTHER INFORMATION: PCR primer

<400> SEQUENCE: 33
ctctctgcag ctagtgttct tccgagatgc                                      30

<210> SEQ ID NO 34
<211> LENGTH: 5426
<212> TYPE: DNA
<213> ORGANISM: Artificial Sequence
<220> FEATURE:
<223> OTHER INFORMATION: plasmid pSKM4

<400> SEQUENCE: 34

```
caagaattga ttggctccaa ttcttggagt ggtgaatccg ttagcgaggt gccgccggct      60
tccattcagg tcgaggtggc ccggctccat gcaccgcgac gcaacgcggg gaggcagaca     120
aggtataggg cggcgcctac aatccatgcc aacccgttcc atgtgctcgc cgaggcggca     180
taaatcgccg tgacgatcag cggtccagtg atcgaagtta ggctggtaag agccgcgagc     240
gatccttgaa gctgtccctg atggtcgtca tctacctgcc tggacagcat ggcctgcaac     300
gcgggcatcc cgatgccgcc ggaagcgaga agaatcataa tggggaaggc catccagcct     360
cgcgtcgcga acgccagcaa gacgtagccc agcgcgtcgg ccgccatgcc ggcgataatg     420
gcctgcttct cgccgaaacg tttggtggcg ggaccagtga cgaaggcttg agcgagggcg     480
tgcaagattc cgaataccgc aagcgacagg ccgatcatcg tcgcgctcca gcgaaagcgg     540
tcctcgccga aaatgaccca gagcgctgcc ggcacctgtc ctacgagttg catgataaag     600
aagacagtca taagtgcggc gacgatagtc atgccccgcg cccaccggaa ggagctgact     660
gggttgaagg ctctcaaggg catcggtcga cgctctccct tatgcgactc ctgcattagg     720
aagcagccca gtagtaggtt gaggccgttg agcaccgccg ccgcaaggaa tggtgcatgc     780
aaggagatgc cgcccaacag tcccccggcc acggggcctg ccaccatacc cacgccgaaa     840
caagcgctca tgagcccgaa gtggcgagcc cgatcttccc catcggtgat gtcggcgata     900
taggcgccag caaccgcacc tgtggcgccg gtgatgccgg ccacgatgcg tccggcgtag     960
aggatccgga gcttatcgac tgcacggtgc accaatgctt ctggcgtcag gcagccatcg    1020
gaagctgtgg tatggctgtg caggtcgtaa atcactgcat aattcgtgtc gctcaaggcg    1080
cactcccgtt ctgataatg ttttttgcgc cgacatcata acggtctgg caaatattct    1140 gaaatgagct gttgacaatt aatcatcggc tcgtataatg tgtggaattg tgagcggata    1200
acaatttcac acaggaaaca gaattcccgg gataaggatc aacgaataaa attgggttct    1260
cacatcactc accgggcggc cgtactcggc tcacccatcg agcattccaa atccccagtc    1320
```

| | | | | | |
|---|---|---|---|---|---|
| ctccacaaca | ccggctataa | agccctcgga | ctggaccaat | gggaatacga | ccgctttgag | 1380 |
| tgcaccggcg | acatgctccc | cggaatcgtc | tccggcgctg | atgaaaccta | ccgcggattc | 1440 |
| tccgtcacta | tgccgtccaa | attcgcagcc | ctcgaattcg | ccgacgaagt | aaccgaacgc | 1500 |
| gcccgcgcca | tcggctccgc | aaacacactt | ctgcgcaccg | aaaccggatg | gcgcgcagac | 1560 |
| aacaccgacg | tcgacggcat | caggggagcc | ctcggtgaac | tcctcggcag | cgcatcactg | 1620 |
| gccggcaaac | acgccatcgt | catcggctcc | ggcggcaccg | cacgccccgc | catctgggca | 1680 |
| ctcatcgaag | ccggggtcgc | gcggatcacg | gtgctcaacc | gctccgatcg | aaccgccgaa | 1740 |
| ctgcaaacgc | ttttcgacga | aacccccacc | accttggcct | acgccccgct | cgaacatctc | 1800 |
| gacatcgaag | ccgacgtcgt | agtctctaca | gtgccctccg | cagcaatcgc | aggcctcgaa | 1860 |
| gacacactcg | caatcgcccc | agtcctcgac | gtcatctacg | atccttggcc | aacaccactc | 1920 |
| gtagaagtcg | cacgagccaa | aggtctcaaa | gctgtcggag | gccacgtcat | gctggcacac | 1980 |
| cagtcctacg | gacagtttga | acaattcacc | ggaatggatg | caccccgcga | tgctatgcgt | 2040 |
| gaggctttgg | aagaatccct | aggcatctcg | gaagaacact | agctgcagcc | aagcttctgt | 2100 |
| tttggcggat | gagagaagat | tttcagcctg | atacagatta | aatcagaacg | cagaagcggt | 2160 |
| ctgataaaac | agaatttgcc | tggcggcagt | agcgcggtgg | tcccacctga | ccccatgccg | 2220 |
| aactcagaag | tgaaacgccg | tagcgccgat | ggtagtgtgg | ggtctcccca | tgcgagagta | 2280 |
| gggaactgcc | aggcatcaaa | taaaacgaaa | ggctcagtcg | aaagactggg | cctttcgttt | 2340 |
| tatctgttgt | ttgtcggtga | acgctctcct | gagtaggaca | aatccgccgg | gagcggattt | 2400 |
| gaacgttgcg | aagcaacggc | ccggagggtg | gcgggcagga | cgcccgccat | aaactgccag | 2460 |
| gcatcaaatt | aagcagaagg | ccatcctgac | ggatggcctt | tttgcgtttc | tacaaactct | 2520 |
| tttgtttatt | tttctaaata | cattcaaata | tgtatccgct | catgagacaa | taaccctgat | 2580 |
| aaatgcttca | ataatattga | aaaggaagag | tatgagtat | tcaacatttc | cgtgtcgccc | 2640 |
| ttattccctt | ttttgcggca | ttttgccttc | ctgttttgc | tcacccagaa | acgctggtga | 2700 |
| aagtaaaaga | tgctgaagat | cagttgggtg | cacgagtggg | ttacatcgaa | ctggatctca | 2760 |
| acagcggtaa | gatccttgag | agttttcgcc | ccgaagaacg | ttttccaatg | atgagcactt | 2820 |
| ttaaagttct | gctatgtggc | gcggtattat | cccgtgttga | cgccgggcaa | gagcaactcg | 2880 |
| gtcgccgcat | acactattct | cagaatgact | tggttgagta | ctcaccagtc | acagaaaagc | 2940 |
| atcttacgga | tggcatgaca | gtaagagaat | tatgcagtgc | tgccataacc | atgagtgata | 3000 |
| acactgcggc | caacttactt | ctgacaacga | tcggaggacc | gaaggagcta | accgcttttt | 3060 |
| tgcacaacat | gggggatcat | gtaactcgcc | ttgatcgttg | ggaaccggag | ctgaatgaag | 3120 |
| ccataccaaa | cgacgagcgt | gacaccacga | tgcctgtagc | aatggcaaca | acgttgcgca | 3180 |
| aactattaac | tggcgaacta | cttactctag | cttcccggca | acaattaata | gactggatgg | 3240 |
| aggcggataa | agttgcagga | ccacttctgc | gctcggccct | tccggctggc | tggtttattg | 3300 |
| ctgataaatc | tggagccggt | gagcgtgggt | ctcgcggtat | cattgcagca | ctggggccag | 3360 |
| atggtaagcc | ctcccgtatc | gtagttatct | acacgacggg | gagtcaggca | actatggatg | 3420 |
| aacgaaatag | acagatcgct | gagataggtg | cctcactgat | taagcattgg | taactgtcag | 3480 |
| accaagttta | ctcatatata | ctttagattg | atttaaaact | tcattttaa | tttaaaagga | 3540 |
| tctaggtgaa | gatcctttt | gataatctca | tgaccaaaat | cccttaacgt | gagttttcgt | 3600 |
| tccactgagc | gtcagacccc | gtagaaaaga | tcaaaggatc | ttcttgagat | ccttttttc | 3660 |
| tgcgcgtaat | ctgctgcttg | caaacaaaaa | aaccaccgct | accagcggtg | gtttgtttgc | 3720 |

```
cggatcaaga gctaccaact cttttttccga aggtaactgg cttcagcaga gcgcagatac    3780
caaatactgt ccttctagtg tagccgtagt taggccacca cttcaagaac tctgtagcac    3840
cgcctacata cctcgctctg ctaatcctgt taccagtggc tgctgccagt ggcgataagt    3900
cgtgtcttac cgggttggac tcaagacgat agttaccgga taaggcgcag cggtcgggct    3960 gaacggggggg ttcgtgcaca cagcccagct tggagcgaac gacctacacc gaactgagat    4020
acctacagcg tgagctatga gaaagcgcca cgcttcccga agggagaaag gcggacaggt    4080
atccggtaag cggcagggtc ggaacaggag agcgcacgag ggagcttcca gggggaaacg    4140
cctggtatct ttatagtcct gtcgggtttc gccacctctg acttgagcgt cgatttttgt    4200
gatgctcgtc agggggcgg agcctatgga aaaacgccag caacgcggcc ttttacggt      4260 tcctggcctt ttgctggcct tttgctcaca tgttctttcc tgcgttatcc cctgattctg    4320
tggataaccg tattaccgcc tttgagtgag ctgataccgc tcgccgcagc cgaacgaccg    4380
agcgcagcga gtcagtgagc gaggaagcgg aagagcgcct gatgcggtat tttctccttta  4440 cgcatctgtg cggtatttca caccgcatat ggtgcactct cagtacaatc tgctctgatg    4500
ccgcatagtt aagccagtat acactccgct atcgctacgt gactgggtca tggctgcgcc    4560
ccgacacccg ccaacacccg ctgacgcgcc ctgacgggct tgtctgctcc cggcatccgc    4620
ttacagacaa gctgtgaccg tctccgggag ctgcatgtgt cagaggtttt caccgtcatc    4680
accgaaacgc gcgaggcagc tgcggtaaag ctcatcagcg tggtcgtgaa gcgattcaca    4740
gatgtctgcc tgttcatccg cgtccagctc gttgagtttc tccagaagcg ttaatgtctg    4800
gcttctgata aagcgggcca tgttaagggc ggttttttcc tgtttggtca cttgatgcct    4860
ccgtgtaagg gggaatttct gttcatgggg gtaatgatac cgatgaaacg agagaggatg    4920
ctcacgatac gggttactga tgatgaacat gcccggttac tggaacgttg tgagggtaaa    4980
caactggcgg tatggatgcg gcgggaccag agaaaaatca ctcagggtca atgccagcgc    5040
ttcgttaata cagatgtagg tgttccacag ggtagccagc agcatcctgc gatgcagatc    5100
cggaacataa tggtgcaggg cgctgacttc cgcgtttcca gactttacga aacacggaaa    5160
ccgaagacca ttcatgttgt tgctcaggtc gcagacgttt tgcagcagca gtcgcttcac    5220
gttcgctcgc gtatcggtga ttcattctgc taaccagtaa ggcaacccccg ccagcctagc    5280 cgggtcctca acgacaggag cacgatcatg cgcacccgtg gccaggaccc aacgctgccc    5340
gagatgcgcc gcgtgcggct gctggagatg gcggacgcga tggatatgtt ctgccaaggg    5400
ttggtttgcg cattcacagt tctccg                                         5426
```

<210> SEQ ID NO 35
<211> LENGTH: 30
<212> TYPE: DNA
<213> ORGANISM: Artificial sequence
<220> FEATURE:
<223> OTHER INFORMATION: PCR primer

<400> SEQUENCE: 35
ctctggtacc ggctgtgcag gtcgtaaatc                                     30

<210> SEQ ID NO 36
<211> LENGTH: 30
<212> TYPE: DNA
<213> ORGANISM: Artificial sequence
<220> FEATURE:
<223> OTHER INFORMATION: PCR primer

<400> SEQUENCE: 36

```
ctctggtacc ctagtgttct tccgagatgc                                      30
```

<210> SEQ ID NO 37
<211> LENGTH: 7501
<212> TYPE: DNA
<213> ORGANISM: Artificial sequence
<220> FEATURE:
<223> OTHER INFORMATION: plasmid pSKM7

<400> SEQUENCE: 37

```
agatctaggt ttcccgactg gaaagcgggc agtgagcgca acgcaattaa tgtgagttag      60
ctcactcatt aggcacccca ggctttacac tttatgcttc cggctcgtat gttgtgtgga     120
attgtgagcg gataacaatt tcacacagga aacagctatg accatgatta cgaattcgag     180
ctcggtaccg gctgtgcagg tcgtaaatca ctgcataatt cgtgtcgctc aaggcgcact     240
cccgttctgg ataatgtttt ttgcgccgac atcataacgg ttctggcaaa tattctgaaa     300
tgagctgttg acaattaatc atcggctcgt ataatgtgtg gaattgtgag cggataacaa     360
tttcacacag gaaacagaat tcccgggata aggatcaacg aataaaattg ggttctcaca     420
tcactcaccg ggcggccgta ctcggctcac ccatcgagca ttccaaatcc ccagtcctcc     480
acaacaccgg ctataaagcc ctcggactgg accaatggga atacgaccgc tttgagtgca     540
ccggcgacat gctccccgga atcgtctccg gcgctgatga aacctaccgc ggattctccg     600
tcactatgcc gtccaaattc gcagccctcg aattcgccga cgaagtaacc gaacgcgccc     660
gcgccatcgg ctccgcaaac acacttctgc gcaccgaaac cggatggcgc gcagacaaca     720
ccgacgtcga cggcatcagg ggagccctcg gtgaactcct cggcagcgca tcactggccg     780
gcaaacacgc catcgtcatc ggctccggcg caccgcacg ccccgccatc tgggcactca     840
tcgaagccgg ggtcgcgcgg atcacggtgc tcaaccgctc cgatcgaacc gccgaactgc     900
aaacgctttt cgacgaaacc cccaccacct tggcctacgc cccgctcgaa catctcgaca     960
tcgaagccga cgtcgtagtc tctacagtgc cctccgcagc aatcgcaggc ctcgaagaca    1020
cactcgcaat cgccccagtc ctcgacgtca tctacgatcc ttggccaaca ccactcgtag    1080
aagtcgcacg agccaaaggt ctcaaagctg tcggaggcca cgtcatgctg cacaccagt     1140
cctacggaca gtttgaacaa ttcaccggaa tggatgcacc ccgcgatgct atgcgtgagg    1200
ctttggaaga atccctaggc atctcggaag aacactaggg tacccggggg ctgtgcaggt    1260
cgtaaatcac tgcataattc gtgtcgctca aggcgcactc ccgttctgga taatgttttt    1320
tgcgccgaca tcataacggt tctggcaaat attctgaaat gagctgttga caattaatca    1380
tcggctcgta taatgtgtgg aattgtgagc ggataacaat ttcacacagg aaacagaatt    1440
catgcttgga aaaattctcc tcctcaacgg cccaaacctg aacatgctgg caaacgcga     1500
gcctgacatt tacggacacg acaccttgga agacgtcgtc gcgctggcaa ccgctgaggc    1560
tgcgaagcac ggccttgagg ttgaggcgct gcagagcaat cacgaaggtg agctaatcga    1620
tgcgctgcac aacgctcgcg gcacccacat cggttgcgtg attaaccccg gcggcctgac    1680
tcacacttcg gtggcgcttt tggatgcggt gaaggcgtct gagcttccta ccgttgaggt    1740
gcacatttcc aatccgcatg cccgtgaaga gttccgccac cattcttaca tttccctcgc    1800
cgcggtctcc gttatcgctg gcgctggcat ccagggttac cgtttcgcgg tcgatatcct    1860
ggcaaatctc aaaagtagc ccgggatcc tctagagtcg acgctctccc ttatgcgact    1920
cctgcattag gaagcagccc agtagtaggt tgaggccgtt gagcaccgcc gccgcaagga    1980
```

```
atggtgcatg caaggagatg gcgcccaaca gtccccggc cacggggcct gccaccatac    2040
ccacgccgaa acaagcgctc atgagcccga agtggcgagc ccgatcttcc ccatcggtga    2100
tgtcggcgat ataggcgcca gcaaccgcac ctgtggcgcc ggtgatgccg gccacgatgc    2160
gtccggcgta gaggatccgg gcttatcgac tgcacggtgc accaatgctt ctggcgtcag    2220
gcagccatcg gaagctgtgg tatggctgtg caggtcgtaa atcactgcat aattcgtgtc    2280
gctcaaggcg cactcccgtt ctggataatg ttttttgcgc cgacatcata acggttctgg    2340
caaatattct gaaatgagct gttgacaatt aatcatcggc tcgtataatg tgtggaattg    2400
tgagcggata caatttcac acaggaaaca gaattcatga gcgcagcgca gattttcaac    2460
accgtccacg tcaatggatc ttcccctat gatgtccaca ttggttccgg cctcaacgag    2520
ctcattgttc agcgcgcagc ggaatcaggc gcggagcagg tagcgatttt gcaccagccc    2580
agcatggatg acattgcatc cgagttggat gcagcactag tcgctgctgg tttgaaggtc    2640 ctgcaccttta atgttcccga tgcggaaaac ggcaagtcct tggaagtagc ggggcagtgc    2700
tgggatgaat tgggtggcgc agcattcggc cgccgcgata tcgtcatcgg acttggtggc    2760
ggtgctgcca cagatctcgc gggattcgtc gctgctgcgt ggatgcgtgg cgtgcgcgtc    2820
attcaggttc caaccacctt gttggccatg gtggacgctg cggtgggcgg caagactggc    2880
atcaataccg ccgcaggcaa gaaccttgtg ggcgcgttcc acgagcctga cgcagtattc    2940
attgacaccg aacgcctagc caccctgcct gacgcggaaa tcatcgcggg atccgccgaa    3000
atcatcaaaa ctggtttcat cgccgaccca gaaatcctgc gcctttacga aactgatccc    3060
gcagcctgcc tgaagaaaga agtcgaaggc tcccacctac ctgaactgat tggcgctcc    3120 gtcaccgtca agggctccgt ggtcggccaa gacctcaaag aatctagcct gcgcgaaatc    3180
ctcaactacg gacacacctt tgcccacgcc gtcgaactcc gcgaaaactt ccgctggcgc    3240
cacggcaatg ccgttgcagt gggcatgatg ttcatcgcta acctctccca caagctcggg    3300
cttatcgacg cgcccctcct cgagcgccac cgctcaatcc tggcggccat cggtctgccc    3360
acttcctacg aaggcggagc cttcgacgag ctttacgacg gcatgacccg cgacaagaaa    3420
aaccgcgacg gcaacatccg cttcgtcgca ctgaccgccg tgggcgaggt tacccgcatt    3480
gaggggccct caaaacaaga tttacagagt gcttatgagg caatcagcca ctaagtgttg    3540
agtaatctac tagtttggac tagaagttat ccacttcccg gggatccgtc gacctgcagg    3600
catgcaagct tggcactggc cgtcgtttta caacgtcgtg actgggaaaa ccctggcgtt    3660
acccaactta atcgccttgc agcacatccc cctttcgcca gctggcgtaa tagcgaagag    3720
gcccgcaccg atcgcccttc ccaacagttg cgcagcctga atggcgaatg cgatttattc    3780
aacaaagccg ccgtcccgtc aagtcagcgt aatgctctgc cagtgttaca accaattaac    3840
caattctgat tagaaaaact catcgagcat caaatgaaac tgcaatttat tcatatcagg    3900
attatcaata ccatatttt gaaaaagccg tttctgtaat gaaggagaaa actcaccgag    3960
gcagttccat aggatggcaa gatcctggta tcggtctgcg attccgactc gtccaacatc    4020
aatacaacct attaatttcc cctcgtcaaa aataaggtta tcaagtgaga atcaccatg    4080 agtgacgact gaatccggtg agaatggcaa aagcttatgc atttctttcc agacttgttc    4140
aacaggccag ccattacgct cgtcatcaaa atcactcgca tcaaccaaac cgttattcat    4200
tcgtgattgc gcctgagcga gacgaaatac gcgatcgctg ttaaaaggac aattacaaac    4260
aggaatcgaa tgcaaccggc gcaggaacac tgccagcgca tcaacaatat ttcacctga    4320
```

```
atcaggatat tcttctaata cctggaatgc tgttttcccg gggatcgcag tggtgagtaa    4380
ccatgcatca tcaggagtac ggataaaatg cttgatggtc ggaagaggca taaattccgt    4440
cagccagttt agtctgacca tctcatctgt aacatcattg gcaacgctac ctttgccatg    4500
tttcagaaac aactctggcg catcgggctt cccatacaat cgatagattg tcgcacctga    4560
ttgcccgaca ttatcgcgag cccatttata cccatataaa tcagcatcca tgttggaatt    4620
taatcgcggc ttcgagcaag acgtttcccg ttgaatatgg ctcataacac cccttgtatt    4680
actgtttatg taagcagaca gttttattgt tcatgatgat atattttat cttgtgcaat     4740
gtaacatcag agattttgag acacaacgtg gctttgttga ataaatcgaa cttttgctga    4800
gttgaaggat cagatcacgc atcttcccga caacgcagac cgttccgtgg caaagcaaaa    4860
gttcaaaatc accaactggt ccacctacaa caaagctctc atcaaccgtg gctccctcac    4920
tttctggctg gatgatgggg cgattcaggc ctggtatgag tcagcaacac cttcttcacg    4980
aggcagacct ctcgacggag ttccactgag cgtcagaccc cgtagaaaag atcaaaggat    5040
cttcttgaga tcctttttt ctgcgcgtaa tctgctgctt gcaaacaaaa aaaccaccgc      5100
taccagcggt ggtttgtttg ccggatcaag agctaccaac tcttttttccg aaggtaactg    5160
gcttcagcag agcgcagata ccaaatactg ttcttctagt gtagccgtag ttaggccacc    5220
acttcaagaa ctctgtagca ccgcctacat acctcgctct gctaatcctg ttaccagtgg    5280
ctgctgccag tggcgataag tcgtgtctta ccgggttgga ctcaagacga tagttaccgg    5340
ataaggcgca gcggtcgggc tgaacggggg gttcgtgcac acagcccagc ttggagcgaa    5400
cgacctacac cgaactgaga tacctacagc gtgagctatg agaaagcgcc acgcttcccg    5460
aagggagaaa ggcggacagg tatccggtaa gcggcagggt cggaacagga gagcgcacga    5520
gggagcttcc agggggaaac gcctggtatc tttatagtcc tgtcgggttt cgccacctct    5580
gacttgagcg tcgatttttg tgatgctcgt cagggggggcg agcctatgg aaaaacgcca    5640
gcaacgcggc ctttttacgg ttcctggcct tttgctggcc ttttgctcac atgttctttc    5700
ctgcgttatc ccctgattct gtggataacc gtattaccgc ctttgagtga gctgataccg    5760
ctcgccgcag ccgaacgacc gagcgcagcg agtcagtgag cgaggaagcg gaagaagctc    5820
gcacattcag cagcgttttt cagcgcgttt tcgatcaacg tttcaatgtt ggtatcaaca    5880
ccaggtttaa ctttgaactt atcggcactg acgttactg attttgaact tttgctttgc     5940
cacggaacgg tctgcgttgt cgggaagatg cgtgatctga tccttcaact cagcaaaagt    6000
tcgccaatac gcaaaccgcc tctccccgcg cgttggccga ttcattaatg cagctggcac    6060
gagatctgac ttggttacga tggactttga acacgccgag ggtgactaaa ccgctggatt    6120
tacgcggttt tcttctcttc aacttctttg acgtagcggt gaaccgtgcc caccgagcaa    6180
ccaatctctg ccgcgatagc gcgcatggac agaccttttgg cgcgcagctc ctggacgcga   6240
gcacgcttct cgttggcacg tttaatgaac acttcacgcg gttcggaagt ccatcgttga    6300
gctgttctca ccgacatacc ggcacgttct gccagctcgc gggctgtttt tccgttgcgt    6360
ggataacgtg cataaacctt agccaatgtt cctccaaaga gtatgtccag cctcacgacg    6420
cacctcagcg cttcgttgcc agcctttctt cccgcgtgcg gattgcattg cggtgaatgt    6480
ggcgtcgtag acggcggcgc cgtctgtcca catgcgtgac ttggtgatga tccatttatg    6540
gattgacctg gcaatacagt caacttcggc cacaggtagt ggttcatcaa acagctcttg    6600
gttaagtgct tgcgcggtgg tttggattgc gcggcctagg ccgtcagcgt ctccaaaatg    6660
cttttctgacc tcccgatatg cccacgtacg tgcgctttca aagagtgcgc aattacgacc    6720
```

```
tagaccaact ggcgagaacc gccgcgtttt cctccaggac gcaggcggca taaagccggt   6780
ttcttcgagc caaaagcgca gctcatcgag cgtatacagc ttatcggtga tccagtgact   6840
atcccatgca gtgtgctcgg ggttttggt gatcagcccg gagtatccgc tatcgccatc    6900
gacagagcgc cgtaggcctt cggtgacagc cgcggcatag gccaaaggct tgcgtttggc   6960
gtattcggtg cgggtaaatg gctccgcgag cgcccagaca gcgtgtgcgt gcccgtttaa   7020
ggggttttca accaccgcgt taggtctcca gtcctccctg tcccacaaag agcgcaaaag   7080
cgcgtcctcc tggtcgatgt caacgaccag gaggttagag agcgcgtcgg gattggcttc   7140
gacgtagcgc ttatccagcg cgttcttccg tgaggtgcgg taaatgccct cacggaggtc   7200
atcgcttgcc aatggccaca gcggcagcca cagctgctca aagcgtccct cagggcgggt   7260
agttggtctc atgtagctga ctttctcaca cgagcgtgca cggtcggttt tcattcataa   7320
tacgacattt aaccaagtca gatgtttccc cggtttccgg gggttcccct gaagaaccct   7380
tccagtgcga gcgaagcgag ctcctttggc cggcgcccct caggtagccc tctaaggctc   7440
ccagggctcc gcccctccct gaggttggct caagcctcct ggtggctcct acggacgttc   7500
t                                                                   7501
```

```
<210> SEQ ID NO 38
<211> LENGTH: 17
<212> TYPE: DNA
<213> ORGANISM: Artificial sequence
<220> FEATURE:
<223> OTHER INFORMATION: PCR primer

<400> SEQUENCE: 38
caggaaacag ctatgac                                                    17

<210> SEQ ID NO 39
<211> LENGTH: 17
<212> TYPE: DNA
<213> ORGANISM: Artificial sequence
<220> FEATURE:
<223> OTHER INFORMATION: PCR primer

<400> SEQUENCE: 39
gttttcccag tcacgac                                                    17

<210> SEQ ID NO 40
<211> LENGTH: 3341
<212> TYPE: DNA
<213> ORGANISM: Corynebacterium glutamicum

<400> SEQUENCE: 40
ttgacgctgt cacctgaact tcaggcgctc actgtacgca attaccctc tgattggtcc      60 gatgtggaca ccaaggctgt agacactgtt cgtgtcctcg ctgcagacgc tgtagaaaac    120
tgtggctccg gccacccagg caccgcaatg agcctggctc cccttgcata caccttgtac    180
cagcgggtta tgaacgtaga tccacaggac accaactggg caggccgtga ccgcttcgtt    240 cttttcttgtg gccactcctc tttgacccag tacatccagc tttacttggg tggattcggc    300
cttgagatgg atgacctgaa ggctctgcgc acctgggatt ccttgacccc aggacaccct   360
gagtaccgcc acaccaaggg cgttgagatc accactggcc ctcttggcca gggtcttgca    420
tctgcagttg gtatggccat ggctgctcgt cgtgagcgtg gcctattcga cccaaccgct    480
gctgagggcg aatccccatt cgaccaccac atctacgtca ttgcttctga tggtgacctg    540
```

```
caggaaggtg tcacctctga ggcatcctcc atcgctggca cccagcagct gggcaacatc      600
atcgtgttct gggatgacaa ccgcatctcc atcgaagaca acactgagat cgctttcaac      660
gaggacgttg ttgctcgtta caaggcttac ggctggcaga ccattgaggt tgaggctggc      720
gaggacgttg cagcaatcga agctgcagtg gctgaggcta agaaggacac caagcgacct      780
accttcatcc gcgttcgcac catcatcggc ttcccagctc aaccatgat gaacaccggt       840 gctgtgcacg gtgctgctct tggcgcagct gaggttgcag caaccaagac tgagcttgga      900
ttcgatcctg aggctcactt cgcgatcgac gacgaggtca tcgctcacac ccgctccctc      960
gcagagcgcg ctgcagagaa gaaggctgca tggcaggtca agttcgatga gtgggcagct     1020
gccaaccctg agaacaaggc tctgttcgat cgcctgaact cccgtgagct tccagcgggc     1080
tacgctgacg agctcccaac atgggatgca gatgagaagg cgtcgcaac tcgtaaggcg      1140 tccgaggctg cacttcaggc actgggcaag acccttcctg agctgtgggg cggttccgct     1200
gacctcgcag gttccaacaa caccgtgatc aagggctccc cttccttcgg ccctgagtcc     1260
atctccaccg agacctggtc tgctgagcct tacgccgta acctgcactt cggtatccgt      1320
gagcacgcta tgggatccat cctcaacggc atttccctcc acggtggcac ccgcccatac     1380
ggcggaacct tcctcatctt ctccgactac atgcgtcctg cagttcgtct tgcagctctc     1440
atggagaccg acgcttacta cgtctggacc cacgactcca tcggtctggg cgaagatggc     1500
ccaacccacc agcctgttga aaccttggct gcactgcgcg ccatcccagg tctgtccgtc     1560
ctgcgtcctg cagatgcgaa tgagaccgcc caggcttggg ctgcagcact tgagtacaat     1620
gaaggcccta agggtcttgc actgacccgc cagaacgttc ctgttctgga aggcaccaag     1680
gagaaggctg ctgaaggcgt tcgccgcggt ggctacgtcc tggttgaggg ttccaaggaa     1740
accccagatg tgatcctcat gggctccggc tccgaggttc agcttgcagt taacgctgcg     1800
aaggctctgg aagctgaggg cgttgcagct cgcgttgttt ccgttccttg catggattgg     1860
ttccaggagc aggacgcaga gtacatcgag tccgttctgc ctgcagctgt gaccgctcgt     1920
gtgtctgttg aagctggcat cgcaatgcct tggtaccgct tcttgggcac ccagggccgt     1980
gctgtctccc ttgagcactt cggtgcttct gcggattacc agaccctgtt tgagaagttc     2040
ggcatcacca ccgatgcagt cgtggcagcg gccaaggact ccattaacgg ttaattgccc     2100
tgctgttttt agcttcaacc cggggcaata tgatcctccg gaattttatt gccccgggtt     2160
gttgttaatc ggtataaagg gtcttaagca catcccttac ttgcctgctc tccttgagcg     2220
cagttcaaga acaattcttt taaggaaaat ttagtttcat gtctcacatt gatgatctgg     2280
cacagctcgg cacttccact tggctcgacg acctctcccg cgagcgcatt acttccggca     2340
atctcagcca ggttattgag gaaaagtctg tagtcggtgt caccaccaac ccagctatt    2400 tcgcagcagc aatgtccaag ggcgattcct acgacgctca gatcgcagag ctcaaggccg     2460
ctggcgcatc tgttgaccag gctgtttacg ccatgagcat cgacgacgtt cgcaatgctt     2520
gtgatctgtt taccggcatc ttcgagtcct ccaacggcta cgacggccgc gtgtccatcg     2580
aggttgaccc acgtatctct gcggaccgcg acgcaaccct ggctcaggcc aaggagctgt     2640
gggcaaaggt tgatcgtcca aacgtcatga tcaagatccc tgctacccca ggttctttgc     2700
cagcaatcac cgacgctttg gctgagggca tcagtgttaa cgtcaccttg atcttctccg     2760
ttgctcgcta ccgcgaagtc atcgctgcgt tcatcgaggg catcaagcag gcagctgcaa     2820
acggccacga cgtatccaag atccactctg tggcttcctt cttcgtctcc cgcgtcgacg     2880
ttgagatcga caagcgcctc gaggcaatcg gatccgatga ggctttggct ctgcgtggca     2940
```

```
aggcaggcgt tgccaacgct cagcgcgctt acgctgtgta caaggagctt ttcgacgccg    3000
ccgagctgcc tgaaggcgcc aacactcagc gcccactgtg ggcatccacc ggcgtgaaga    3060
accctgcgta cgctgcaact ctttacgttt ccgagctggc tggtccaaac accgtcaaca    3120
ccatgccaga aggcaccatc gacgctgttc tggaactggg caacctgcac ggtgacaccc    3180
tgtccaactc cgcggcagaa gctgacgctg tgttctccca gcttgaggct ctgggcgttg    3240
acttggcaga tgtcttccag gtcctggaga ccgaggcgt ggacaagttc gttgcttctt     3300
ggagcgaact gcttgagtcc atggaagctc gcctgaagta g                        3341
```

<210> SEQ ID NO 41
<211> LENGTH: 26
<212> TYPE: DNA
<213> ORGANISM: Artificial sequence
<220> FEATURE:
<223> OTHER INFORMATION: PCR primer

<400> SEQUENCE: 41

```
ctctcatatg acgctgtcac ctgaac                                           26
```

<210> SEQ ID NO 42
<211> LENGTH: 28
<212> TYPE: DNA
<213> ORGANISM: Artificial sequence
<220> FEATURE:
<223> OTHER INFORMATION: PCR primer

<400> SEQUENCE: 42

```
ctctcatatg ctacttcagg cgagcttc                                         28
```

<210> SEQ ID NO 43
<211> LENGTH: 3000
<212> TYPE: DNA
<213> ORGANISM: Corynebacterium glutamicum

<400> SEQUENCE: 43

```
taatggtgtc gaccgacatc cgaatatcac catgggcaga tacaaagatc actacaacat      60
gtggagaaag ctcatttagt ttttcctgga gacgaatccc gctcatagat ggcatacgaa     120
catcaaggat caaacaagct ggcttagtgt catcaaacga gtccaagagt cctgagcgc      180
tatgacaaat tgtgctttcg atgctcgcgc tttctaatag ccaagcaacc gattcgcaca    240
cttccacgtc atcatccaca atgtagacga cgggatcaat cttatccatg ggttgaaaat    300
cttttccccac ctgctgtttc atcgcgatat tcacttaaat ctcaatccca agaagcttcg   360
gcgacccagt agttcatgcc aaaatcactg actcgatgtt cccagggcgt ggttcgacga    420
agttctggtt cctctaaacg aacggattca tctgcaaatt caggtccatc ggcttcaaca    480
gtccagtgga cccagttcac ttctcgaccg tgctcatcgt gaacaaacaa atcaacatga    540
tgccagccgt aattgaaagt gtcctcgtag caagttaaga acatatggtg gtggttgatg    600
ggacgtggtg gaattggttt ttctacagtt accatttcat ttccttaagt gttgatggtg    660
tctgggtgtt tgaaaatgac gggagctcgc gcagcagcgg ttccagtact tttcctagac    720
gcaacaaggt caattcatta tgtttgttgc cgataagttg tattcccaat ggcattccag    780
ttgaggttga ggctcctgga acagtcacaa ctggaagtcc cagtaactgc catggtcgac    840
ttaattcggg ggacccagtc ccctcttcta accttagtgc ttgcccgtgt gcggcaggcc    900
cgataattac tgaatcccta ctcataattt tcaaaaacac ttggtaggaa gcgtctctac    960
```

```
ggaatactgc ttctgagtac atctgatcag ttgctgcatc gccttcagta agtagtcgct   1020
gtaactgagg actgagttgt tttctcttgt cctttaacat cgcgccaagt gaacgagcag   1080
cttcgtagct catgatggtc ttgtggtcat ctactaaaga cgcaatatga tcgtcccaga   1140
tgaatcgatg tgttcggatt tctctgtcag taaatatttt tttcacggct cgaaggagat   1200
ctgacattgc tggatcaagg ttgagcaacc cggaaccatc ccaaataaag atacttagat   1260
tttcaggatc aactgattgt tctccagctc ttccagagaa gtgtcggtac acataatcta   1320
gatcttcaac gtttcgagtc atgattccca aggaatctaa ggagccactc ataccgtgta   1380
ctcccttcag agaagtacta ccttgtgtca tgaccaagcc tgcggctcca gaaaacgatg   1440
ctggtcgagt gagtgaaccc gcagtttgag tacctagcgc acattgaatc gtgccggccc   1500
caaccgccgc tgcggaaccg ctggaggagc ctccaggagt atgttccaca ctgaatgggt   1560
ttgtgcttga tccaggagca aagtatccat attcagttgt gactgtcttt ccttgtacga   1620
ccgcaccgag atctcgtaat cgcttgcaca atcggcatc attttctcga attgacgggt   1680
ctgcagtctc agaaccacac ctggtcggta gtcctcggac atcgattatg tctttgacgc   1740
caagagaaac tcctcggaga ggttgatccg caccattcgt cgcgcgagca gacgaagacg   1800
ctagttccgt cgataaatct gttagttcaa cccatgcttt caagcgggct tcataacggt   1860
caatttcacg ccgggatttt tgaactaact catcaaccga aacttctcct gcaccaattt   1920
cctttgctgc gtcggagatt gaatttgatc gaaaagttgt aatcatacat tctccctaaa   1980
ttcacaactg aattgaatgt gacaataaat aatgtggaat atgccactct ttttgcctta   2040
tgtgtttcat attaaaacaa cggggcagga gatgacagtt atgaggggt aaaggtttcc    2100
ccagtatcaa tgtaagcaat atcacctcta cgttgaaaac acggacatta gctggctgtc   2160
cagaccatcc gataatcttt gaaatggagt cactgtgaca ataaaaactc agatcggcgc   2220
agagggcgt gaactgacta gctcttccgc gcattcgaaa ggcaacgagc gtaagcgcct    2280
ccgtcgggca tggtcgtgg tattcctgct cgttattttt cagatcatcg catttgccga    2340
taaggccgtt ctggggcttg tctccaccga cgcaatggct gagcttggac taacacccac   2400
ccagttcggt atgatcggca gctcattctt cctgctatat tccattgtct caatcgtcac   2460
tggcgtaatc gcctctcggg tttcggtcca ttggattgtt cttacactcg gagtcatttg   2520
ggctgtcatg cagttcccga tgcttctcgg aggcggagct gctgttcttt tagcaacgcg   2580
aattatcctc ggcggtgctg aaggtccagc tacagcgatg tctctgactt ctgcacacac   2640
atggtttaag ccaaaagagc gcgcattgcc ttccagcctc attgccgctg gtccactttt   2700
ggggccaatc atcgctgcac cggttttgac tctagttatt actgcttggg gctggcgttg   2760
ggcttttgga gtcctgggta tcgtcggcct cgtatggtgc gtatcttggc tgttttcgg    2820
aggaagtggc cccttcttag ccaataagaa gcagcaggta gttacagaca atgcgaaaaa   2880
tattgaacaa gctccagttg ccaaagagtc ctcagtagat gatcagccta gttttccaat   2940
ctggcgcgtt cttcttagcg tctctttcct agccgctctt gtcggagcca catctaactt   3000
```

<210> SEQ ID NO 44
<211> LENGTH: 32
<212> TYPE: DNA
<213> ORGANISM: Artificial sequence
<220> FEATURE:
<223> OTHER INFORMATION: PCR primer

<400> SEQUENCE: 44
ctctcctgca ggtaatggtg tcgaccgaca tc                                  32

<210> SEQ ID NO 45
<211> LENGTH: 32
<212> TYPE: DNA
<213> ORGANISM: Artificial sequence
<220> FEATURE:
<223> OTHER INFORMATION: PCR primer

<400> SEQUENCE: 45
ctctcctgca ggaagttaga tgtggctccg ac                                    32

<210> SEQ ID NO 46
<211> LENGTH: 1617
<212> TYPE: DNA
<213> ORGANISM: Corynebacterium glutamicum

<400> SEQUENCE: 46
atggctagta ccttcattca ggccgacagc cctgaaaaaa gtaagaagct acccccactc      60
acagaaggtc cgtatagaaa gcggctgttc tacgttgcac tagttgcgac gtttggtggg     120
ctgctcttcg gatatgacac cggagtaatc aacggtgcac tcaacccaat gacacgtgag     180
ctcggactaa ccgcgttcac cgagggtgtt gtaacttctt ccctgctgtt tggtgcagca     240
gctggtgcga tgtttttcgg tcgcatttcc gacaactggg gtcgccggaa acaatcatc     300 tcacttgcag tagctttctt tgtcggcacc atgatctgcg tgtttgctcc atcttttgca     360
gtaatggttg tcggacgtgt gcttcttgga ctcgcagttg gtggcgcttc cactgttgtc     420
cctgtctacc tggctgaact tgctcctttt gaaatccgtg gctcactggc tggccgtaat     480
gagttgatga ttgttgttgg tcagctcgca gctttcgtca tcaatgcgat tattggaaat     540 gttttggac accacgatgg tgtgtggcgc tacatgctgg caattgccgc aatcccagca     600
attgccctct tctttggaat gctccgagtt ccagaatccc cacgctggct tgttgagcga     660
ggacgcattg atgaggctcg cgcagttctt gaaaccattc gccctctaga acgtgcccat     720
gcagaagttg ctgatgttga gcacctagca aaagaagagc acgccatttc cgagaagtcc     780
atgggcttaa gggaaatttt gtccagcaag tggcttgtgc gcatcctcct ggtaggtatc     840
ggattgggtg tcgcacagca gctgactggc atcaactcca tcatgtacta cggccaggtt     900
gttctcattg aggctggttt ctccgaaaat gcagctctga tcgccaacgt ggcgccagga     960
gtgatcgcag ttgtcggtgc atttatcgca ctgtggatga tggatcgcat caaccgccgt    1020
accaccctca ttaccggcta ctctctcact accattagcc acgtgttgat cggcatcgca    1080
tccgtagcat tctcagtcgg cgatccactt cgcccatacg ttattttgac cctagttgtg    1140
atcttcgtag gatccatgca gaccttcctc aacgtagcca cctgggtcat gctctccgag    1200
ctcttcccgc tggcaatgcg aggtttcgca atcggtatct cagtgttctt cctctggatc    1260
gcaaacgcgt tcctcggatt gttcttcccc accatcatgg aagcagtagg actaaccgga    1320
accttcttca tgttcgccgg aatcggtgtg gttgccttga tcttcatcta cacccaggtt    1380
cctgaaactc gtggacgtac cttggaggag attgatgagg atgttacttc cggtgtcatt    1440
ttcaacaagg acatccgaaa aggaaaggtg cactaaaaac ccagacactg catagataat    1500
acgctccaga ttttttctcag ccgctgcccc tcccctgctt cgcgcaggtg gaggggcagc    1560 ggtgttttc tttaaagttt ggattccaaa tcaccgaatt cgggagtgaa gcacact        1617

<210> SEQ ID NO 47
<211> LENGTH: 30
<212> TYPE: DNA

<213> ORGANISM: Artificial sequence
<220> FEATURE:
<223> OTHER INFORMATION: PCR primer

<400> SEQUENCE: 47

```
ggagaccata tggctagtac cttcattcag                                   30
```

<210> SEQ ID NO 48
<211> LENGTH: 30
<212> TYPE: DNA
<213> ORGANISM: Artificial sequence
<220> FEATURE:
<223> OTHER INFORMATION: PCR primer

<400> SEQUENCE: 48

```
cctattgcat atgagtgtgc ttcactcccg                                   30
```

<210> SEQ ID NO 49
<211> LENGTH: 3013
<212> TYPE: DNA
<213> ORGANISM: Corynebacterium glutamicum

<400> SEQUENCE: 49

```
gagatcgtac ttcgtaggca tcgctgctcc tgttaactct tggctttctg ctctgtctca    60
gccatactgg accttccagt acaggggaag gtcaagcgcg ccacggagg gagacagcaa   120
tgcggatcgg agaactcgcc gagagggcgg gcactaccgc gaagacccct tcgcttctacg  180
aggaacaggg ccttctgccc cgaccgagc gcacgccgtc cggataccgc gactacgcgc   240
ccgagacggt cgctcggatc gacttcgtcc accgcggcca ggccgcgggc ctcaccctcg   300
cccagatccg ccagatcctc gacatccgcg acggcggcca tgcgccctgc gagcacgtgc   360
gcgacctgct tgacgtgcgc ctcgctgaga tcgagcagca gatcgcgcag ctctccgtgc   420
tgcgcgacac tatcgcggac ctcagacagg acgccgcgca cccggaccct gaaacgtgca   480
gcaccgatca agtgtgtagg tacttgtaat ccaattgggc acacctcctt agcaaccacg   540
ctatgcgaga gttgcagctc gacgagagca agatggcag gattgatcac caggatcgat   600
cttttaaataa ggactatttc ttacctggaa gtaacatttt ggccgttgag gataataccct  660
ttggtgcatt ttgagccaaa aaattcttgg cctctggatt aatagttgcc accacagcac   720
tcgcaaccaa aactgagcct ataataaatg cttctttatt tatctgcagt gattgcagat   780
taaatctttt gttgttgacg tcatgctcca taagcttgtc gtcaaggcgt tctagccgat   840
cgaaagcatc tcggcgactt tcttctgatg aattagggtc gctaataact tgcgtaagta   900
tgcttttcgt cttatcaaaa ctgtcataaa gcctatctga gctgtattta ttgctagata   960
gggcctgttg gaaagaatcg gccattgctt gagacacttt caccatagtg ttatgagaca  1020
cgccctaagc caccgtggcc tccgctgcaa tcatcagggg atcatcaggg gatgacggtg  1080
agtattccac ctaccaacaa ccgcagtgag ggcctccagt gtccaggacg cgagatgttt  1140
tcctgaccgc gtgtgggaag gctggttta tgaagtcgtc ggcatttttc gcttggatga  1200
cctgggggtg gcacttctta ccggtactgg caggccctcc tttccgggtg ggcgctgatc  1260
tagcatggag acatgaatct gcacagcgat gcccgggagt ttctcaagtc ccgcggggac  1320
cgcgtcaccc cgcaggccgc cggcctcccg tcctacggta ggaacgtcg cgtacccggt  1380
ctgcggcgtg aggaagtcgc cctgctggcc ggtgtcagcg tggactatta cacccgcctg  1440
gagcggggaa acctctccgg ggtctccgag gaggtactcg cggcggtggc gggcgccctc  1500
cagctcgacg aagcggaacg ctcccaccctg ttcgacctgg ccaaggccac caactcccag  1560
```

-continued

```
agcctgcggc gcaggaacac ccgcggggct acccgcgccc aggagaaggt ccgcccagag    1620
gtccagcgga tcctcgacgc gatggccgat acgccggcgt tcatcctgac cgaccgcgcg    1680
gacatgctga ccaccaacca gctgggcaga gccctgtttg cacccctgta cgacagcccc    1740
gtctccccgg gcacgagcgg gcaggcgagc acggtaaaca tcgcccgctt cactttcctc    1800
gatccggtgg cccgcgagtt ttttccccac tgggagcaca acgccgccga cctggccgcc    1860
agcctgcgca gcacggccgg gcgccaccct cacgacacgg tcttcagcaa tctcatcggg    1920
gaactggcca cccgcagcca ggacttcgcc caattgtggg ccgaccataa tgtgcggctg    1980
caccgggtgg ggcggaaaac cctgcaccac ccgatcgtcg gggacctgga gctcgacttt    2040
gagactctca tcctgccggc ggacccagac caatccctga tcgtctactc cgccgctccc    2100
ggatccgatg ccgcacagaa cctgcgcctg ctcgccagct ggacggtcac cggtactgat    2160
aaaacaggca ctgacagggc cttccacccg gcggacgatg tccctagtct ggaggaatga    2220
cacctcaatc agcaccctcc caccctgtcc ccaccatcga actcaacaac aacgtgtcca    2280
tgccggcctt aggtttcggg gtgttccaaa cccctcccgc ggacacgatg acggccgtga    2340
ccacggccct gggcaccggc taccggcata tcgacaccgc cgcggccat ggcaacgaac    2400 gcgaggtcgg ccaagccatc gccacttccg ggttgtcccg tcaggaggta ttcatcgaga    2460
ccaaggtctg gatcaccgac tacggctacg ataagaccct gcacgccttc gataagtccg    2520 ccggcaaaact cggcgtagac accatcgacc tgttgatcct ccactaggcg ctgccggagg    2580
actttgaagc cacgatcgag gcctaccggg cgttggagag actgcaggcc gacgggcggg    2640
tccgagcgat tgggggttagc aatttcatgg tcccccacct cgaccgtctc atggaccggg    2700 ccacggtttgc cccggcggtc aatcagctgg agatccaccc ctacttccag cagcgcgagg    2760
tgctcgcccg caacgctgag ctgggaatta tcagccaggc gtggtcaccg atcgggggca    2820
tcaccttcta ccgggacagc ggacatggca gcacccctgga ggatcccacc attggtgaga    2880
tcgcggccga tcatgccaag accccggcgc aggtgatgct gcgctggcac ctgcagcagg    2940
gtcgtcaggt catcccgaag tcggttacgc cctcgcgtat cagggagaac ttcgcggtct    3000
tcgatttcga gct                                                      3013
```

<210> SEQ ID NO 50
<211> LENGTH: 29
<212> TYPE: DNA
<213> ORGANISM: Artificial sequence
<220> FEATURE:
<223> OTHER INFORMATION: PCR primer

<400> SEQUENCE: 50
ctctgtcgac gagatcgtac ttcgtaggc                                     29

<210> SEQ ID NO 51
<211> LENGTH: 29
<212> TYPE: DNA
<213> ORGANISM: Artificial sequence
<220> FEATURE:
<223> OTHER INFORMATION: PCR primer

<400> SEQUENCE: 51
ctctgtcgac agctcgaaat cgaagaccg                                     29

<210> SEQ ID NO 52
<211> LENGTH: 26
<212> TYPE: DNA

```
<213> ORGANISM: Artificial sequence
<220> FEATURE:
<223> OTHER INFORMATION: PCR primer

<400> SEQUENCE: 52
ctctagatct accaactccc agagcc                                          26

<210> SEQ ID NO 53
<211> LENGTH: 27
<212> TYPE: DNA
<213> ORGANISM: Artificial sequence
<220> FEATURE:
<223> OTHER INFORMATION: PCR primer

<400> SEQUENCE: 53
ctctagatct ttggccaggt cgaacag                                         27

<210> SEQ ID NO 54
<211> LENGTH: 972
<212> TYPE: DNA
<213> ORGANISM: Corynebacterium glutamicum

<400> SEQUENCE: 54
atgccacaaa aaccggccag tttcgcggtg ggctttgaca tcggcggcac caacatgcga     60
gctgggcttg tcgacgaatc cgggcgcatc gtgaccagtt tgtcggcgcc gtcgccgcgc    120
acgacgcagg caatggaaca ggggattttt gatctagtcg aacagctcaa ggccgaatac    180
ccggttggtg ctgtgggact tgccgtcgcg ggattttttgg atcctgagtg cgaggttgtt    240
cgatttgccc cgcaccttcc ttggcgcgat gagccagtgc gtgaaaagtt ggaaaacctt    300
ttgggcctgc ctgttcgttt ggaacatgat gccaactcag cagcgtgggg tgagcatcgt    360
tttggtgcag ctcaaggcgc tgacaactgg gttttgttgg cactcggcac tggaattggt    420
gcagcgctga ttgaaaaagg cgaaatttac cgtggtgcat atggcacggc accagaattt    480
ggtcatttgc gtgttgttcg tggcggacgc gcatgtgcgt gtggcaaaga aggctgcctg    540
gagcgttact gttccggtac tgccttggtt tacactgcgc gtgaattggc ttcgcatggc    600
tcattccgca acagcgggct gtttgacaag atcaaagccg atccgaattc catcaatgga    660
aaaacgatca ctgcggcagc gcgccaagaa gacccacttg ctctcgccgt tctggaagat    720
ttcagcgagt ggctgggcga aactttggcg atcattgctg atgtccttga cccaggtatg    780
atcatcattg gtggcggact gtccaatgct gccgaccttt atttggatcg ctcggttaac    840
cactattcca cccgcatcgt cggcgcagga tatcgccctt tggcacgcgt tgccacagct    900
cagttgggtg cggatgctgg catgatcggt gtcgctgatc tggctcgacg ttccgtgttg    960
gaagccaact ag                                                       972

<210> SEQ ID NO 55
<211> LENGTH: 932
<212> TYPE: DNA
<213> ORGANISM: Corynebacterium glutamicum

<400> SEQUENCE: 55
atgactgatc ccacttgcac ccttgcccct gatattggtg ccacaaagat tgcctacgca     60
ctagtccccg ataacgcccc gacgacaaca ttgtccacgg gacgcttggg aacaaaagaa    120
ggcgacagcc ctatcgagca gatccggctg gttcttctgg caggcttaaa agctgccgag    180
gaacacggtc tcagtgtcgc ccgcatcggc atgggcgctc ctggtgtaat tctgggacca    240
gagggaacca tcgtgtacaa cggtgaaacc ctcacagagt gggcaggcac tgacctgcga    300
```

```
ggattatccc gagaagtcct caacgttcca ttcgcggcac acaatgatgt ccgcgtatgg    360
gcctacggtg agcaccactt aggcaccggc aaagacctca ccggcagggt tctctacgtg    420
tccctcggca ctggagtcgg cggagcaatc atcgaagacg gaatcatgat gagtagcccc    480
actggaactg cgggagaatt cgcagaagtt gtgtgctctg accatgcagg attagccgtt    540
cggtgcgaaa atgtagcaag tggcaccggc ctaaccaggt actacaacga ggccgccgca    600
actcaacttg accttcccgc catcatggag cgcttccacc aaggtgacgg cctggcacag    660
caaatcatta ctggaaatct ccgaggcttt ggccaagcgc taggcgcatt agtcacagtg    720
ctggaccttt ccgcagtagt agttggaggc ggagtcgcag gatcggcgc acccgtcatg    780 gatcccatca ccgcagggat tttcgatcga atgttagccc ccaacaaatc cgtacaagtt    840
ttaagcacgt cccttggtgc ccaagcagcc gtcatcgcag cagcaaaata tgcccgcgat    900
aacgcctttt aagcacctaa aacgctgttc tc                                  932
```

<210> SEQ ID NO 56
<211> LENGTH: 1233
<212> TYPE: DNA
<213> ORGANISM: Corynebacterium glutamicum

<400> SEQUENCE: 56

```
gtggcgcgcg gcggtgtaca gcaccccggt gaccacattg atcacagcac ctgctacgac    60
ctcgccgtcg atcgccgcag cgatcgagac ggcgtattgg ggcaggccat aaaggaagtt   120
gacggtgccg tcaatggggt cgacgatcca ggtaactccg cttatcgacg ccgtccccgt   180
cccttcctcg cctatcagcc cgtctttagg ccgaagttcc tgcaacctat tggcgataaa   240
atcttcagcc aaagtatcta ctatcgtcac cggatcgact gtcgaacttt tggtgttggt   300
gtagtcccac aaattggtga gttcagcacg tttatccctg atacgtgtag cggtaagcgt   360
ggcagtttcc gcggcgatgg cacgcaactc attaaacgat tgttgttcca taagaccatc   420
atcgttgttt ttttagaaaa ttgcctgcca aaagccgaag taatttgtac acttgggcgc   480
atgactgaga ctggatttgg aattgatatc ggtggctccg gcatcaaagg cgcccgcgtt   540
aaccttaaga ccggtgagtt tattgatgaa cgcataaaaa tcgccacccc taagccagca   600
accccagagg ctgtcgccga agtagtcgca gagattattt ctcaagccga atgggagggt   660
ccggtcggaa ttaccctgcc gtctgtcgtt cgcgggcaga tcgcgctatc cgcagccaac   720
attgacaagt cctggatcgg caccgatgtg cacgaacttt ttgaccgcca cctaaatggc   780
cgagagatca ccgttctcaa tgacgcagac gccgccggca tcgccgaagc aacctttggc   840
aacgctgccg cacgcgaagg cgcagtcatc ctgctgaccc ttggtacagg tattggatcc   900
gcattccttg tggatggcca actgttcccc aacacagaac tcggtcacat gatcgttgac    960
ggcgaggaag cagaacacct tgcagcagca gccgtcaaag aaaacgaaga tctgtcatgg   1020
aagaaatggg cgaagcgcct gaacaaggtg ctgagcgaat acgagaaact ttctccccca   1080
tccgtcttca tcatcggtgg cggaatttcc agaaagcacg aaaagtggct tccattgctg   1140
gagctagaca ctgacattgt cccagctgag ctgcgcaatc gagccggaat cgtaggagct   1200
gccatggcag taaccaaca cctcaccccca taa                                1233
```

<210> SEQ ID NO 57
<211> LENGTH: 24
<212> TYPE: DNA
<213> ORGANISM: Artificial sequence
<220> FEATURE:

<223> OTHER INFORMATION: PCR primer

<400> SEQUENCE: 57
ctctgcatgc cacaaaaacc ggcc                                          24

<210> SEQ ID NO 58
<211> LENGTH: 29
<212> TYPE: DNA
<213> ORGANISM: Artificial sequence
<220> FEATURE:
<223> OTHER INFORMATION: PCR primer

<400> SEQUENCE: 58
ctctgcatgc ctagttggct tccaacacg                                     29

<210> SEQ ID NO 59
<211> LENGTH: 27
<212> TYPE: DNA
<213> ORGANISM: Artificial sequence
<220> FEATURE:
<223> OTHER INFORMATION: PCR primer

<400> SEQUENCE: 59
ctctcatatg actgatccca cttgcac                                       27

<210> SEQ ID NO 60
<211> LENGTH: 30
<212> TYPE: DNA
<213> ORGANISM: Artificial sequence
<220> FEATURE:
<223> OTHER INFORMATION: PCR primer

<400> SEQUENCE: 60
ctctcatatg gagaacagcg ttttaggtgc                                    30

<210> SEQ ID NO 61
<211> LENGTH: 20
<212> TYPE: DNA
<213> ORGANISM: Artificial sequence
<220> FEATURE:
<223> OTHER INFORMATION: PCR primer

<400> SEQUENCE: 61
ctctcatatg gcgcgcggcg                                               20

<210> SEQ ID NO 62
<211> LENGTH: 29
<212> TYPE: DNA
<213> ORGANISM: Artificial sequence
<220> FEATURE:
<223> OTHER INFORMATION: PCR primer

<400> SEQUENCE: 62
ctctcatatg ttatggggtg aggtgttgg                                     29

<210> SEQ ID NO 63
<211> LENGTH: 3241
<212> TYPE: DNA
<213> ORGANISM: Corynebacterium glutamicum

<400> SEQUENCE: 63
tccagtgtgg atcgcaactc aaaccttcct cacccaactt cgtgatttag acggagtggc    60
cattatcgga acctttgatg atgattcaca caccgttgga ccttccgatg gctggccctg   120
gacgttctat gtgctcgccg atgtcaaaga ccaacccacg gtcaaagaag cctgcaacct   180

```
cctccgcaca atcatggttg gagaacacgc tctatggcgc tacttcaaga tcgaagctcg    240
catgggcaga gaactgacca tccgtgacga cgttgtcgtc tgatcaaaaa actgaaagga    300
ctcaccatga ccaccacaac tagtaaccag acccgattct ctgacctggt cgaagacgac    360
cgtgtcgctg gccagctgta caccgatcct gaaatcttca agaagaaat ggagaagatt    420 ttctataaga cctgggtatg ggtcgctcac gaaagtgaaa tcccagaggc cggatcattt    480
aagaccacat gggtaggcga tcagcctgtc attgtaaacc gagatcgcaa gggcaacttc    540
aacactctgc tcaaccgctg ccgccaccgt ggagcaacag tctgtgacca gcgaaaaggc    600
aaagcaaacg gatttacttg cccttaccac aactggtcct acacccacga tggtcgtcta    660
cgcggagttc cttaccctga cggatacgaa ggtgtgttga aaaaggaaga gcttggcctt    720
caaactctcc gaaccgagag ctacctcggt atgattttg ccaccttcaa tgaagacatc    780
gagcctctag aagatcacct aggtgacgcc aagatttgga tggaacgatt cctcaagcag    840
accaatggat acccttgcaa ggtcattggc gcacacaagt tccgcttcaa cggcaactgg    900
aagatccagc tggaaaatac aaccgacggc taccacttcc ctatggttca caaatcatgg    960
atggcctccg tcgacgcaga aaccgccgac atgatgtcct tcatggatga tcctgaagca    1020
gttactcacg cacttggaaa tggtcacagt gttggaatta tggccactgc tcatatcgat    1080
ttggatgaag acgacggaac tgaagaaatc cagccacgct tcaatcacct cgttaaagaa    1140
cttgaagaag ccggcgaaag cccagagcga atccgacgct tcatgcgatc catgcacggt    1200
tgtggcttca acctcaacat gttccccaac atcgcaatgt cttcttcatt cttccgcgtt    1260
ctaattccaa tctctgtgaa cgagaccgaa atttggcaca tggctatcgg catggacggc    1320
ggtccagaaa gcatcaacca ggaaaaggctc cgcattcacg agcacttcca aggaccattc    1380
ggattcggaa gccccgacga tgctgaaggt tgggaccgag ttcagatcgg tgccggcggc    1440
aaccccaaga tgcccatcct gatcaaccgc ggacttgagc gcgaatacac aaccgaagaa    1500
aactggccaa cctcccatgt caccgatgaa accggcatgc gcgaggctta ctacaagtgg    1560
aagaagctga tgagcaatga ctaacaccac cctccagact gaactgacca acaccagctt    1620
cctaaacgat gagcgagttt tacgcgccat ccagctgatc tggcacgaag ctgccctgct    1680
ggatcgtaaa gactacacaa attgggaaga gctgtttacc gaagatggcc tctacatcgt    1740
ccccatcgat cgtgaaaccg aggacttcca cggctccttg aacatgatct acgacgacaa    1800
gcgcatgcga agcctccgag tccagcgaat gatgcagggc tatgcgcctt ctgctgtcgc    1860
agccgcgatc acaacacgag tcatctctcg gtttgaggtc ttgtcggtat cagacgaaga    1920
ggtcacaatc agctccgcgc aaatcattac tgcgtacaaa cgacacaaca ctgatgtcct    1980
tggagctgac ctcatccaca aaatccgatt ttctgaagat ggaacttcca gaatcgtgca    2040
gaaggtcgca cgcatgatca acagcgaaga tgccatcaat gccgctggtt tctttatcta    2100
aatcccttca atagttagga aactcatgac tgaaaaaacc cagaagattg cacttgttac    2160
cggtgcagct ggtggcctag gcagcttcat tactaagaaa ctccacgctg acgggcacaa    2220
ggtggtcgtc acaggacgtt cctttgaacc acttcaggag cttgcaaatg agctatcagc    2280
agatggaagc acggcactgc cgttgcagct tgatgtgtcg cacaaagaca acttcctgaa    2340
cgcacttgac caggttaaag atgtttgggg aacgccatcc attctggtga caacgcggc    2400 agttacccgt gcagccaacg tcctcgagct caataccgag gaattcgatg aagttcttac    2460
caccaatgtg aacagtatct tcttcggatg ccaagtattc ggaattgcaa tggcggagca    2520
```

| | |
|---|---:|
| aggatacggt cgcatcgtta accaagcatc ccttgccggc aaaacggtg gaactgctac | 2580 |
| tggagctcac tacgctgctt caaaaggcgc gatcttaaca accaccaagg tattcgcgcg | 2640 |
| cgaatttgct ggctcgggag taaccgttaa cgctatctca cctgggccac acgatgtgga | 2700 |
| catcgtccac acaacagttg cagaccacct ggaacaaatt gtggaaggaa tccctgtcaa | 2760 |
| acaacttggc aatcctcagt tcatcgccaa cactgtttcc ctgctcacac aacccgaagc | 2820 |
| aagctttgtt accggcgcat gctgggacat caatggcggc ctctacctgc gttaacccc | 2880 |
| cgtacaccat ctggaaagtg aggaaacagc aatgtctatg aaagaagtta ttgtcacaga | 2940 |
| tctcgtctat gaaacgccga cgatcatctc aatccatcta gcaaaactag acggcacgcc | 3000 |
| cattgggcac tacgttcccg gcgcacacat cgatgtcgaa ggtccaactg cagtaacgag | 3060 |
| gcaatactcc ttatgtggac gcccagatgg tgacgacgcc tatgtcgttg cagtaaagcg | 3120 |
| agagccagcc tcccgtggtg gttctgaagc tttgcaccag ctcagcgttg gtgaccacct | 3180 |
| gaagatttca gaacctcgaa acctcatcgg tatcgcagat caagctagtc accatatcct | 3240 |
| c | 3241 |

<210> SEQ ID NO 64
<211> LENGTH: 2520
<212> TYPE: DNA
<213> ORGANISM: Corynebacterium glutamicum

<400> SEQUENCE: 64

| | |
|---|---:|
| caccgttgtc agcttcactg tcagggaggc tggcgatacc tttattgatc tccgcgcagc | 60 |
| aagcgttgag gaggttcgcc tggacaatgt gtccatcaaa gatgaggctc taacccttgg | 120 |
| caagaacggc tacgacgaga cgttcggcat cgccctgaag ggtcttactc ccggcgcgca | 180 |
| caccttgcgg gtaacggcga ctatcccta ttcccgcacc ggtgaaggcc tgcaccgcat | 240 |
| ggtggatcca gcagacaatg aggtgtattt gtacacccag tttgagaccg ccgatgccaa | 300 |
| gcgtatgttc gcgtgtttcg atcagccaga cctcaaggct acctatgatc tgaacatcaa | 360 |
| aactcctaag ggttggaaga ttatttccaa ctctgagcag caggtttcca ctcagcacac | 420 |
| tgattacgat acccacattt cccgagtgga ctatccccctc tccacctacc tgattgcggt | 480 |
| gtgcgcgggt cgttaccacg aggtgcgcga tgtctggaag ggtacgctca cccaccatgc | 540 |
| agaaacacct gccgatcagc caactgagct gactgttccg cttgctctct actgccgcag | 600 |
| ttctttggct aaagatcttg atgcggagcg tctgtttacc gaaacgaagc agggctttga | 660 |
| ttggtaccac cgcaacttcg gtgtggcgta cccattcggc aagtacgatc agatcttcgt | 720 |
| ccctgaattt aacgccggtg caatggaaaa cgcaggtgcg gtgactattc gtgatgaata | 780 |
| cgtctttgct tccaaggcca cccattaccg ctatgagcgt cgtgcggaaa ccatcctcca | 840 |
| cgaactcgct cacatgtggt tggtgatct agtcacgatg caatggtggg atgacctgtg | 900 |
| gctcaatgaa tccttcgcta cctggtcggc tgtgatttcc caggctgagg aaactgaata | 960 |
| caacactgca tgggtgactt ttgccaacgt ggagaagtcg tgggcgtacc agcaggatca | 1020 |
| gctgccttcc acccacccgg tgttctctga cggctacgat attgaaaccg tcgatcagaa | 1080 |
| cttcgacggc atcacctacg caaagggcgc ctcggtgctc aagcagctgc aggcatacgt | 1140 |
| tggccgcgag gaattcctgg ctggcgtacg caggcacttt gccaaccacg catgggcaa | 1200 |
| cgccagcttc gatgatctgc tcggcgccct cgagcagtct tccggccgcg acctttccga | 1260 |
| ctgggcaaac cagtggctca agaccaccgg catcaacacc ctcggcgcca gttcaccac | 1320 |
| cgacaacggc aaatacacct ccttctccgt cacccagacc ggtgccgcgc cgggtgccgg | 1380 |

```
tgagctgcgg actcaccgca tcgcggtggg tctttataag cttgtcgacg gatccctcaa    1440
ccgctacgca cgagtagaac ttgactgcag tggcgcgtcg acaagcgttg aagagatcgt    1500
tggacttgag caggctgact tcgtgctggt caacgatgat gatctgacgt atgcgctgct    1560
ggatctggat gatgattcac gcaattttgt catcgacaat attgataagt tcagcgaccc    1620
tatgcctcgc acgctggtgt ggtccgctgc gtgggagatg actcgcgctg gtcagatgaa    1680
ggctcgtgat tcatcgcgc tggttgctcg tggcgctgct gcggaaacgg aaatttctgt    1740
gctggagcgc attctcgcgc aggcaacctc tgcgctgaag agctacgccg acccagcctg    1800
ggcagaaaca accggaaatg acctgcttgc cgatgctttc cttgagggtg ctcgctccgc    1860
agaaccagac tccgacaccc agctggcatt catccaagca ctggccaagg caacgctcaa    1920
tgatgctgct gccgattact tccgcgacat tcttgccggc aacgtcgaag gcctgaccgt    1980
ggatcctgac ctacgttggt gggcgctgac cgcactcatc gctcgcggtg acatcgaggc    2040
acctgaggaa gcaatttcca ccgagctatc ccgcgataac tccagcgctt ccttcctcgc    2100
ttcacttcga gctggagcag ctgtgaacac tgaagctgta aaggctgccg catacaagga    2160
ggtcaccgcg ctggacagtg gcttgtccaa cctggagctg cgccacaaga ttgaaggcct    2220
cacattcact ggctcttctg aactgctgca agcctacaac gagcagtact tcgaaatcct    2280
tgatgatgtg tgggcgaact tctccggcga aatggcacag cagatcgtcc tcggactgtt    2340
cccttcatgg aacgtttccg aagagggtct caagcgtacc gacgagttcc ttaatggcga    2400
acatgtcgca ggcatcaaac gaattgtttc cgaatcccgc gaccgcaccg cccgtgccct    2460
gcgcaaccgt gaggcagatg ctgcgtagct attgattctg tagaggtatg ccacagtcag    2520
```

<210> SEQ ID NO 65
<211> LENGTH: 3139
<212> TYPE: DNA
<213> ORGANISM: Corynebacterium glutamicum

<400> SEQUENCE: 65

```
ttgggaactt agctaggtcg ctgagctcgc ggaagtcatc gggatgtacg ccgatttcgt      60
caaaggcctg gcggtagtgc ttcacattgt agtaggagtg acgcagcgtg ttcttcgcac     120
gttcggtctg gagtgcggtg atctcgtcgc gagatgcgaa ttcgattcca gttgttggtc     180
cattgtgggt ggaagagatg ttgtatacgg aggtcacgtg cgtagcgcct ttctagattg     240
tttcagctcg caggccaaga aattggtgtg tgcgtctaac ggaagtcgaa caaacgtcga     300
acatgaatcg tgctgtggaa atgtgttgtg acgcggtgtc tcgcttgata tatccattct     360
gcctgtggga gaaggactaa ggaagcaata tcaatttcca ttaacttacc gaccttccgg     420
tcagtaagtt gtgagctacg ctacacgtgc tttgaaatgt tgtccacgat atggtgactg     480
tggggtgagg ggcacccca tttacgaagt ttgtgaaggg cggattgtga cagtctaagt     540
gctgggtgtg gctgttttaa gtccagagag cactaattct gcggtggtgt ctgcgatttc     600
ttcgggggta agcttgccac cagcttcata ccagtcggtc agtgagttta cggtgccgaa     660
aatgaggcgt ccgaccactc cggcgtctag gtcaggacga atttctcctg cttcttgagc     720
atgaactacc aggtcaatca tggcgcgggt gagttcacgg cgtcgtttca ttgcctctag     780
ctcggcttca gagttgccac gaagtcgaag gaggagggtg acttgtgctt tgtgttcaca     840
cagaacggca atggatcctt tgatgagaaa aactagttga gctttggggc cacctgtttg     900
ttcccatgct tcggtggaga tctcttcgag gctggttagt gctaggtctg tggcctcctg     960
```

```
gaggatttct tctttggagg tgacgtggtg atagatggca gattttgtaa ttcctaagcg    1020
tttggccaag gtacccatcg aggttgcttc gtatccgtgg gcgttgaatt cattgaccgc    1080
ttcagaaatt acttgggcgc gagaatatcc aggacggccg cggccggtgg cgggaagcgc    1140
ttgggaaatg ctcgttggag tcatgatttc ttactcactt tcttgcgccg aaggtggagc    1200
aatgggaaat aaaatgggaa ttctcgagtg aaatacttct aagaaactgt agactttctc    1260
aaccataacc gggaaagggc ctggttatgt agaaatcact ctagagggaa gttgggatt     1320 taccatgtct gaaactgcgg ttgatatttc acaaattgag tctgacctgg aatttactcg    1380
agcgatgtat gaaaacgatg gctcgttgaa ggccatgggt atttccatta ccaagttgga    1440
aacgggtcat gttgaggggg aatttattgt ccgtcctgag atgtgcaatg gcataattc     1500 catccagggt ggattcttgt tcaccttcgc tgacgcactt tttgctggtg cgtgtaattc    1560
caccagggga gcggtcactg ttgcatccca ggtgcagatc catttcattg cgccggcttt    1620
tgcgggtgaa acacttcggg gtgtggctat tgagcgtcag tcatggggca ggaatggtct    1680
gtctgatgtc actgttttcc gtggtgacaa ggttattgca gagtttcggg gaatgtctcg    1740
aactgtcggg aagcgcgcct aacgctttgc tggggtgtgg gttttctacc cccggttcac    1800
ccctgtgagc tggtttgttg tagaaatcta cccccgcatc acgtcctgtc gatcgcggaa    1860
agattgaccc agatcacact atctggatat cctgaccgaa cgatcggtaa ttaaatgatt    1920
cccgtaagga ggaaggtcat catgactaca gcagttgcac ctgacacaaa cgcagataca    1980
gctgggcaac agcgcttcga tgagatcatc gcggcggatt cccgaattga acctactgac    2040
tggatgccag cggcataccg caagacactg acccgccaga tttctcagca cgcacactct    2100
gagatcatcg gcatgcagcc tgaggctaac tggatttccc gagcaccatc tctgaagcgc    2160
aaagcaatcc tgatggccaa ggttcaggat gaagcaggcc acggcctata cctgtactcg    2220
gctgctgaaa cactgggcac ctctcgcgat gagctggtta atcagcttct ggaaggcaaa    2280
gccaaatatt cctccatctt caattaccca gctcgcacct gggcagacat cggagcaatc    2340
ggctggttgg ttgatggcgc tgctatttgt aaccaggtgc cactctgccg cgcttcctat    2400
gcgccatatg ctcgcgcaat ggttcgaatc tgtaaggaag aatccttcca ccagcgccaa    2460
ggctgggaaa ttttgtacga actttcccat ggcaccccag agcaaaagca gatggcacag    2520
gaagcaatca accgcttgta ccgtccagca ctgcaaatgt tcggaccacc ggatgcagat    2580
tctgcgcact ctggacagtc catgaaatgg aacattaaac ggttctccaa tgatgagctg    2640
cgtcagcgtt tcgtcgacat gattgttccg caggttgagg cactgggact gacgtttgaa    2700
gatccggatc tgaaatggaa cgaggaacgc ggtcactacg acttcggaga gctcgattgg    2760
gatgagttct tcaatgccat taatggtaac ggaccgctga attccaacg tttgaagcga     2820 cgtcgagaag cattcgatga cggcgcctgg gtgcgcgagg ctgccgcggc ctacgaccgc    2880
aagcacaacc gctcgacac tgcattagtt gtttaaaccg agaaggaaat agagaacatg     2940
tctgattcaa cttggcctca gtttgaggta tttgttcgct caaaccgcgg attatcccac    3000
gtccacgctg gctctttgca cgcgccagat gaaaccatgg cactgcgcaa cgcacgcgat    3060
ctgtacaccc gccgcaacga aggcacctcc gtgtgggtcg ttccatccca ggcgatcacc    3120
gcatctgatc ctgattcca                                                 3139
```

<210> SEQ ID NO 66
<211> LENGTH: 30
<212> TYPE: DNA
<213> ORGANISM: Artificial sequence
<220> FEATURE:
<223> OTHER INFORMATION: PCR primer

<400> SEQUENCE: 66
ctctcctgca ggtccagtgt ggatcgcaac         30

<210> SEQ ID NO 67
<211> LENGTH: 33
<212> TYPE: DNA
<213> ORGANISM: Artificial sequence
<220> FEATURE:
<223> OTHER INFORMATION: PCR primer

<400> SEQUENCE: 67
ctctcctgca gggaggatat ggtgactagc ttg         33

<210> SEQ ID NO 68
<211> LENGTH: 31
<212> TYPE: DNA
<213> ORGANISM: Artificial sequence
<220> FEATURE:
<223> OTHER INFORMATION: PCR primer

<400> SEQUENCE: 68
ctctcctgca ggcaccgttg tcagcttcac t         31

<210> SEQ ID NO 69
<211> LENGTH: 32
<212> TYPE: DNA
<213> ORGANISM: Artificial sequence
<220> FEATURE:
<223> OTHER INFORMATION: PCR primer

<400> SEQUENCE: 69
ctctcctgca ggctgactgt ggcatacctc ta         32

<210> SEQ ID NO 70
<211> LENGTH: 32
<212> TYPE: DNA
<213> ORGANISM: Artificial sequence
<220> FEATURE:
<223> OTHER INFORMATION: PCR primer

<400> SEQUENCE: 70
ctctcctgca ggttgggaac ttagctaggt cg         32

<210> SEQ ID NO 71
<211> LENGTH: 32
<212> TYPE: DNA
<213> ORGANISM: Artificial sequence
<220> FEATURE:
<223> OTHER INFORMATION: PCR primer

<400> SEQUENCE: 71
ctctcctgca ggtggaatca ggatcagatg cg         32

<210> SEQ ID NO 72
<211> LENGTH: 30
<212> TYPE: DNA
<213> ORGANISM: Artificial sequence
<220> FEATURE:
<223> OTHER INFORMATION: PCR primer

<400> SEQUENCE: 72
ctctgatatc cttcctaaac gatgagcgag         30

<210> SEQ ID NO 73
<211> LENGTH: 30
<212> TYPE: DNA
<213> ORGANISM: Artificial Sequence
<220> FEATURE:
<223> OTHER INFORMATION: PCR primer

<400> SEQUENCE: 73
ctctgatatc ttggtcagtt cagtctggag    30

<210> SEQ ID NO 74
<211> LENGTH: 30
<212> TYPE: DNA
<213> ORGANISM: Artificial sequence
<220> FEATURE:
<223> OTHER INFORMATION: PCR primer

<400> SEQUENCE: 74
ctctagtact gcagatccat ttcattgcgc    30

<210> SEQ ID NO 75
<211> LENGTH: 29
<212> TYPE: DNA
<213> ORGANISM: Artificial sequence
<220> FEATURE:
<223> OTHER INFORMATION: PCR primer

<400> SEQUENCE: 75
ctctagtact tggtggaatt acacgcacc    29

<210> SEQ ID NO 76
<211> LENGTH: 2494
<212> TYPE: DNA
<213> ORGANISM: Corynebacterium glutamicum

<400> SEQUENCE: 76
ctcagattgg tttcgcagtc tctggtggtt tcgtcccagt tatcgcatcc gcgcttgctg    60
gtgatcaggg tgaccagtgg atgaaggtgt ccatcttcgt tggtgttgtt tgtgtgattt    120
ctgcactggt tgccatgacc gctaaggaaa ccaaggctct gactggat gagatcgatg     180
ctctgcacac tgctcgtggt gaggccgcag acctggcagc cgcaaacaaa gcctccgagg    240
cccaactcgc ggctaagtaa aatcacgtaa ccaaagaaaa ggactctttg accacatgcg    300
tacatccatt gccactgttt gtttgtccgg aactcttgct gaaaagctgc gcgcagctgc    360
agatgctgga tttgatggtg tggaaatctt cgagcaggac ttggtggttt ccccgcattc    420
ggcagagcag attcgtcagc gggctcagga tttgggatta ccctggatc tgttccagcc     480
gtttcgagat ttcgaaggtg tggaagaaga gcagtttctg aagaatctgc accgcttgga    540
agagaagttc aagctgatga acaggcttgg cattgagatg atcttgttgt gttccaatgt    600
gggcaccgcg accatcaatg atgatgacct tttcgtggag cagttgcatc gtgcagcaga    660
tttggctgag aagtacaacg tcaagattgc ttatgaagcg ttgcgtgggg gcaagtttgt    720
caatgatttt gagcatgcgc atgcacttgt ggagaaggtg aatcacaagg cgctgggaac    780
ctgcttggat acgttccata ttctttcccg tggttgggaa accgacgagg tggaaaacat    840
cccggcggag aagatcttct tgttcagtt ggcggatgca ccgaagctga gcatggacat    900
tttgtcctgg tcgcgtcacc accgtgtttt ccctggtgaa ggcgatttcg atctggtgaa    960
attcatggtt catctggcca agacgggtta tgatggcccg atttctttgg agatcttcaa    1020
cgattccttc cgcaaggccg aggttggtcg caccgcgatt gatgggttgc gttctttgcg    1080

```
ttggttggaa gatcagacct ggcatgcgct aaatgctgag gatcgtccaa gcgcactaga    1140
gctgcgtgca cttcctgagg tcgcggaacc tgaaggcgtt gatttcattg agatcgccac    1200
tggacgtttg ggtgagacca ttcgggttct tcatcaattg ggtttccgct tgggtggtca    1260
tcactgcagt aagcaggatt accaggtatg acccagggc gatgtgcgca ttgtggtgtg     1320
tgatcgtggg gccaccgggg ctccaaccac gatctctgcg atgggctttg acacccctga    1380
tccagaagcc gcgcatgccc gtgcggaatt gctgcgggct cagacaattg atcgtcccca    1440
catcgagggt gaagttgacc ttaaaggtgt gtacgcgccg gatggggtgg agctgttttt    1500
cgcggggccg agcccgatg gaatgcccga gtggctgccg gaattcggcg tcgaaaagca     1560
agaagctggt ctcattgaag ccatcgacca cgtcaatttc gcccagccat ggcaacattt    1620
tgatgaggca gtgctgtttt acaccgcgct gatggcgtta gagactgtgc gtgaggatga    1680
gttcccgagc ccaattggtt tggtgcgcaa tcaggtgatg cgttcgccga atgatgcggt    1740
gcggttgctg ctcagcgtgg cgccggagga cggtgagcag ggagatttcc tcaacgcggc    1800
ctacccggag cacattgcgt tggccacggc ggacatcgtg gcggtggctg aacgtgcgcg    1860
caaacgaggc ctggatttct tgcccgtccc agagaattac tacgacgatg tgcaggcgcg    1920
ttttgatttg ccgcaggaat tcttggacac actcaaggaa aaccacctgc tttacgactg    1980
cgacgagaac ggcgaattcc tccactttta cacccgcacg ttgggcacgc tgttcttcga    2040
agtggtggaa cgccgcggcg gttttgcagg ttggggcgaa acaaacgctc cggtgcggtt    2100
agcggcgcag tatcgtgagg tgcgggacct cgagcgggga atccccaact agcatcccga    2160
actagccccc ccaacaacaa ttagaaaagg aacctaaaat gcttggaaaa attctcctcc    2220
tcaacgcccc aaacctgaac atgctgggca acgcgagcc tgacatttac ggacacgaca     2280
ccttggaaga cgtcgtcgcg ctggcaaccg ctgaggctgc gaagcacggc cttgaggttg    2340
aggcgctgca gagcaatcac gaaggtgagc taatcgatgc gctgcacaac gctcgcggca    2400
cccacatcgg ttgcgtgatt aaccccggcg gcctgactca cacttcggtg gcgcttttgg    2460
atgcggtgaa ggcgtctgag cttcctaccg ttga                                2494
```

<210> SEQ ID NO 77
<211> LENGTH: 1983
<212> TYPE: DNA
<213> ORGANISM: Corynebacterium glutamicum

<400> SEQUENCE: 77

```
gttcttcgaa gtggtggaac gccgcggcgg ttttgcaggt tggggcgaaa caaacgctcc      60
ggtgcggtta gcggcgcagt atcgtgaggt gcgggacctc gagcggggaa tccccaacta     120
gcatcccgaa ctagcccccc caacaacaat tagaaaagga acctaaaatg cttggaaaaa     180
ttctcctcct caacggccca aacctgaaca tgctgggcaa cgcgagcct gacatttacg      240 gacacgacac cttggaagac gtcgtcgcgc tggcaaccgc tgaggctgcg aagcacggcc     300
ttgaggttga ggcgctgcag agcaatcacg aaggtgagct aatcgatgcg ctgcacaacg     360
ctcgcggcac ccacatcggt tgcgtgatta accccggcgg cctgactcac acttcggtgg    420
cgcttttgga tgcggtgaag gcgtctgagc ttcctaccgt tgaggtgcac atttccaatc    480
cgcatgcccg tgaagagttc cgccaccatt cttacatttc cctcgccgcg gtctccgtta    540
tcgctggcgc tggcatccag ggttaccgtt tcgcggtcga tatcctggca aatctcaaaa    600
agtagaaagc ccaaaaaata tgaacgacag tattctcctc ggcctaatcg gccagggcct    660
```

-continued

| | |
|---|---|
| cgacctatcg cgcaccccg caatgcacga ggcggaaggc ctcgcgcagg gacgtgcgac | 720 |
| cgtgtacagg cgcatcgaca cgcttgggtc gcgtgcttcc gggcaagatt taaagacgct | 780 |
| tctcgacgcc gccctctacc ttggcttcaa cggcctgaac atcactcacc cgtacaaaca | 840 |
| agcagtatta cccctgcttg acgaagtctc cgaacaagcc acccaactcg cgcagtgaa | 900 |
| tactgtcgtt atcgacgcca acggccacac caccggccac aacaccgacg tctccggatt | 960 |
| tggccgcgga atgaagaag gcctccccaa cgccaagctc gattccgtcg tgcaggtcgg | 1020 |
| cgccggcggc gtaggaaacg cagtggcata cgccctggtc acccatggtg tgcagaaact | 1080 |
| tcaggtcgct gacctcgaca cttcccgcgc acaggcatta gcggatgtca tcaacaatgc | 1140 |
| agtcggccgc gaagctgtcg tgggagtaga cgcccgcggc atcgaagacg tcatcgcagc | 1200 |
| cgccgacgga gtagtcaacg caaccccccat gggaatgccc gcacaccccg gcaccgcctt | 1260 |
| tgatgtcagc tgcctcacca aggatcactg ggttggcgac gtcgtgtaca tgcccatcga | 1320 |
| aactgaactt ctcaaggccg cccgtgccct cggctgcgaa accctcgacg gaacccgcat | 1380 |
| ggcaatccac caagccgtcg atgccttccg cctgttcacc ggcctcgaac ccgacgtctc | 1440 |
| ccgcatgcgg gaaactttcc tatccctcta aagagtcag taaaacctcg acgcttcgac | 1500 |
| cgtttccttc gcttccttca accctgcccc ggtaagttca cggtgacgtt tgatcgccgc | 1560 |
| gatcttctta ccctgctgca ggagcgccac aacgtcagga tgtaaccctg attgtggtct | 1620 |
| ttgcaacgac agcggagtcg aagaatcacc ccctagctga gcaatgatct gatcttgctc | 1680 |
| agctagtctg cgttcaagag cagcaacacg agcttccaat gcactgagat ttatgtcttt | 1740 |
| tctaccaaac atgccccca aataggtga gcgtttagtt ccgggggtgc cggtttcgcg | 1800 |
| ggctcaattt ctcatgacga acttaagcag ggtctgcacc catacacggt agaataagtg | 1860 |
| ctacggttcg acttcacgtg cgctgacttc tcatgctcaa cttcttgtca tacgacttca | 1920 |
| gtaggaaatc cggtgatcgc ctaatgaagt ctgcacatga gaagtcgccc tttaaggtga | 1980 |
| tca | 1983 |

<210> SEQ ID NO 78
<211> LENGTH: 2664
<212> TYPE: DNA
<213> ORGANISM: Corynebacterium glutamicum

<400> SEQUENCE: 78

| | |
|---|---|
| ttgtggtaga ccttgggtgg ataatgattc gatcgatgtg gcgactagaa ccatgccgac | 60 |
| gatcctcttc cgaagtgagt gatctgcccg tttaaccagg ttaagtgccg tgagtccgcc | 120 |
| gagggaatgc ccaaccaaaa tgagcgggcc ggtcggtgcg tgttcgtgga tggctgcgag | 180 |
| aacatcgttc gctgttcctt cgatggtgca gagctctggg cggacctggc cggtggcgcc | 240 |
| gtggccgcgg gcgtcgataa gcacgctttt aatatttggg taaaaggttt gtaggtagtc | 300 |
| gacctgcatg taatacactt cggcggcgag ggtgaagccg tggatgaaca cgaccgttgc | 360 |
| cgtggcattt tcagcatggc caaccgtgta cgtgtggatg ctgaggccgt cggagtccac | 420 |
| gatggtgtgg cggtcgacgt gttttagacc cggggtacgg ttttttgctaa atgctgcgcc | 480 |
| acgctccagg aggagttgcc tgcgaccatt tggcgtcatc tttagccttg ctttatgagc | 540 |
| ttttccccgc aatgagccgc gttgtgtatc cataagtctt agcctacaag cgctttgagg | 600 |
| tagtttggga tcatggattt caacgacaaa gccgcttcag aaaacgctgt aaagactggc | 660 |
| gcagaaggcc ccaacgtttt cgcgaacgtg gccaagattt gcaggatgt tggcggaatt | 720 |
| tcagccgaag acgtcactcc ggaatctcgt tttactgagg atttggcagt cagctcactc | 780 |

```
aattacatcg agttgattgt caatgcggag gacgcgtttg gtgtccgcat tgaggattcc    840
gatgccaagg atttgaccac cgtgcaggat ttgattgact ttattaacac caataaggct    900
gattagcggg aaaatttcgc ccaaaacagg gacaatggtg ttatgacagt gaacatttca    960
tatctgaccg acatggacgg cgtcctcatc aaagagggcg agatgattcc gggtgcagat   1020
cgttttcttc agtctctcac cgataacaat gtggagttta tggttttgac caacaactcc   1080
attttcaccc cgagggatct ttctgcacgt cttaagactt ccggtttgga tatcccgccg   1140
gagcgtattt ggacttctgc aaccgccact gctcacttcc tgaaatccca ggtcaaggag   1200
ggcacagcct atgttgttgg cgagtctggt ctgaccactg cgttgcatac cgcgggttgg   1260
attttgacgg atgcaaatcc tgagtttgtt gtcctgggcg aaacccgcac gtattccttc   1320
gaggcaatca ccactgctat aaatctgatt ttgggcggcg ctcgctttat ttgcaccaac   1380
ccggatgtaa caggaccttc accaagtggc attttgcctg ctactggctc tgtcgcagcg   1440
cttattaccg cagctacagg cgctgagcct tattacatcg gtaagccaaa ccctgtgatg   1500
atgcgcagtg cgctgaacac catcggggcg cattccgagc acactgtcat gatcggcgac   1560
cgcatggaca ccgacgtgaa atctggtttg gaagccggcc tgagcaccgt gctggttcga   1620
agcggaattt ccgacgacgc cgagatccgc cgctaccct tccgcccaac tcacgtgatc   1680
aattccatcg ccgatcttgc cgattgctgg gacgatcctt tcggtgacgg tgcatttcac   1740
gtaccagatg agcagcagtt cactgactag tattctgtag gtcatggcat ttgcagacat   1800
tgtgcgcagc gtcgaaaacc gcaccaacgc agcgaccctc aactggtcca tcaaaaaggg   1860
ctggaagccc gaagtcaccg gattttccgg gtacggctcc gggcgtcgag tgcgcgtcct   1920
tgcgcgcgtg ctcatgtcca accccgaaaa tttgcttgtc gacgccccct cccaatcaat   1980
tacccaacaa gcacagcgcg gttggcgcca gttcttcacc atccaagtgc caacctgcc    2040
agtaactgtc accgttggtg ggaaaacagt tacctcatcc accaacgaca acggctacgt   2100
tgacctcctg gtggaagacc acaaccttga ccccggctgg cacaccatcc agatccaagc   2160
cgaaggttcc acccccgccg aagcccgcgt cctcatcgtg gaaaacaccg cccgaatcgg   2220
actcatctcc gacatcgacg acaccatcat ggtcacctgg cttccccgag cactcctcgc   2280
cgcatggaac tcgtgggttt tgcacaccaa cacccgcaaa ccagtccccg gaatgaaccg   2340
cttctacgaa gaactcctca agacccaccc cgacgcaccc gtgttctacc tctccaccgg   2400
cgcatggaac acctttgaaa ccctccaaga gttcatcaac aaacacgcat tccccgacgg   2460
ccccatgctg ctcaccgact ggggaccaac ccccacagga ctattccgct caggtcaaga   2520
gcacaagaaa gtccaactgc gcaacctgtt tatcgaatac cccgacatga aatggatcct   2580
cgtcggcgac gatggccaac acgatcccct catctacggc gaagcagtcg aagaacaccc   2640
caaccgcatc gcaggtgttg caat                                          2664
```

<210> SEQ ID NO 79
<211> LENGTH: 30
<212> TYPE: DNA
<213> ORGANISM: Artificial sequence
<220> FEATURE:
<223> OTHER INFORMATION: PCR primer

<400> SEQUENCE: 79
ctctgtcgac ctcagattgg tttcgcagtc                                      30

<210> SEQ ID NO 80

```
<211> LENGTH: 40
<212> TYPE: DNA
<213> ORGANISM: Artificial sequence
<220> FEATURE:
<223> OTHER INFORMATION: PCR primer

<400> SEQUENCE: 80
ctgattgcgc accaaaccaa gaacgtatcc aagcaggttc                              40

<210> SEQ ID NO 81
<211> LENGTH: 20
<212> TYPE: DNA
<213> ORGANISM: Artificial sequence
<220> FEATURE:
<223> OTHER INFORMATION: PCR primer

<400> SEQUENCE: 81
ttggtttggt gcgcaatcag                                                    20

<210> SEQ ID NO 82
<211> LENGTH: 29
<212> TYPE: DNA
<213> ORGANISM: Artificial sequence
<220> FEATURE:
<223> OTHER INFORMATION: PCR primer

<400> SEQUENCE: 82
ctctgtcgac tcaacggtag gaagctcag                                          29

<210> SEQ ID NO 83
<211> LENGTH: 30
<212> TYPE: DNA
<213> ORGANISM: Artificial sequence
<220> FEATURE:
<223> OTHER INFORMATION: PCR primer

<400> SEQUENCE: 83
ctctgtcgac gttcttcgaa gtggtggaac                                         30

<210> SEQ ID NO 84
<211> LENGTH: 39
<212> TYPE: DNA
<213> ORGANISM: Artificial sequence
<220> FEATURE:
<223> OTHER INFORMATION: PCR primer

<400> SEQUENCE: 84
gtgaggcagc tgacatcaaa cgttgaagcc aaggtagag                               39

<210> SEQ ID NO 85
<211> LENGTH: 20
<212> TYPE: DNA
<213> ORGANISM: Artificial sequence
<220> FEATURE:
<223> OTHER INFORMATION: PCR primer

<400> SEQUENCE: 85
tttgatgtca gctgcctcac                                                    20

<210> SEQ ID NO 86
<211> LENGTH: 30
<212> TYPE: DNA
<213> ORGANISM: Artificial sequence
<220> FEATURE:
<223> OTHER INFORMATION: PCR primer

<400> SEQUENCE: 86
```

-continued ctctgtcgac tgatcacctt aaagggcgac                                30

<210> SEQ ID NO 87
<211> LENGTH: 29
<212> TYPE: DNA
<213> ORGANISM: Artificial sequence
<220> FEATURE:
<223> OTHER INFORMATION: PCR primer

<400> SEQUENCE: 87
ctctctgcag ttgtggtaga ccttgggtg                                 29

<210> SEQ ID NO 88
<211> LENGTH: 22
<212> TYPE: DNA
<213> ORGANISM: Artificial sequence
<220> FEATURE:
<223> OTHER INFORMATION: PCR primer

<400> SEQUENCE: 88
aacaccattg tccctgtttt gg                                        22

<210> SEQ ID NO 89
<211> LENGTH: 50
<212> TYPE: DNA
<213> ORGANISM: Artificial sequence
<220> FEATURE:
<223> OTHER INFORMATION: PCR primer

<400> SEQUENCE: 89
tcgcccaaaa cagggacaat ggtgtttatt ctgtaggtca tggcatttgc          50

<210> SEQ ID NO 90
<211> LENGTH: 29
<212> TYPE: DNA
<213> ORGANISM: Artificial sequence
<220> FEATURE:
<223> OTHER INFORMATION: PCR primer

<400> SEQUENCE: 90
ctcttctaga attgcaacac ctgcgatgc                                 29

<210> SEQ ID NO 91
<211> LENGTH: 2185
<212> TYPE: DNA
<213> ORGANISM: Corynebacterium glutamicum

<400> SEQUENCE: 91
ggaggtgctc tctcacgtaa tttccattgg tgcgtccgag ccttacgtcg gcgcggagcc     60
aacctttgca gatattcaag caatcgatga ttccccagtt cgtgcattcg gtaaagacgc    120
tgaaaaatcc atgatcgcgg aaatcgaggc cgcaaagaaa gccggcgata ccctcggtgg    180
catcgtggaa gtgattgttg aaggcctacc catcggtttg gctcacaca tttctggcga    240 agatcgcctc gatgcgcaga tcgcagctgc actcatgggc attcaggcca tcaagggcgt    300
ggaaatcggt gacggtttcg aagaagctcg tcgacgtggc tccgaagccc acgatgaagt    360
gttcctggat gacaacggcg tataccgcaa caccaaccgt gcaggtggcc tcgaaggcgg    420
catgaccaac ggtgaaaccc tgcgcgttcg tgctggcatg aagccaattt ctactgtgcc    480
tcgcgccctg aaaaccattg atatggaaaa cggcaaggca gcaaccggaa tccaccagcg    540
ttccgacgtg tgcgctgttc cagccgccgg tgtcgttgca gaagcaatgg tcaccctggt    600

```
tctcgcccgc gcagtcctgc agaaattcgg cggtgactcc ctgagtgaaa ccaagagcaa    660
cattgacacc tacctcaaaa acattgagga acgaatgaaa ttcgaaggtt tagaggatgg    720
agcgtaatga agtgaatgat caaattcact tagatcatca atcagatgac acctctgaat    780
gctcctgccc gatcgtggtt cttgtgggtt tgccaggagc tggaaaatcc accattggac    840
gtcgattagc gcgcgcctta aacactgaac tcgtcgactc cgacgaactc attgagcgcg    900
ccaccggaaa agcctgcggc gccgtgttca gcgagctcgg cgagccagcc ttccgcgagc    960
tcgaggccat ccacgtggcc gaagcactga atcctccgg agtggtgagc ttgggaggcg    1020
gatctgtgct gacagaatcc acccgtgaac tgctcaaagg ccacgacgtg gtctggatcg    1080
acgtgccagt agaagaaggc atcaggcgca ccgcaaacga gcgttcccgc cccgtgctgc    1140
aagccgccga ccccgccgag cactaccgca acctggtgaa agtgcgcacc ccgttgtacg    1200
aagaggtggc aacctaccga cttcgcacca acaaccgcag cccccagcaa gtggtggcag    1260
cagtgttgca tcatctagaa atcgattaat taaaccgggc acctgattaa cattgggctg    1320
cccggtttct tcctattaca agcgaaaggc aacgtgcccc atgagcgcag cgcagatttt    1380
caacaccgtc cacgtcaatg gatcttcccc ctatgatgtc cacattggtt ccggcctcaa    1440
cgagctcatt gttcagcgcg cagcggaatc aggcgcggag caggtagcga ttttgcacca    1500
gcccagcatg gatgacattg catccgagtt ggatgcagca ctagtcgctg ctggtttgaa    1560
ggtcctgcac cttaatgttc ccgatgcgga aaacggcaag tccttggaag tagcggggca    1620
gtgctgggat gaattgggtg gcgcagcatt cggccgccgc gatatcgtca tcggacttgg    1680
tggcggtgct gccacagatc tcgcgggatt cgtcgctgct gcgtggatgc gtggcgtgcg    1740
cgtcattcag gttccaacca ccttgttggc catggtggac gctgcggtgg gcggcaagac    1800
tggcatcaat accgccgcag gcaagaacct tgtgggcgcg ttccacgagc ctgacgcagt    1860
attcattgac accgaacgcc tagccaccct gcctgacgcg gaaatcatcg cgggatccgc    1920
cgaaatcatc aaaactggtt tcatcgccga cccagaaatc ctgcgccttt acgaaactga    1980
tccccgcagcc tgcctgaaga aagaagtcga aggctcccac ctacctgaac tgatttggcg    2040
ctccgtcacc gtcaagggct ccgtggtcgg ccaagacctc aaagaatcta gcctgcgcga    2100
aatcctcaac tacggacaca cctttgccca cgccgtcgaa ctccgcgaaa acttccgctg    2160
gcgccacggc aatgccgttg cagtg                                          2185
```

<210> SEQ ID NO 92
<211> LENGTH: 28
<212> TYPE: DNA
<213> ORGANISM: Artificial sequence
<220> FEATURE:
<223> OTHER INFORMATION: PCR primer

<400> SEQUENCE: 92
aggcatgcgg aggtgctctc tcacgtaa                                        28

<210> SEQ ID NO 93
<211> LENGTH: 27
<212> TYPE: DNA
<213> ORGANISM: Artificial sequence
<220> FEATURE:
<223> OTHER INFORMATION: PCR primer

<400> SEQUENCE: 93
tcccccgggc gagcactacc gcaacct                                         27

```
<210> SEQ ID NO 94
<211> LENGTH: 28
<212> TYPE: DNA
<213> ORGANISM: Artificial sequence
<220> FEATURE:
<223> OTHER INFORMATION: PCR primer

<400> SEQUENCE: 94
tcccccgggc cggaggattt cagtgctt                                           28

<210> SEQ ID NO 95
<211> LENGTH: 28
<212> TYPE: DNA
<213> ORGANISM: Artificial sequence
<220> FEATURE:
<223> OTHER INFORMATION: PCR primer

<400> SEQUENCE: 95
aggcatgcca ctgcaacggc attgccgt                                           28
```